US012648976B2

(12) United States Patent
Roach et al.

(10) Patent No.: US 12,648,976 B2
(45) Date of Patent: Jun. 9, 2026

(54) METHODS FOR PURIFYING BACTERIOPHAGE AND PRODUCTS OF MANUFACTURE CONTAINING ENDOTOXIN-FREE BACTERIOPHAGE PREPARATIONS

(71) Applicant: San Diego State University (SDSU) Foundation, San Diego, CA (US)

(72) Inventors: Dwayne R. Roach, San Diego, CA (US); Tiffany Luong, Los Angeles, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 797 days.

(21) Appl. No.: 17/802,849

(22) PCT Filed: Feb. 26, 2021

(86) PCT No.: PCT/US2021/020004
§ 371 (c)(1),
(2) Date: Aug. 26, 2022

(87) PCT Pub. No.: WO2021/174066
PCT Pub. Date: Sep. 2, 2021

(65) Prior Publication Data
US 2023/0101799 A1     Mar. 30, 2023

Related U.S. Application Data

(60) Provisional application No. 62/983,453, filed on Feb. 28, 2020.

(51) Int. Cl.
A61K 35/76      (2015.01)
A61P 31/04      (2006.01)
B01D 61/14      (2006.01)
C12N 7/02       (2006.01)

(52) U.S. Cl.
CPC .............. *A61K 35/76* (2013.01); *A61P 31/04* (2018.01); *B01D 61/145* (2013.01); *C12N 7/02* (2013.01); *B01D 2315/10* (2013.01); *C12N 2795/00051* (2013.01)

(58) Field of Classification Search
CPC ..... A61K 35/76; B01D 61/45; B01D 2315/10
See application file for complete search history.

(56) References Cited

U.S. PATENT DOCUMENTS

2011/0281329 A1     11/2011  Lenherr et al.
2013/0084337 A1*     4/2013  Wright .................... A61P 25/28
                                                         424/490

OTHER PUBLICATIONS

Mancuso, "Bioprocessing of Bacteriophages and Bacteriocins: Continuous Culture and Downstream Purification", Doctoral Thesis, Loughborough University, Loughborough, England, pp. 1-160. (Year: 2020).*
Liao, YT., et al., "Investigation of prevalence of free Shiga toxinproducing *Escherichia coli* (STEC)-specific bacteriophages and its correlation with STEC bacterial hosts in a produce-growing area in Salinas, California", PLOS One, vol. 13(1), pp. 1-2. (Year: 2018).*
Van Belleghem, JD., et al., "A comparative study of different strategies for removal of endotoxins from bacteriophage preparations", Journal of Microbiological Methods, vol. 132, pp. 153-159. (Year: 2017).*
Manusco, F. "Bioprocessing of bacteriophages and bacteriocins: continuous culture and downstream purification". Loughborough University, a dissertation. Https://ethos.bl.uk/OrderDetails.do?uin=uk.bl.ethos.799196. 2019, Publication Date: Jan. 13, 2020.
Boratysnski, J et al. "Preparation of endotoxin-free bacteriophages". Cellular & Molecular 1-3 Biology Letters . . . Jan. 1, 2004; Entire Document.
Castro-Meija, J et al. "Optimizing protocols for extraction of bacteriophages prior to metagenomic analyses of phage communities in the human gut" . . . Nov. 17, 2015; Entire Document; DOI: 10.1186/s40168-015-0131-4.

* cited by examiner

*Primary Examiner* — Melenie L Gordon
*Assistant Examiner* — Grant C Currens
(74) *Attorney, Agent, or Firm* — Gregory P. Einhorn; Greer, Burns & Crain, Ltd.

(57)     ABSTRACT

In alternative embodiments, provided are compositions, including products of manufacture and kits, and methods, for purifying bacteriophage. Provided herein is are practicable methods, or protocols, that are "Good Laboratory Manufacturing Practice" (GLMP), for phage isolation, selection, liter-scaled cultivation, and purification. In alternative embodiments, GLMP protocols as provided herein employ membrane filtration processes to yield at least about 300 treatment doses at about $10^9$ plaque-forming units with endotoxin levels within human therapeutic regulatory limits. In alternative embodiments, provided are formulations or pharmaceutical preparations of bacteriophage comprising $10^9$ PFU, $10^{10}$ PFU, $10^{11}$ PFU, or $10^{12}$ PFU or more per unit dose and endotoxin levels below about 5.5 $EU \cdot mL^{-1}$, or below about 5.0 $EU \cdot mL^{-1}$.

21 Claims, 22 Drawing Sheets

| Sourcing & Isolating Phage Strains | • combine bacterial host at $OD_{600}$ 0.2 and 0.2μm filtered environmental sample<br>• add molten agar, mix & pour over plate<br>• incubate until plagues become visible<br>• select PFUs based on morphology, resuspend in buffer<br>[repeat until PFUs are uniform] |
|---|---|
| Phage Titration | *Option A)*<br>• prepare serial dilutions of phage stock<br>• combine dilutions with bacterial culture at $OD_{600}$ 0.2<br>• add molten agar, mix & pour over plate & incubate<br>*Option B)*<br>• on dried plate spread bacterial culture $OD_{600}$ 0.2, remove excess and dry<br>• prepare serial dilutions of phage stock<br>• spot phage on plate, dry & incubate |
| Annotation and bioinformatic analysis of phage genomes | • DNA extraction<br>• sequencing libary preparation using<br>• DNA sequencing (Nanopore MinION)<br>• bioinformatic analyses *(e.g. canu, abricate. phacts)* |

FIG. 1A

Agar overlay phage isolation

DNA sequencing

MinION

Liter-scale cultivation filter cap

High-speed centrifugation bacterial pellet a                    intake
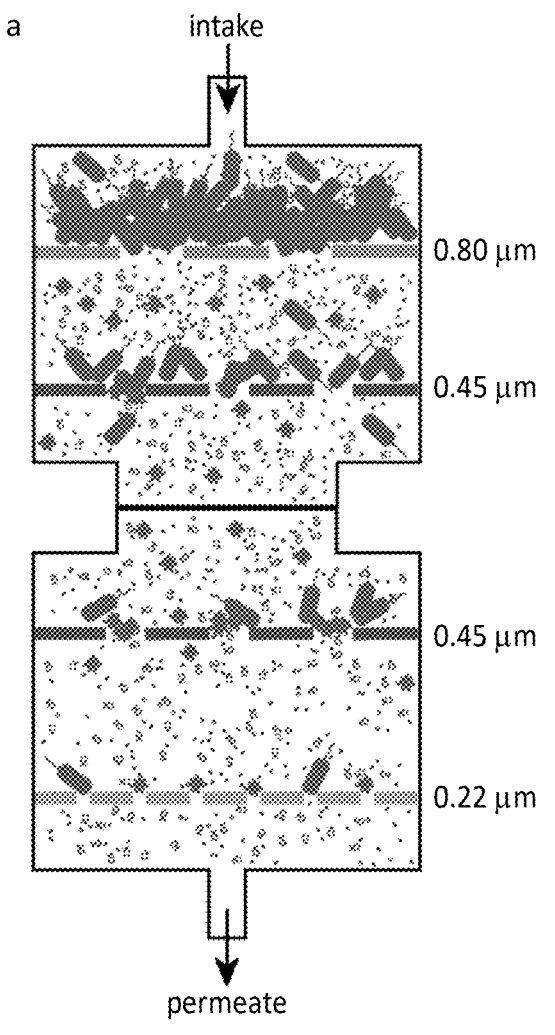
0.80 μm
0.45 μm
0.45 μm
0.22 μm
permeate
b
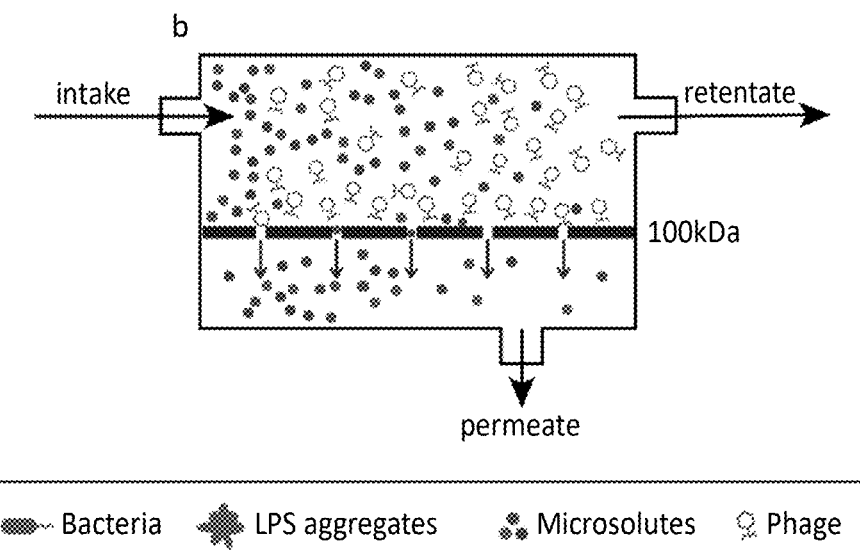
intake                              retentate
100kDa
permeate
| | | | |
|---|---|---|---|
| Bacteria | LPS aggregates | Microsolutes | Phage |
FIG. 3

Table 1. Troubleshooting.

| Step | Problem | Possible reason | Solution |
|------|---------|-----------------|----------|
| 1 | No plaques | Environmental sample too dilute | Concentrate sample with CFF or PEG/NaCl precipitation |
| 16 | Unable to filter | High cell debris | Centrifuge the lysate a third time. Process less lysate at a time |
| 17 | Low phage titer | Low bacterial cell growth | Add phages at an earlier OD (less bacteria) |
| 45 | Fuzzy band at top | Bacterial debris | 0.2 um syringe filter the CFF fraction prior to ultracentrifugation |
| 45 | Multiple bands | Unwanted phage contaminant | Repeat ultracentrifugation of a single band retrieved |
| 52 | Loss of phages | Phages were damaged by osmotic shock | Use 0.5 M PBS for the first dialysis step before switching to water |
| 55 | Loss of phages | LPS bound phages | Spike phage stock with 40mM NaCl |
| 59 | Undetectable EU | High endotoxin level | Dilute the phage stock in sterile PBS |

FIG. 6

| Phage Strain* | Bacterial Host | Purification Step | | | | | | | | Final Product§ |
| | | Sterile Lysate (mL⁻¹) | | Cross-Flow Filtration (mL⁻¹) | | Density Gradient Ultracentrifugation & Dialysis (mL⁻¹) | | LPS-affinity Chromatography (mL⁻¹) | | |
| | | PFU† | EU‡ | PFU | EU | PFU | EU | PFU | EU | EU 10⁹ PFU⁻¹ |
|---|---|---|---|---|---|---|---|---|---|---|
| PAK_P1 | P. aeruginosa | $2.04 \times 10^{10}$ | $2.09 \times 10^5$ | $2.13 \times 10^{11}$ | 29.14 | $5.19 \times 10^{11}$ | 42.77 | $5.78 \times 10^{10}$ | 4.49 | 0.0173 |
| PAK_P5 | P. aeruginosa | $4.33 \times 10^{10}$ | $5.84 \times 10^4$ | $2.00 \times 10^{12}$ | 39.48 | $2.30 \times 10^{12}$ | 39.91 | $4.00 \times 10^{11}$ | 4.30 | 0.00250 |
| E217 | P. aeruginosa | $3.05 \times 10^{10}$ | $1.94 \times 10^5$ | $1.14 \times 10^{11}$ | 37.08 | $2.00 \times 10^{11}$ | 40.61 | $1.89 \times 10^{11}$ | 5.26 | 0.00529 |
| PYO2 | P. aeruginosa | $2.50 \times 10^{10}$ | $1.35 \times 10^4$ | $3.67 \times 10^{12}$ | 39.38 | $2.81 \times 10^{12}$ | 35.83 | $4.00 \times 10^{12}$ | 5.05 | 0.000250 |
| JG265 | K. oxytoca | $1.00 \times 10^9$ | $4.98 \times 10^5$ | $1.20 \times 10^{10}$ | 55.67 | $2.50 \times 10^{10}$ | ND† | $1.30 \times 10^{10}$ | 24.10 | 0.07 |
| JG266 | K. oxytoca | $2.00 \times 10^9$ | $5.43 \times 10^5$ | $9.00 \times 10^9$ | 60.58 | $4.00 \times 10^9$ | ND | $2.00 \times 10^9$ | 17.30 | 0.05 |
| SM219 | S. marcescens | $1.60 \times 10^9$ | $5.16 \times 10^5$ | $5.00 \times 10^{10}$ | 37.22 | $8.50 \times 10^{10}$ | 33.84 | $2.90 \times 10^{10}$ | 18.85 | 0.0345 |

GenBank Accession #: PAK_P1, KC862297.1; PAK_P5, KC862301.1; E217, MF490240; PYO2, MF490236.

† PFU (plaque forming units); ND (not determined)

‡ EU (endotoxin units) determined by the Pierce™ LAL chromogenic endotoxin quantitation kit.

§ Estimated final product EU in a single 1 mL treatment dose with $1 \times 10^9$ PFU; a common dose used in eIND phage therapy.

FIG. 7

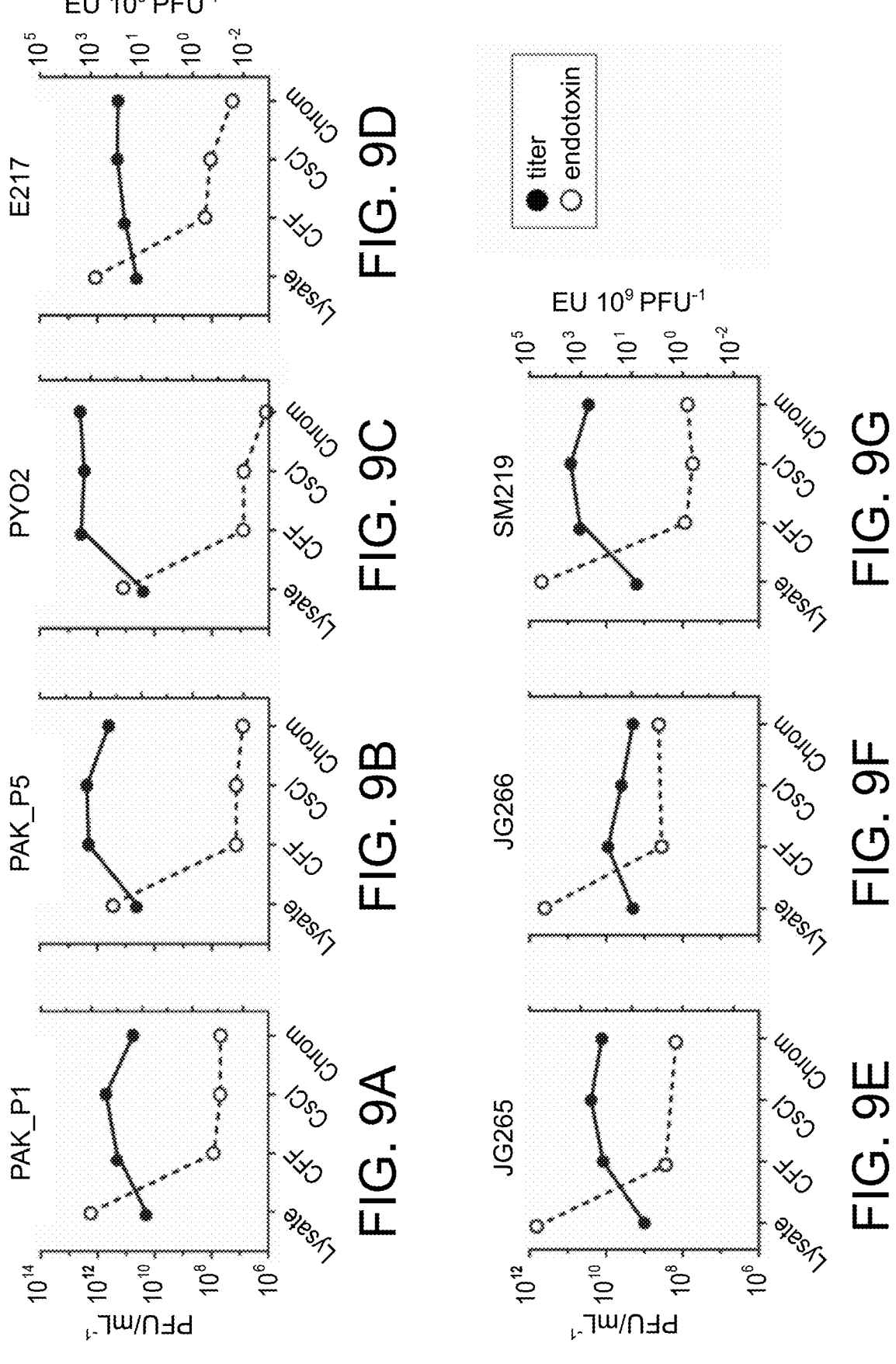

| Phage strain* | Bacterial host | PFU ( mL$^{-1}$) | Endotoxin units ( mL$^{-1}$)$^{‡}$ | Final volume (mL) | Estimated doses at 10$^9$ PFU | EU 10$^9$ PFU$^{-1}$$^{§}$ |
|---|---|---|---|---|---|---|
| PAK_P1 | *P. aeruginosa* | $5.78 \times 10^{10}$ | 4.49 | 24 | 1,387 | 0.0173 |
| PAK_P5 | *P. aeruginosa* | $4.00 \times 10^{11}$ | 4.30 | 30 | 12,000 | 0.00250 |
| E217 | *P. aeruginosa* | $1.89 \times 10^{11}$ | 5.26 | 21 | 3,970 | 0.00529 |
| PYO2 | *P. aeruginosa* | $4.00 \times 10^{12}$ | 5.05 | 16 | 64,000 | 0.000250 |
| JG265 | *K. oxytoca* | $1.30 \times 10^{10}$ | 24.10 | 28 | 364 | 0.07 |
| JG266 | *K. oxytoca* | $2.00 \times 10^{9}$ | 17.30 | 29 | 58 | 0.05 |
| SM219 | *S. marcescens* | $2.90 \times 10^{10}$ | 18.85 | 19 | 552 | 0.0345 |

\* GenBank Accession #: PAK_P1, KC862297.1; PAK_P5, KC862301.1; E217, MF490240; PYO2, MF490236.

$^{†}$ PFU (plaque forming units) determined by Step 20 Option B.

$^{‡}$ EU (endotoxin units) determined by the Pierce™ LAL chromogenic endotoxin quantitation kit Steps 135-143.

$^{§}$ Estimated final product EU in a single 1 mL treatment dose with $1 \times 10^9$ PFU; a common dose used in eIND phage therapy.

FIG. 11

| Step | Problem | Possible Cause | Solution |
|---|---|---|---|
| 7 | No visible clear zones (i.e. plaques) | Bacterial cells poorly lysed | Select alternative bacterial host strain |
| 20 | Not quantifiable due to the presence of pinpoint plaques | Low viral count in environmental sample | Concentrate environmental sample by, for example, CFF (Steps 93-105) or PEG/NaCl precipitation [9,32] |
|  |  | Actual plaque morphology on target bacterial host strain | Use a lighted magnifying glass over a dark backdrop to count plaques or switch to alternative bacterial host strain [95] |
| 91 | Filter clogging | Large amounts of cell debris in supernatant after centrifugation | Centrifuge phage lysate a 3rd time (Steps 88-89) or process 1 L of lysate per batch. |
| 92 | Phage titer <10⁹ PFU·mL⁻¹. | Poor bacteria growth | Optimize bacterial growth conditions and/or reduce phage MOI for Step 86 |
|  |  | Poor phage replication or low phage burst | Produce larger volume of phage lysate (Setup more flasks at step |
| 111 | Fuzzy band observed at top of gradient | Gross bacterial debris present in phage concentrate | 0.2 um syringe filter the CFF fraction prior to proceeding to Step 106 |
| 120 | Multiple bands observed | Unwanted phage contaminant present in the phage concentrate | Repeat steps 106-109, but with 7 mL of d= 1.5 in Step 106 and ultracentrifugation at 38,000 ×g for 18 h at 4 °C in Step 109 |
| 120 | Phage titer drops by >1 log | Phages may be damaged by osmotic shock | Use 50/50 mix of water and 0.5 M PBS for the first dialysis in Step 112 |
| 134 | Phage titer drops by >1 log | Phages bound to column resin | Spike phage stocks with 40mM NaCl before adding phages to the column in Step 130. |
| 143 | Endotoxin signal beyond recommended standard range | Endotoxin >1 EU·mL⁻¹ | Dilute phage sample 10 to 100-fold in sterile PBS before adding to the microtiter plate in Step 137. |

FIG. 12

| Phage Strain* | Bacterial Host | Sterile Phage Lysate (Steps 84-92; mL$^{-1}$) | | Cross-Flow Filtration (Steps 93-105; mL$^{-1}$) | | Density Gradient Ultracentrifugation & Dialysis (Steps 106-120; mL$^{-1}$) | | LPS-affinity Chromatography (Steps 121-134; mL$^{-1}$) | |
|---|---|---|---|---|---|---|---|---|---|
| | | PFU† | EU‡ | PFU | EU | PFU | EU | PFU | EU |
| PAK_P1 | P. aeruginosa | $2.04 \times 10^{10}$ | $2.09 \times 10^5$ | $2.13 \times 10^{11}$ | 29.14 | $5.19 \times 10^{11}$ | 42.77 | $5.78 \times 10^{10}$ | 4.49 |
| PAK_P5 | P. aeruginosa | $4.33 \times 10^{10}$ | $5.84 \times 10^4$ | $2.00 \times 10^{12}$ | 39.48 | $2.30 \times 10^{12}$ | 39.91 | $4.00 \times 10^{11}$ | 4.30 |
| E217 | P. aeruginosa | $3.05 \times 10^{10}$ | $1.94 \times 10^5$ | $1.14 \times 10^{11}$ | 37.08 | $2.00 \times 10^{11}$ | 40.61 | $1.89 \times 10^{11}$ | 5.26 |
| PYO2 | P. aeruginosa | $2.50 \times 10^{10}$ | $1.35 \times 10^4$ | $3.67 \times 10^{12}$ | 39.38 | $2.81 \times 10^{12}$ | 35.83 | $4.00 \times 10^{12}$ | 5.05 |
| JG265 | K. oxytoca | $1.00 \times 10^9$ | $4.98 \times 10^5$ | $1.20 \times 10^{10}$ | 55.67 | $2.50 \times 10^{10}$ | ND† | $1.30 \times 10^{10}$ | 24.10 |
| JG266 | K. oxytoca | $2.00 \times 10^9$ | $5.43 \times 10^5$ | $9.00 \times 10^9$ | 60.58 | $4.00 \times 10^9$ | ND | $2.00 \times 10^9$ | 17.30 |
| SM219 | S. marcescens | $1.60 \times 10^9$ | $5.16 \times 10^5$ | $5.00 \times 10^{10}$ | 37.22 | $8.50 \times 10^{10}$ | 33.84 | $2.90 \times 10^{10}$ | 18.85 |

* GenBank Accession #: PAK_P1, KC862297.1; PAK_P5, KC862301.1; E217, MF490240; PYO2, MF490236.

† PFU (plaque forming units) determined by Step 20 option B; ND (not determined)

‡ EU (endotoxin units) determined by the Pierce™ LAL chromogenic endotoxin quantitation Steps 135-143.

METHODS FOR PURIFYING BACTERIOPHAGE AND PRODUCTS OF MANUFACTURE CONTAINING ENDOTOXIN-FREE BACTERIOPHAGE PREPARATIONS

RELATED APPLICATIONS

This U.S. National Phase Patent Application claims benefit of priority under 35 U.S.C. § 371 to Patent Convention Treaty (PCT) International Application PCT/US2021/020004, filed Feb. 26, 2021, now pending, which claims the benefit of priority under 35 U.S.C. § 119(e) of U.S. Provisional Patent Application Ser. No. (USSN) 62/983,453, filed Feb. 28, 2020. The aforementioned applications are expressly incorporated herein by reference in their entirety and for all purposes. All publications, patents, patent applications cited herein are hereby expressly incorporated by reference for all purposes.

STATEMENT AS TO FEDERALLY SPONSORED RESEARCH

This invention was made with government support under RC2DK116713 awarded by the National Institutes of Health (NIH). The government has certain rights in the invention.

TECHNICAL FIELD

This invention generally relates to bacteriophage biology and infectious diseases. In alternative embodiments, provided are compositions, including products of manufacture and kits, and methods, for purifying bacteriophage. In alternative embodiments, provided herein are practicable methods, or protocols, that can be "Good Laboratory Manufacturing Practice" (GLMP), for phage isolation, selection, liter-scaled cultivation, and purification. In alternative embodiments, GLMP protocols as provided herein employ membrane filtration processes to yield at least about 300 treatment doses at about $10^9$ plaque-forming units with endotoxin levels within human therapeutic regulatory limits. In alternative embodiments, provided are formulations or pharmaceutical preparations of bacteriophage comprising $10^9$ PFU, $10^{10}$ PFU, $10^{11}$ PFU, or $10^{12}$ PFU or more per unit dose and endotoxin levels below about 5.5 EU·mL$^{-1}$, or below about 5.0 EU·mL$^{-1}$.

BACKGROUND

With the usefulness of antibiotics waning, there is an urgent need to develop new treatments against antibiotic resistant infections before they become the leading cause of human death worldwide. Now, researchers and medical doctors have found a way forward—by looking back at how infections were treated before the advent of antibiotics, namely phage therapy. Although bacteriophages (phages) continue to lack drug approval in Western medicine, an increasing number of patients are treated on an emergency investigational new drug (eIND) basis.

Academic and military research institutions are being called to immediate action to produce bacteriophages, i.e., viruses that kill bacteria, for the treatment of antibiotic resistant infections prior to drug approval[1-4]. Sometimes called compassionate use, expanded access provides a patient with an immediately life-threatening condition or serious disease rapid access to an IND when no satisfactory alternative therapy options are available[5]. While demand for bacteriophages is increasing in several fields including human and veterinary drugs, biological products, food supply, and cosmetics[4,6,7], only a limited number of phage products are produced under good manufacturing practices (GMP)[8,9]. An effective, consistent, and controllable process for phage production, which also meets safety and efficacy demands for human and animal clinical use, has yet to be achieved[10,11]. Medicinal phage products have generally been of low purity and titer[1,4,12-14].

Phage producers have largely disregarded unknown gross impurities in phage products that may also risk human health. Indeed, several studies have shown that phage preparations can be safe in animal models[22-24 22-25]. However, experimental phage therapy studies generally cultivate phages with laboratory-adapted reference bacterial strains. For eIND usage, large quantities of a pathogen, often a clinical multidrug resistant (MDR) isolate, are required to produce a high number of phages. Currently, experimental phage purification is practiced by several ad-hoc approaches[18,26-33]. Although these disparate approaches have produced phages, several pitfalls materialized, including low recovery, high gross impurities, inadequate endotoxin removal, and addition of toxic chemicals[11,18,31-34]. Furthermore, currently practiced phage purification approaches were not developed with human phage therapy in mind. In order to achieve a broader application in humans, phage products must comply with strict quality standards.

Several ad-hoc laboratory approaches are currently employed for phage cultivation and purification for human use, which have been largely developed for small experimental studies. Large-scale GMP pharmaceutical production of large phage libraries will likely be needed to meet the demands for personalized phage therapy. However, this approach is currently not time and cost-effective, thus creating an unmet need for systematic small batch phage production to excel current efforts for expanded access phage therapy.

SUMMARY

In alternative embodiments, provided are methods for purifying a plurality of bacteriophage (phage) (or generating a purified preparation of phage), comprising: all or several of the steps as illustrated in FIG. 1 and/or FIG. 2, wherein the method comprises use of a pressure-driven cross-flow ultrafiltration (CFF) comprising a molecular weight cut-off (MWCO) at about 100 kDa, thereby only retaining bacteriophage (phage) particles of greater than about 100 KDa.

In alternative embodiments, provided are methods for purifying a plurality of bacteriophage (phage) (or generating a purified preparation of phage), and generating a substantially endotoxin free preparation of phage, comprising:

(a) providing a sample comprising phage, wherein optionally the phage propagated are added during mid-log stage of bacterial growth, and (b) filtering, or ultrafiltering, the sample with a dead-end microfiltration and a pressure-driven cross-flow ultrafiltration (CFF) comprising a molecular weight cut-off (MWCO) at about 100 kDa, filtering with dead-end microfiltration and/or cross-flow ultrafiltration (CFF), optionally filtering with dead-end microfiltration and/or CFF as illustrated in FIG. 3 or FIG. 8, wherein a membrane pore size of 100 kDa provides the ability to filter out an equivalent to a spherical particle with a 3 nm diameter, thereby having the ability to retain most phages, or substantially most phages, where in alternative embodiments about 90%, 95%, 95%, 97%, 98%, or 99% of intact phages are retained, wherein any material smaller than a cross-flow membrane pore passes through the membrane, while larger phage particles remain in the retentate stream, and the CFF with an about 100 kDa membrane pore size removes both free endotoxin, which are approximately 10 kDa in size, and all known exotoxins, which are typically smaller than about 30 kDa, thereby generating a substantially endotoxin free preparation of phage.

In alternative embodiments of the methods, the preparation of phage comprises endotoxin levels to below about 5.5 $EU \cdot mL^{-1}$, or below about 5.0 $EU \cdot mL^{-1}$.

In alternative embodiments of the methods, a preparation, or a single production run, produces at least about 300 treatment doses phage at about $10^9$ PFU, $10^{10}$ PFU, $10^{11}$ PFU, or $10^{12}$ PFU, or more per dose.

In alternative embodiments of the methods, phage lysates or cultures are cooled to below 37° C., or cooled to between about 4° C. to 37° C., at the point where phage-insensitive or phage-resistant bacteria appear in culture.

In alternative embodiments, provided are pharmaceutical preparations or formulations of bacteriophage (phage), comprising: about $10^9$ PFU, $10^{10}$ PFU, $10^{11}$ PFU, or $10^{12}$ PFU or more per unit dose and endotoxin levels below about 5.5 $EU \cdot mL^{-1}$, or below about 5.0 $EU \cdot mL^{-1}$.

In alternative embodiments of the pharmaceutical preparations or formulations:

the phage are formulated for enteral or parenteral administration, or are formulated for administration intramuscularly, orally, parenterally, by inhalation spray, nasally, topically, intrathecally, intrathecally, intracerebrally, epidurally, intracranially, vaginally or rectally;

the phage are formulated as a lyophilate, a tablet, a pill, a powder, a dragee, a capsule, a liquid, a lozenge, a gel, a syrup, a slurry or a suspension; and/or pharmaceutical preparations or formulations comprise or further comprise a pharmaceutically acceptable excipient, or phage dissolved in (optionally sterile) saline, water, polyethylene glycol, propylene glycol, ethanol or oils such as safflower oil, corn oil, peanut oil, cottonseed oil or sesame oil, tragacanth gum, and/or a buffer.

In alternative embodiments, provided are methods for treating a bacterial infection in vivo comprising administering to an individual in need thereof a formulations or pharmaceutical preparation as provided herein, wherein optionally the formulations or pharmaceutical preparation is administered orally, parenterally, by inhalation spray, nasally, topically, intrathecally, intrathecally, intracerebrally, epidurally, intracranially, vaginally or rectally.

In alternative embodiments, provided are uses of a formulation or pharmaceutical preparation as provided herein, for treating a bacterial infection in vivo.

In alternative embodiments, provided are formulations or pharmaceutical preparations as provided herein, for use in treating a bacterial infection in vivo.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

FIG. 2A Example agar overlay petri plate showing a variety of plaque morphologies for de novo phage isolation; FIG. 2B Phage genome sequencing with the Oxford Nanopore MinION device and computer; FIG. 2C Liter-scaled shake flask cultivation of phages, a filter cap was used to facilitate sterile aerobic bacterial growth; FIG. 2D High-speed centrifugation of phage enriched cultures to remove gross bacterial debris; FIG. 2E Schematic of liter-scaled phage lysate sterilization using a peristaltic pump and inline capsule filtration; FIG. 2F Schematic of cross-flow filtration for diafiltration and concentration phage lysates; FIG. 2G representative CsCl density gradient ultracentrifugation with phage PAK_P1; FIG. 2H CsCl 100 kDa MWCO membrane dialysis in chilled PBS; FIG. 2I LPS-affinity chromatography endotoxin removal spin column; FIG. 2J phage titration step: spot plaque assay of serially diluted phage PAK_P1 on a lawn of *P. aeruginosa* (n=2, 3 replicates).

FIG. 3A-B schematically illustrates exemplary protocols as provided herein for removing bacteria and gross impurities from phage lysates: FIG. 3A In-line filtration using dual 0.45 μm and 0.22 μm membranes to remove intact bacterial cells; FIG. 3B Cross-flow filtration removes microsolutes <100 kDa in the permeate, while phages are diafiltrated and concentrated in the retentate.

FIG. 5A-D: *Pseudomonas aeruginosa* phages, FIG. 5A: PAK_P1, FIG. 5B: PAK_P5, FIG. 5C: PYO2, FIG. 5D: E217; FIG. 8E-F: *Klebsiella oxytoca* phages; FIG. 5E JG265; FIG. 5F JG266; and, FIG. 5G *Serratia marcescens* phage SM219.

FIG. 6 illustrates Table 1 showing exemplary user variations of exemplary methods as provided herein.

FIG. 7 illustrates Table 2, which is a summary of phage titer and endotoxin quantification after each purification step, i.e., summarizing gram-negative bacteriophage cultivation and purification titers and endotoxin units after each production step, as further discussed in Example 1, below.

FIG. 9A-G graphically illustrate process stepwise phage titer and endotoxin concentration throughout processing; plaque forming units (PFU) per mL (right y-axis; closed circles) and endotoxin units (EU) normalized to $10^9$ PFU (left x-axis, open circles) after phage lysate sterilization (lysate, see for example step 92, of Example 2), cross-flow ultrafiltration (CFF, see for example step 105, of Example 2), density gradient ultracentrifugation and dialysis (CsCl, see for example step 120, of Example 2) and LPS-affinity chromatography (Chrom, see for example step 134, of Example 2); see for example step 20 Option B and steps 121-134, in Example 2, for phage titration and endotoxin quantification procedures, respectively, with FIG. 9A-G showing data for PAK_P1 (FIG. 9A), PAK_P5 FIG. 9B, PY02 FIG. 9C, E217 FIG. 9D, JG265 FIG. 9E, JG266 FIG. 9F, and SM 219 FIG. 9G, respectively.

FIG. 10A illustrates an image of SDS-PAGE analysis of protein content in final phage samples (for example, step 133, of Example 2) at $10^9$ PFU compared to an exemplified sterilized phage lysate (for example, produced by steps 84-92, of Example 2) and Precision Plus Protein ladder (Bio-Rad); and FIG. 10B-G graphically illustrates human HeLa cell-line (FIG. 10B, FIG. 10D, FIG. 10F) and HEK293 cell-line (FIG. 10C, FIG. 10E, FIG. 10G) viability after 24 hour (h) co-incubation with final preparations of *P. aeruginosa* phages (FIG. 10B, FIG. 10C), *K. oxytoca* phages (FIG. 10D, FIG. 10E) and *S. marcescens* phage (FIG. 10F, FIG. 10G) at cell:phages ratio of 1:100 and 1:1000 quantified by the CellTiter-Glo™ assay (for example, see steps 157-167, of Example 2); viability was normalized to untreated cells. *Pseudomonas* and *Serratia* sterilized phage lysates were significantly lower that corresponding final phage preparations (p<0.006), whereas there was no significant difference in cell viability between *Klebsiella* sterilized lysate and phage treated; one-way ANOVA; error bars represent SEM; n=3-6).

FIG. 11 illustrates Table 3 (Example 2) showing bacteriophage product final titer (Step 134, of Example 2), endotoxin level (Step 143, of Example 2), and estimated number of doses produced, the referenced steps as described in Example 2.

FIG. 12 illustrates Table 4, showing troubleshooting suggestions, the referenced steps as described in Example 2.

FIG. 13 illustrates Supplementary Table 1 (discussed in Example 2), the referenced steps as described in Example 2.

after the initial appearance of phage resistant mutant outgrowth, as described in Example 3.

Figure 17:
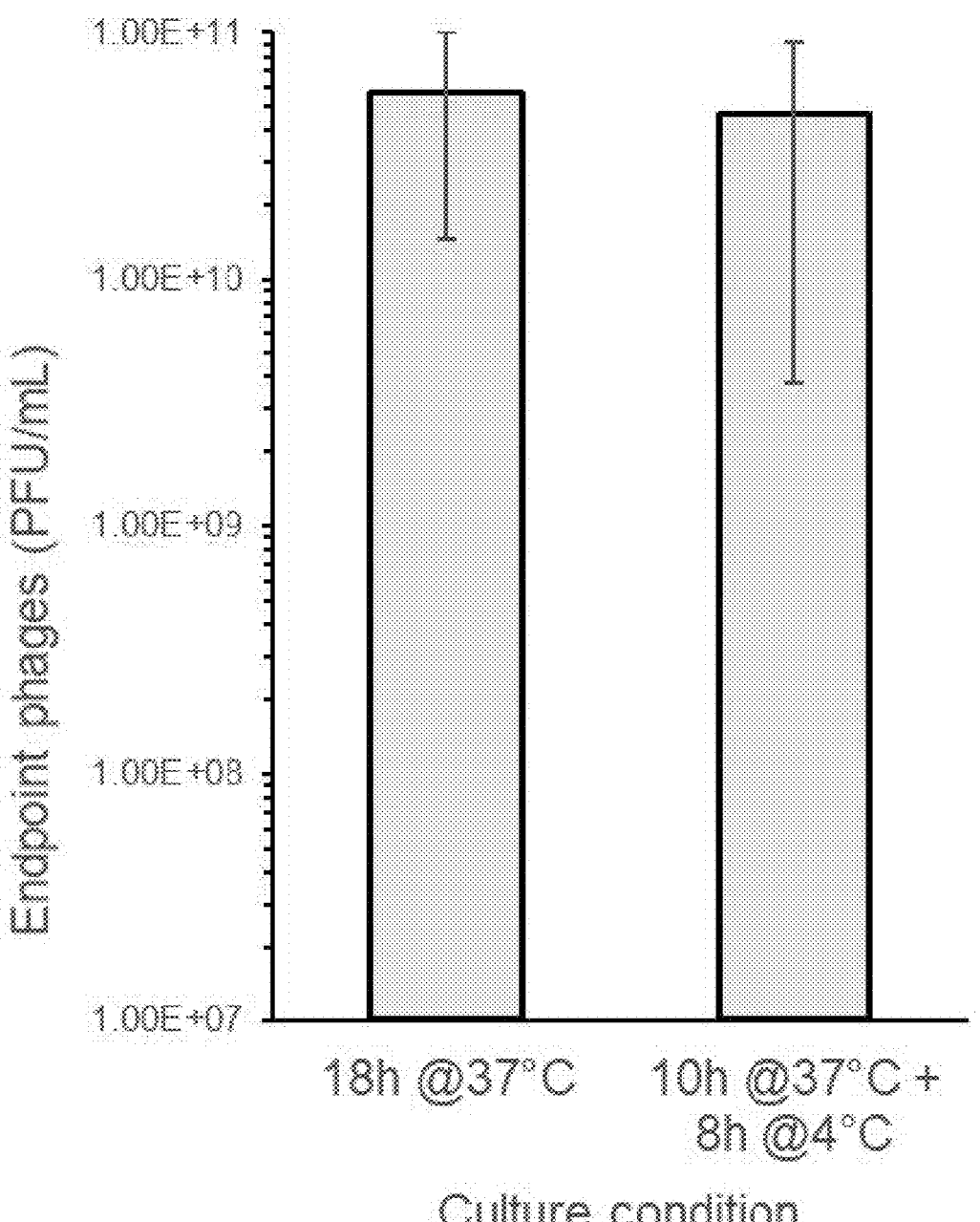

FIG. 17 graphically illustrates cooling during phage cultivation does not reduce virus yield: at the end of phage counts were not statistically different between continuous culturing at 37° C. and cooled cultures after the initial appearance of phage resistant mutant outgrowth, as described in Example 3.

Like reference symbols in the various drawings indicate like elements.

DETAILED DESCRIPTION

In alternative embodiments, provided are compositions, including products of manufacture and kits, and methods, for purifying bacteriophage (phage).

In alternative embodiments, provided herein are practicable methods, or protocols, for phage isolation, selection, liter-scaled cultivation, and purification. These protocols can be termed as a "Good Laboratory Manufacturing Practice" (GLMP). We describe technical issues and solutions to ensure the identity, quality, and purity of phage products for human use. In alternative embodiments, GLMP protocols as provided herein employ modern membrane filtration processes to yield at least 300 treatment doses at $10^9$ plaque-forming units with endotoxin levels within human therapeutic regulatory limits.

In alternative embodiments, protocols or methods as provided herein use cross-flow ultrafiltration (CFF), which is a pressure-driven scalable membrane filtration process that markedly decreases labor and improves purification reproducibility. Use of CFF was able to reliably concentrate phage particles greater than 10-fold, fractionate phages from gross bacterial impurities (for example less than 40 EU·ml⁻¹), and diafilter buffer exchange ((see FIG. 4, FIG. 5 and FIG. 7, Table 2). In alternative embodiments, exemplary protocols are configured as a cost-effective, programmed, and semi-automated single-step (see FIG. 2F, or CFF). In alternative embodiments, exemplary protocols using CFF are also scalable with no barrier to running several apparatuses with additional hardware such as for example a multichannel peristaltic pump head or multiple peristaltic pumps. In alternative embodiments, exemplary protocols using CFF implement a molecular weight cut-off (MWCO) at 100 kDa in combination with several sterile washes; thus, the bulk of the gross impurities (of less than 100 kDa) are removed from phage lysates, including washing away of endotoxin and exotoxins that are smaller than 100 kDa[41]. Thus, exemplary protocols provided herein that comprise use of CFF is a highly cost-efficient methods to concentrate, diafiltrate and purify phages.

In alternative embodiments, protocols or methods as provided herein do not require use of downstream cesium chloride (CsCl) density gradient ultracentrifugation, dialysis, and/or affinity chromatography purification steps, and because these additional processes are not required to meet the FDA's drug product endotoxin regulation[40], exemplary protocols as provided herein can allow phage products to be isolated (for example, de novo isolated), cultivated and purified in less than five (5) days for time-critical emergency phage therapy if needed or desired. While the CsCl density gradient ultracentrifugation, dialysis, and/or affinity chromatography purification steps are optional, their use may result in a homogenous phage band and/or further concentration of phage, so including these steps may be preferred in alternative embodiments.

Implementation of GLMP protocols as provided herein across research laboratories participating in phage production for expanded access phage therapy can be pivotal to re-introduce phage therapy to Western medicine.

In alternative embodiments, protocols or methods as provided herein can produce a phage product that is of high-titer and pure, providing an estimated 3000 treatments at $10^9$ plaque forming units (PFU), a commonly prescribed IV phage dose[1].

Thus, implementation of exemplary protocols as provided herein can allow for administration of higher phage titer per treatment dose and maintain a safe patient exposure endotoxin limit of less than (<) 5 EU·kg$^{-1}$ h$^{-1}$ [40].

In alternative embodiments, protocols or methods as provided herein are GLMP purifications that provide phage for human phage therapy. In alternative embodiments, protocols or methods as provided herein provide high safety standards of phage products, which have been shown to have no toxicity with two human cell lines, see FIG. 10.

In alternative embodiments, protocols or methods as provided herein comprise both bacteriophage cultivation and purification. In alternative embodiments, the procedure starts with sourcing and isolating phages with a target bacterial strain. After multiple rounds of agar plaque isolation, a single plaque is small-scale cultivated overnight. Next, the newly isolated phage genome is sequenced, annotated, and screened for lysogenic and harmful genes. Phages deemed potentially safe for human use are then liter-scale cultivated. After overnight culturing, phage lysate is sterilized by pressure driven double dead-end filtration and cross-flow ultrafiltration; see for example FIG. 3 and FIG. 8 for exemplary filtration schemes. Cross-flow ultrafiltration also diafiltrates to remove growth medium and concentrates phage particles in buffer. As an option, cesium chloride (CsCl) density gradient ultracentrifugation and dialysis can be used to further confirm phage stock homogeneity. LPS-affinity chromatography is used to remove residual endotoxins. Lastly, the final phage preparation purity and safety is tested by quantifying endotoxin level, protein abundance, and cell viability after phage sample exposure.

In expanded access phage therapy, care must be taken to avoid temperate phages that are able to lysogenize their bacterial host. While there are genetic approaches to inactivate the lysogenic lifecycle[2], in alternative embodiments it may be preferable to begin with phages that are unable to lysogenize their host. Phage genome sequencing allows rapid confirmation of whether a phage is likely to be temperate or virulent. Whole-genome sequencing may also provide clues to other biological contaminants in the preparation, depending on the abundance of the contaminants relative to the phage. However, in each of these considerations, phage genome sequencing will only identify known features. Computational identification of a toxin, antibiotic resistance gene, or virulence factor should not infer that these elements are not present, rather than known elements are not present.

In summary, an exemplary protocol as provided herein comprises the steps of:

(1) phage plaque isolation, as described for example in steps 1 to 12 in the exemplary protocol of Example 2;

(2) small scale cultivation, as described for example in steps 13 to 18 in the exemplary protocol of Example 2;

(3) phage titration, as described for example in step 19 in the exemplary protocol of Example 2; (where steps (1) to (3) can take between about 5 to 7 days)

(4) DNA extraction, as described for example in steps 21 to 56 in the exemplary protocol of Example 2;

(5) library preparation, as described for example in steps 57 to 62 in the exemplary protocol of Example 2;

(6) DNA sequencing and analysis, as described for example in steps 63 to 83 in the exemplary protocol of Example 2;

(steps (4) to (6) can take about 3 days)

(7) liter-scale cultivation, as described for example in steps 84 to 90 in the exemplary protocol of Example 2;

(8) dead-end filtration, as described for example in step 91 in the exemplary protocol of Example 2;

(9) phage titration, as described for example in step 92 in the exemplary protocol of Example 2;

(steps (7) to (9) can take about 2 days)

(10) cross-flow ultrafiltration, as described for example in steps 93 to 104 in the exemplary protocol of Example 2;

(11) page titration, as described for example in step 105 in the exemplary protocol of Example 2;

(steps (10) to (11) can take about 2 days)

[optional] (12) density gradient ultracentrifugation, as described for example in steps 106 to 111, in the exemplary protocol of Example 2;

[optional] (13) cesium chloride (CsCl) dialysis, as described for example in steps 112 to 119, in the exemplary protocol of Example 2;

[optional] (14) page titration, as described for example in step 120, in the exemplary protocol of Example 2;

(steps (12) to (14) can take about 2.5 days)

(15) LPS (lipopolysaccharide)-affinity chromatography, as described for example in steps 121 to 133, in the exemplary protocol of Example 2;

(16) phage titration, as described for example in step 134, in the exemplary protocol of Example 2;

(steps (15) to (16) can take about 1 day)

(17) endotoxin quantification, as described for example in step 135 to 143, in the exemplary protocol of Example 2;

(18) protein analysis, as described for example in step 144 to 156, in the exemplary protocol of Example 2; and

(19) cell viability, as described for example in step 157 to 164, in the exemplary protocol of Example 2

(steps (17) to (19) can take about 4 days).

In summary, an exemplary protocol as provided herein comprises the steps of (or any one, several or all steps of):

1. To isolate phage strains de novo, centrifuge aqueous environmental viral sample at 8,000×g for 30 min at 4° C. to remove bulk debris. Volume of aqueous viral sample will be dependent on separation of liquid from solid debris after centrifugation.

2. Decant the supernatant into a clean tube without disturbing debris pellet.

3. 0.2 μm syringe filter the environmental viral sample.

4. In a sterile test tube, mix 100 μL of bacterial host at OD$_{600}$ 0.2 and 100 μL of the filtered viral sample.

5. Add 3 mL of molten soft-agar, mix gently, and pour over solidified agar Petri plate. If the bacterial lawn is clear after incubation, dilute the environmental sample to obtain single plaques.

6. Incubate under appropriate temperature and atmospheric growth conditions for 12-18 h or until plaques form on a confluent lawn of bacteria.

7. Using a Pasteur pipette, select one PFU and re-suspend in 100 μL of PBS in a microcentrifuge tube.

8. Prepare serial dilutions (for example tenfold) in PBS.

9. In sterile test tubes, mix 10 μL of the $10^{-5}$, $10^{-6}$ or $10^{-7}$ dilutions with 500 μL of bacteria grown to OD$_{600}$ 0.2.

10. Add 3 mL of molten soft-agar to each, mix gently, and pour over solidified agar Petri plate.

11. Incubate under appropriate temperature and atmospheric growth conditions for 12-18 h or until plaques are visible on a confluent lawn of bacteria.

12. Repeat Steps 7 through 11. In alternative embodiments, repeat Step 12 three times, or until all PFUs exhibit the same observed plaque morphology.

Small-Scale Cultivation, Timing 15-21 h

13. Using a Pasteur pipette, select one PFU and re-suspend in 100 μL of PBS in a microcentrifuge tube.

14. Warm 50 mL of growth medium in a sterile 250 mL GL45 screw-top flask with a GL45 0.22 μm PTFE membrane vented cap.

15. Add 500 μL of bacteria grown to $OD_{600}$ 0.2 and incubate at appropriate temperature and atmospheric growth conditions for 20 min.

16. Add 50 μL phage obtained in Step 13 and incubate under appropriate bacterial growth conditions for 12-18 h.

17. To remove bulk bacterial debris, transfer lysates to 50 mL conical centrifuge tubes and centrifuge at 6,000×g for 30 min at 4° C.

18. Filter sterilize the supernatant with a 0.2 μm syringe filter into a sterile 50 mL conical tube. Do not disturb the pellet during decanting.

19. Titer the sample as described in Step 20.

Store phage lysate at 4° C. for up to 12 months.

In alterative embodiments, exemplary methods as provided herein also comprise the following steps (or any one, several or all steps of) for phage titration:

20. For routine phage titering, optionally use either of two techniques: Follow 'Option A' for agar overlay titering and 'Option B' for spot plaque titering. Alternatively, phages can be quantified via their genome copy number by qPCR (For details see[49,50]).

OPTION A| Agar Overlay Tittering, Timing 20 h i. Add 100 μL of phage sample into a microcentrifuge tube containing 900 μL of PBS, mix well.

ii. Pipette 100 μL from Step i dilution into a $2^{nd}$ a microcentrifuge tube containing 900 μL of PBS, mix well.

iii. Repeat step ii for the remaining microcentrifuge tubes to create a dilution series of $10^{-1}$ to $10^{-8}$.

iv. In sterile test tubes, mix 100 μL of each serial dilution with 100 μL of bacteria grown to $OD_{600}$ 0.2.

v. Add 3 mL of molten soft-agar, mix gently, and pour the mixture over a solidified agar Petri plate.

vi. Incubate under appropriate temperature and atmospheric growth conditions for 12-18 h or until plaques form on a confluent lawn of bacteria.

vii. Determine phage stock concentration as $PFU \cdot mL^{-1}$.

OPTION B| Spot Plaque Tittering, Timing 19 h i. Dry a growth agar Petri plate for 30 min in a biosafety cabinet.

ii. To seed a lawn of bacteria, pour 3 mL of bacteria grown to $OD_{600}$ 0.2 onto the dry growth agar Petri plate and quickly remove excess culture.

iii. Dry the Petri plate in a biosafety cabinet for 15 min.

iv. While drying, add 90 μL of PBS to 8 wells row-by-row in a 96-well microtiter plate.

v. Add 10 μL of phage sample to the first well, mix well.

vi. Pipette 10 μL from the $1^{st}$ well into the $2^{nd}$ well, mix well.

vii. Repeat step vi for the remaining wells to create a dilution series ($10^{-1}$ to $10^{-8}$).

viii. Using an 8-channel pipette, spot 4 μL from each well onto a dried seeded lawn of bacteria prepared in (i-iii). Completely dry spots before moving the plate to incubator.

ix. Incubate plate at appropriate temperature and atmospheric growth conditions for 12-18 h or until plaques form on a confluent lawn of bacteria.

x. Determine phage stock concentration as $PFU \cdot mL^{-1}$.

In alterative embodiments, exemplary methods as provided herein also comprise the following steps (or any one, several or all steps of) for DNA extraction:

Steps 21-56 describe how to extract genomic DNA from small scale phage lysates following a modified version of a previously published protocol[90]. There are many DNA extraction kits which can be used, including for example the Promega Wizard, Qiagen PowerViral Kit, and Norgen Biotek. This exemplary protocol uses the Ciculomics Nanobind Tissue Big DNA Kit to generate long DNA fragments suitable for the Oxford Nanopore MinION sequencer (or equivalent).

21. Place the lysate from Step 18 into a clean 50 mL centrifuge tube. Add 0.5 μL of nuclease solution per mL of lysate (10 μg·mL$^{-1}$ DNase & RNase final). Incubate the lysates at 37° C. for 30 min, or at RT for 2 h.

22. Add ½ volume of the precipitant solution compared to the lysate (10% (wt/vol) PEG-8000, 1 M NaCl final concentration). Mix gently by inversion. Incubate on ice for at least 60 min; precipitation works best when incubated at 4° C. overnight. Most phages are stable in this state for several days.

23. Centrifuge the precipitated phage lysate at 10,000×g, 4° C., 10 min.

24. Carefully remove the supernatant by either aspiration or carefully pouring into a separate tube, and retain the transparent or slightly opaque pellet in the original tube.

25. Gently, resuspend the pellet in 0.5 mL of 5 mM $MgSO_4$ and briefly (5-10 s) centrifuge at 10,000×g at RT to pellet any remaining insoluble particles.

26. Transfer the supernatant to a sterile microcentrifuge tube for the remaining steps.

27. Before proceeding, dilute the supplied CW1 and CW2 buffers with 96%-100% ethanol, as described by the manufacturer.

28. Add 20 μL of proteinase K solution.

29. Add 20 μL of the supplied CLE3 buffer.

30. Pulse vortex 10 times for 1 s each.

31. Incubate in the ThermoMixer (or equivalent) at 56° C. and 900 rpm for 30 min.

32. Add 200 μL of the supplied BL3 buffer.

33. Pulse vortex 10 times for 1 s each.

34. Incubate microcentrifuge tube in the ThermoMixer (or equivalent) at 56° C. and 900 rpm for 30 min.

35. Add the Nanobind (or equivalent) disks to the lysate.

36. Add 300 μL of isopropanol.

37. Mix microcentrifuge tube by inversion 5 times.

38. Mix on a rotator at 10 rpm for 10 min.

39. Place microcentrifuge tube in the Magnetic Tube Rack.

40. Carefully remove the supernatant taking care not to disturb the Nanobind (or equivalent) disks.

41. Add 700 μL of the supplied CW1 buffer.

42. Mix microcentrifuge tube by vigorous inversion 4 times.

43. Place microcentrifuge tube in the Magnetic Tube Rack

44. Carefully remove the supernatant taking care not to disturb the Nanobind (or equivalent) disks.

45. Add 500 µL of the supplied CW2 (or equivalent) buffer.

46. Repeat Steps 42-45.

47. Mix by vigorous inversion 4 times.

48. Place microcentrifuge tube in the Magnetic Tube Rack.

49. Carefully remove the supernatant taking care not to disturb the Nanobind (or equivalent) disks.

50. Spin the microcentrifuge tube for 5 s.

51. Remove any remaining liquid without disturbing the Nanobind (or equivalent) disks.

52. Repeat Steps 50-51.

53. Add 100 µL of the supplied elution buffer (EB) and incubate at RT for 10 min.

54. Transfer the DNA eluate to a new, sterile, microcentrifuge tube.

55. Spin the microcentrifuge tube containing the Nanobind (or equivalent) disks for 5 seconds (s). Remove additional eluate and pipette into the same microcentrifuge tube in Step 54.

56. Leave at RT for approximately 1 h to let the DNA re-dissolve.

Phage DNA can be stored at 4° C. for less than (<) 2 weeks and −20° C. less than (<) 6 months.

In alterative embodiments, exemplary methods as provided herein also comprise the following steps for sequencing library preparation:

Steps 57-62 use Oxford Nanopore MinION (or equivalent) for rapid DNA sequencing of phage genomes. Thaw all components on ice, and store on ice until needed. Centrifuge all components briefly before use.

57. In a 0.2 mL PCR tube, mix 7.5 µL of phage DNA (>400 ng) preparation from Step 56 and 2.5 µL of fragmentation mix (solution FRA).

58. Mix by gently tapping the tube, and then centrifuge briefly to bring all the contents to the bottom of the tube.

59. Incubate the tube at 30° C. for 1 min and then at 80° C. for 1 min.

60. Add 1 µL of rapid adapter (solution RAP)

61. Mix by gently tapping the tube, and then centrifuge briefly to bring all the contents to the bottom of the tube.

62. Incubate the tube at RT for 5 min.

The sequencing library can be stored briefly on ice until loaded into the DNA sequencer.

DNA sequencing, timing 1-48 h, depending on desired reads coverage, with first reads recovered in an hour. More reads will increase confidence.

In alterative embodiments, exemplary methods as provided herein also comprise any one several or all of the following steps for sequence analysis:

63. Open MinKNOW software (or equivalents) on the computer

Figure 2A:
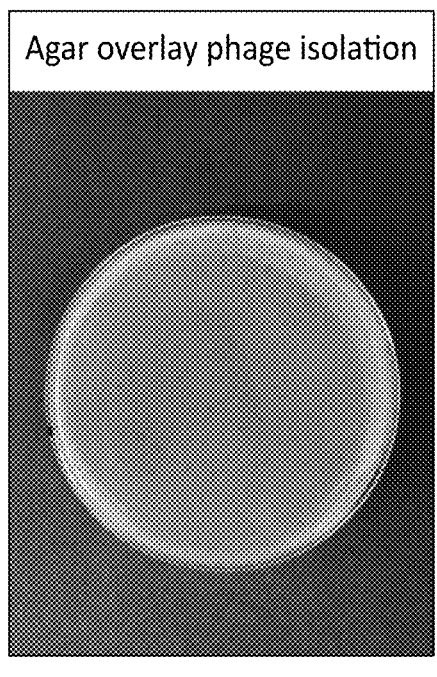
FIG. 2A-J illustrates steps in an exemplary phage production method as provided herein.
Figure 2B:
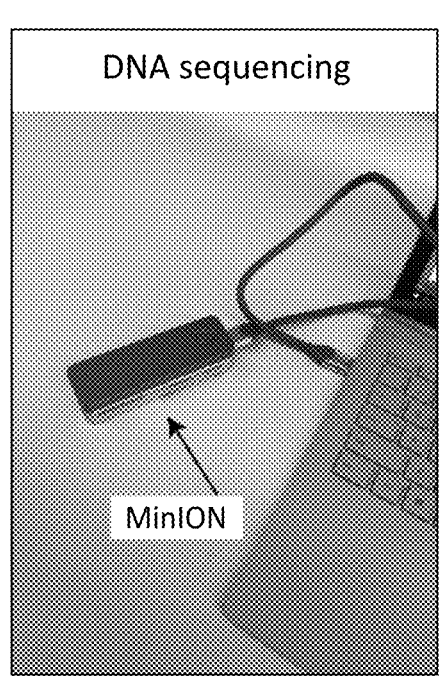

64. Plugin the MinION device (or equivalent) and insert a flow cell (FIG. 2b)

65. Enter the sample ID and flow cell ID on the computer

66. Run the Platform QC script (or equivalent) and confirm active pores available 67. Open the cover of the flow cell, and drawback a few microliters of fluid to remove bubbles, taking care not to remove the buffer from the pores.

68. To prepare the flow cell priming mix, add 30 µL of Flush Tether (FLT) (or equivalent) directly to the tube of mixed flush buffer (FLB), and mix by pipetting up and down. Centrifuge briefly.

69. Load 800 µL of the priming mix into the flow cell via the priming port. Be careful to avoid introducing air bubbles into the flow cell. Incubate at RT for 5 min.

70. Mix the sequencing reaction in a new tube:

34 µL Sequencing Buffer (SQB)

25.5 µL Loading Beads (LB)

4.5 µL Nuclease-free water

70 L DNA library from Step 62

71. Mix by pipetting and centrifuge briefly

72. Access the SpotON (or equivalent) sample port by lifting the cover.

73. Load 200 µL of the priming mix into the flow cell via the priming port prepared in in Step 68. Be careful to avoid introducing air bubbles into the flow cell.

74. Carefully add the 75 µL of sequencing reaction from Step 71, in a dropwise fashion. Be careful to ensure that each drop enters the flow cell.

75. Carefully replace the SpotON (or equivalent) sample port cover ensuring the port is filled by the bung, close the priming port cover and close the MinION (or equivalent) lid.

76. On the MinKNOW software (or equivalent), click Start Run.

77. Upon completion of the sequencing, flow cells can be washed and retained for further use. DNA sequences will be available almost immediately and will continue to accumulate while there are active pores.

In alterative embodiments, exemplary methods as provided herein also comprise any one, several or all of the following steps for bioinformatics analysis:

78. Upload the fastq files from MinKNOW (or equivalent) to a Linux (or equivalent) server, or equivalents 79. Assemble the long reads with canu[91] by running the following code:

a. canu-p phage-d assembly genomeSize=40 k-nanopore-raw phage.fastq The primary options are -p for the name, -d for the location to write the output, and the fastq output from MinKNOW (or equivalent).

80. Compare the phage genomes to antimicrobial and virulence gene databases using Abricate (https://github-.com/tseemann/abricate) by running the following code:

a. for DB in argannot card megares ncbi plasmidfinder resfinder vfdb; do abricate—threads 10—db $DB assembly/done>abricate.out 81. Upload the genome to PHACTS (or equivalent) to predict whether it is virulent or temperate virus[77].

82. Upload the genome to PATRIC (https://patricbrc.org/) (or equivalent) to annotate other genes in the genome.

83. Select phages for large-scale production based on the lack of predicted antibiotic and virulence genes, and the likelihood that the isolated phage is virulent (i.e. strictly lytic lifecycle).

In alterative embodiments, exemplary methods as provided herein also comprise any one, several or all of the following steps for liter-scale shake flask cultivation, or large phage production batches, which can be limited by maximum centrifuge rotor capacity. Steps 84-90 describe how to process 1 L cultures; thus 6 flask cultures are performed in parallel.

84. In a sterile 2 L GL45 (or equivalent) screw-top flask with a GL45 0.22 µm PTFE membrane vented cap, warm 1 L of complex growth medium.

85. Add 5 mL of bacteria grown to $OD_{600}$ 0.2 and incubate appropriate temperature and atmospheric growth conditions for 20 min.

86. Add phage from Step 18 at a Multiplicity of Infection (MOI) of 0.1 and incubate under appropriate bacterial growth conditions for 12-18 h.

Figure 1B:
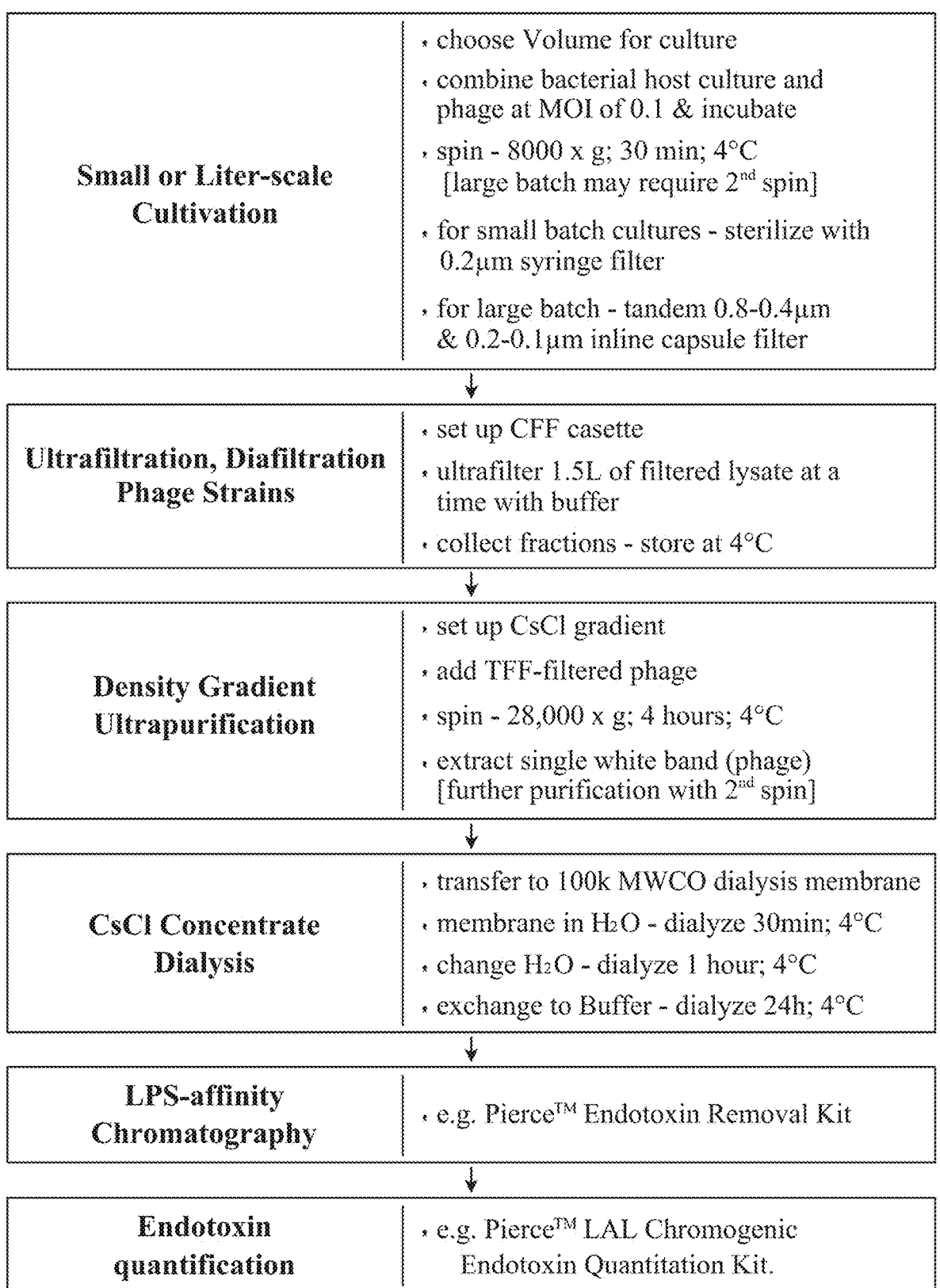
FIG. 1 illustrates a flowchart listing steps of an exemplary method, a Good Laboratory Manufacturing Practice, as provided herein; steps include phage cultivation, phage genome sequencing, bioinformatic analyses, and ultrapurification.

87. To remove bulk bacterial debris, transfer lysates to 1 L centrifuge bottles and centrifuge at 8,000×g for 45 min at 4° C. (FIG. 1).

88. Decant the supernatants into fresh, sterile 1 L centrifuge bottles without disturbing the bacterial pellet.

89. Centrifuge again at 8,000×g for 45 min at 4° C.

90. Decant supernatant into sterile 1 L glass bottle.

In alternative embodiments, phage lysates are cooled at the point where phage resistant bacteria appear in culture, by cooling the overall live bacterial cells and debris are significantly reduced at the end of cultivation. This modifies Step 86 to improve the removal of bulk bacterial debris in step 87. This step can be important because it improves all downstream purification steps by having less, for example, endotoxin to remove from phage preparations. In addition, it enhances filtration steps by having less gross debris that clogs the filter membranes. Importantly, there is no reduction in phage yields.

In alterative embodiments, exemplary methods as provided herein also comprise any one, several or all of the following steps for dead-end filtration:

91. Assemble 0.8/0.45 μm and 0.45/0.2 μm capsule filters inline. Use the peristaltic pump to filter sterilized supernatant into a sterile glass bottles. Capsule filters can process up to 2 L before clogging, but can be cleaned and reused following manufacturer's protocol.

92. Titer the sample as described in Step 20. The phage lysate titer should be $>10^9$ PFU·mL$^{-1}$.

Phage preparation can be stored at 4° C. for <6 months.

In alterative embodiments, exemplary methods as provided herein also comprise any one, several or all of the following steps for ultrafiltration, diafiltration, and concentration:

93. Assemble the peristaltic pump and CFF cassette as shown in FIG. 1.

94. Circulate 500 mL of sterile ddH$_2$O through the cassette and discard.

95. Place the intake and retentate hoses into the 0.2 μm sterile phage supernatant solution from Step 92.

96. Place the filtrate hose into a sink or waste container.

97. Recirculate (up to 1.5 L per batch) supernatant until ~200 mL remains.

98. Add 400 mL of sterile ddH$_2$O.

99. Recirculate supernatant until about 200 mL remains.

100. Add 400 mL of sterile TN buffer.

101. Recirculate supernatant until about 200 mL remains.

102. Repeat steps 100 and 101, until supernatant becomes clear and colorless.

103. Pause pump, place intake and retentate hoses in a sterile 50 mL conical tube, and recirculate while continuously adding remaining supernatant until 40 mL of concentrate remains ($1^{st}$ fraction).

104. Pause pump, place intake hose with retentate hose into a sterile 50 mL conical tube with 30 mL of TN buffer. Circulate briefly and remove intake hose. Collect 30 mL of concentrate ($2^{nd}$ fraction). Subsequent fractions can be collected if lower concentration phage stocks are desired.

105. Titer the sample as described in Step 20. The phage concentrate should be >10-fold higher in titer than that in Step 92.

Phage preparation can be stored at 4° C. for less than (<) 2 weeks.

In alterative embodiments, exemplary methods as provided herein also comprise any one, several or all of the following steps for density gradient ultrapurification: density gradient ultracentrifugation (Steps 106-111) and dialysis (Steps 112-120) may not be required to meet regulatory endotoxin safety limits of phage products[41]. Optionally, proceed to Step 135 for endotoxin quantification.

106. In an open top ultraclear (14×89 mm) round bottom tube, prepare a CsCl step density gradient by layering 2 mL of d=1.6, 3 mL of d=1.5, and 3 mL of d=1.3, from the bottom up. Avoid disturbing the previous density layer during preparation.

107. Fill the remaining tube volume with phage concentrate (about 4 mL) from Step 104.

108. Place tubes inside buckets and balance on a SW41 (or equivalent) rotor. Cool rotor to 4° C. and centrifuge with all buckets, even if unused.

109. Ultracentrifuge at 28,000×g for 4 h at 4° C.

110. Carefully extract tubes from buckets using tweezers.

111. With a concentrated light source, extract the visible band containing the phage particles by puncturing the thin-walled ultraclear tube with a 26G needle and syringe. CsCl concentrate dialysis, timing 1 d 112. Chill up to 3 L of sterile ddH$_2$O (4° C.) in a large beaker placed on a stir plate.

113. Place a magnetic stir bar in the beaker.

140. Clamp one end of the 100 k MWCO dialysis tubing and add the CsCl phage concentrate from Step 111.

115. Clamp the other end and secure the clamped dialysis tubing to a float.

116. Dialyze CsCl phage concentrate in the pre-chilled sterile ddH$_2$O and stir for 30 min at 4° C.

117. Exchange ddH$_2$O with up to 3 L of pre-chilled sterile storage buffer (for example PBS) and dialyze for 1 h.

118. Repeat step 117, but prolong dialysis to 24 h.

119. Recover phage concentrate.

120. Titer the sample as described in Step 20. The phage titer should be between $10^9$-$10^{12}$ PFU·mL$^{-1}$.

120. Phage preparation can be stored at 4° C. for <2 weeks.

LPS-Affinity Chromatography, Timing 2 h

Steps 121-134 are specific to the Pierce™ High Capacity Endotoxin Removal Spin Column.

121. Equilibrate and regenerate the spin column as per the manufacturer's instructions.

122. Place the spin column into a collection tube and centrifuge at 500×g for 1 min at RT to discard the regeneration solution.

123. Remove the cap and insert the bottom plug. Add 8 mL of 2M NaCl, replace the cap and invert the column several times.

124. Loosen the cap and remove the bottom plug. Place the column in a collection tube and centrifuge at 500×g for 1 min at RT to discard the solution.

125. Remove the cap and insert the bottom plug. Add 8 mL of supplied endotoxin-free H$_2$O. Replace the cap and invert the column several times.

126. Loosen the cap and remove the bottom plug. Place the column in a collection tube and centrifuge at 500×g for 1 min at RT to discard the water.

127. Remove the cap and insert the bottom plug. Add 8 mL of endotoxin-free PBS, replace the cap and invert the column several times.

128. Loosen the cap and remove the bottom plug. Place the column in a collection tube and centrifuge at 500×g for 1 min at RT to discard the PBS.

129. Repeat steps 127 and 128 two additional times.

130. Remove the cap and insert the bottom plug. Add 10 mL dialyzed phage concentrate from Step 119 to the resin, replace the cap and invert the column several times.

131. Incubate the column with gentle end-over-end mixing at 4° C. for 45 min.

132. Loosen the cap and remove the bottom plug. Place column in a sterile collection tube and centrifuge at 500×g for 1 min at RT to collect the sample.

133. Repeat steps 121-132 until all phage concentrate is processed.

134. Titer the sample as described in Step 20. The phage titer should be between $10^9$-$10^{12}$ PFU·mL$^{-1}$.

Phage preparation can be stored at 4° C. for less than (<) 6 months.

In alterative embodiments, exemplary methods as provided herein also comprise any one, several or all of the following steps for phage preparation and endotoxin quantification:

Steps 135-143 are specific to the Pierce™ LAL Chromogenic Endotoxin Quantitation Kit (or equivalent).

135. Equilibrate solutions to room temperature, as per the manufacturer recommendation.

136. Prepare LPS standards provided in the kit using "High Standards" option.

137. Add prepared standards, the blank, and samples from Step 133 to a 96 well microtiter plate. Appropriately dilute phage samples to be within the linear range of the high standard.

138. Warm plate to 37° C. and add 50 μL of LAL to each well. Tap plate lightly 10 times to mix.

139. Reconstitute the chromogenic substrate solution and warm it at 37° C., 5 min before use. Work quickly to prevent inactivation of solutions after reconstitution.

140. Add 100 μL of the chromogenic solution to each well.

141. At 6 min, add 50 μL of 25% (vol/vol) acetic acid to stop the reaction.

142. Immediately, measure $OD_{405nm}$ in a microplate reader.

143. Extrapolate the endotoxin level from the standard curve. Refer to Supplementary Table 1 for anticipated endotoxin concentration.

In alterative embodiments, exemplary methods as provided herein also comprise any one, several or all of the following steps for phage preparation protein analysis:

144. Determine the absorbance of phage preparations from Step 133 at 280 nm to measure protein level. This will vary between phage strains but should be between 1-3 mg·mL$^{-1}$.

145. Dilute phages to 15 μg in 20 μL of 1× Laemmli sample buffer.

146. Incubate samples at 90° C. for 5 min.

147. Centrifuge samples at 13,000 rpm for 60 sec at RT.

148. Prepare a 10% (wt/vol) acrylamide gel for SDS-PAGE electrophoresis.

149. Mount the gel into the tank, remove combs, and completely fill the inner chamber of the tank and ¾ of the outer chamber with 1×SDS-PAGE running buffer.

150. Pipette 3 μL of the standard and 20 μL of sample into the subsequent wells.

151. Run electrophoresis at 100V for about 60 min.

152. Wash the gel with ddH$_2$O 3 times for 15 min each.

153. Incubate the gel with 50 mL Coomassie blue staining solution at RT for 1 h.

154. Decant solution and add 50 mL ddH$_2$O. Incubate at RT for 30 min on a rocker.

150. Decant and repeat Step 154 three times.

156. Image the gel using a gel dock station or conventional camera.

In alterative embodiments, exemplary methods as provided herein also comprise any one, several or all of the following steps for determining phage preparation effects on human cell viability:

Steps 157-167 describe how to use the CellTiter-Glo® luminescent cell viability assay (Promega) to determine the number of viable cells in culture after phage preparation exposure based on quantitation of the ATP present, an indicator of cell proliferation and cytotoxicity.

157. In a 96-well tissue culture plate, seed wells with 100 μL of media containing about 20,000 of HeLa or HEK293 cells. Use a clear bottom white walled microplate to minimize well luminescence cross talk.

158. Incubate at 37° C., 5% CO$_2$, for 24 h.

159. The next day, check for a confluent monolayer of cell culture.

160. From Step 133, dilute phage stock to $10^8$ PFU·mL$^{-1}$ and $10^9$ PFU·mL$^{-1}$.

161. Add 10 μL of $10^8$ PFU·mL$^1$ stock for an approximate concentration of 1 cell: 100 phages, 10 μL of the $10^9$ PFU·mL$^1$ stock for a concentration of 1:1000 phages.

162. For positive control add 10 μL 1% (wt/vol) SDS and for negative control add 10 μL PBS. Ensure that two wells are filled with medium only.

163. Incubate at 37° C., 5% CO$_2$, for 24 h.

164. Equilibrate the 96-well plate to room temperature for 30 min before adding 100 μL CellTiter-Glo™ (or equivalent) to all wells.

165. Mix plate on an orbital shaker for 2 min to induce cell lysis.

166. Incubate at 22° C. for 10 min.

167. Measure luminescence on a microplate reader (see 'Anticipated results' below for example data).

In alternative embodiments, protocols as provided herein include additional non-FDA required safeguards, which can include additional checking of preparations by, for example, SDS-PAGE for bacterial proteins, and additional checking of cell culture viability, using for example a 'fast non in vivo test'.

In alternative embodiments, provided are compositions, a product of manufacture, a food, a drink, a nutraceutical, a formulation, a pharmaceutical or a pharmaceutical preparation comprising, or containing, or mixed with, or formulated with: a preparation of purified or substantially endotoxin-free bacteriophages as provided herein or a formulation or pharmaceutical composition as provided herein; for example, provided are compositions, a product of manufacture, a food, a drink, a nutraceutical, a formulation, a pharmaceutical or a pharmaceutical preparation comprising, or containing, or mixed with, or formulated with: a phage preparation having $10^9$ PFU, $10^{10}$ PFU, $10^{11}$ PFU, or $10^{12}$ PFU or more per unit dose and endotoxin levels below about 5.5 EU·mL$^{-1}$, or below about 5.0 EU·mL$^{-1}$.

In alternative embodiments, a composition, product of manufacture, food, drink, nutraceutical, formulation, pharmaceutical or pharmaceutical preparation as provided herein comprises, contains, or is manufactured as or formulated as or formulated at:

(a) a capsule, a tablet, a gel, a geltab, a liquid, a solid, an elixir, a spray, a powder, a suppository or an implant, a sachet, a lozenge, a freeze-dried composition, or an infant formula;

(b) a per dose, or per serving, or per unit dosage at, or a total daily dose of: between about 10(1) (or $10^1$) and 10(20) plaque-forming units (PFUs), or between about 10(3) and 10(17) PFUs, or between about 10(5) and 10(12) PFUs, or between about 10(7) and 10(9) PFUs, (c) administration in vivo; or for enteral or parenteral administration, or for ophthalmic, topical, oral, intra-venous (IV), intramuscular (IM), intrathecal, subcuta-neous (SC), intracerebral, epidural, intracranial or rec-tal administration, or by inhalation, or (d) a particle, a nanoparticle, a liposome, a tablet, a pill, a capsule, a gel, a geltab, a liquid, a powder, a suspen-sion, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product.

In alternative embodiments, a composition, product of manufacture, food, drink, nutraceutical, formulation, phar-maceutical or pharmaceutical preparation as provided herein, further comprises, or contains, or is mixed with, or formulated with:

a pharmaceutically acceptable excipient;

a flavoring or a sweetening agent, an aspartamine, a stevia, monk fruit, a sucralose, a saccharin, a cycla-mate, a xylitol, a vanilla, an artificial vanilla or choco-late or strawberry flavor, an artificial chocolate essence, or a mixture or combination thereof;

a preservative, a benzoic acid, a potassium sorbate;

at least one probiotic or prebiotic, wherein optionally the prebiotic comprises an inulin, lactulose, extracts of artichoke, chicory root, oats, barley, various legumes, garlic, kale, beans or flacks or an herb;

at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch;

at least one an anti-inflammatory agent, wherein option-ally the inflammatory agent comprises or is an NSAID, a 4 or a 5-amino-salicylate, an olsalazine, a mesalazine, a sulfasalazine and/or a balsalazide or an equivalent thereof or a combination thereof;

an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supple-ment, or a prebiotic nutrient;

and optionally the buffer or a buffering agent or the pharmaceutically acceptable excipient comprises an inorganic salt, a citric acid, a sodium chloride, a potas-sium chloride, a sodium sulfate, a potassium nitrate, a sodium phosphate monobasic, a sodium phosphate dibasic or combinations thereof;

and optionally the antacid comprises a calcium carbonate, a magnesium hydroxide, a magnesium oxide, a mag-nesium carbonate, an aluminum hydroxide, a sodium bicarbonate or a dihydroxyaluminum sodium carbon-ate; or any combination thereof.

In alternative embodiments, a composition, product of manufacture, food, drink, nutraceutical, formulation, phar-maceutical or pharmaceutical preparation as provided herein, further comprises, or is contained, or mixed with, or formulated with or as: a delayed or gradual enteric release composition or formulation, and optionally the formulation comprises a gastro-resistant coating designed to dissolve at a pH of 7 in the terminal ileum, optionally an active ingredient is coated with an acrylic based resin or equiva-lent, optionally a poly(meth)acrylate, optionally a meth-acrylic acid copolymer B or NF.

In alternative embodiments, bacteriophages in a compo-sition, product of manufacture, food, drink, nutraceutical, formulation, pharmaceutical or pharmaceutical preparation as provided herein, or purified using a method as provided herein, are from the order Caudovirales or Ligamenvirales; or from the family Myoviridae, Siphoviridae, Podoviridae, Lipothrixviridae, Rudiviridae, Ampullaviridae, Bicaudaviri-dae, Clavaviridae, Corticoviridae, Cystoviridae, Fuselloviri-dae, Globuloviridae, Guttaviridaelnoviridae, Leviviridae, Microviridae, Plasmaviridae; or a combination thereof.

Products of Manufacture and Kits

Provided are products of manufacture and kits for prac-ticing methods as provided herein; and optionally, products of manufacture and kits can further comprise instructions for practicing methods as provided herein. In alternative embodiments, provided are kits containing preparations of bacteriophage comprising about $10^9$ PFU, $10^{10}$ PFU, $10^{11}$ PFU, or $10^{12}$ PFU or more per unit dose and endotoxin levels below about 5.5 $EU \cdot mL^{-1}$, or below about 5.0 $EU \cdot mL^{-1}$.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Exemplary Protocols

This example demonstrates that exemplary methods (protocols) for isolating bacteriophage.

This exemplary method is an experimentally validated protocol that is modular and adaptable, and ensures the identity, titer, quality, and purity of human and animal phage products and prevent instances of contamination, mix-ups, deviations, and errors.

Plaque Assay Phage Isolation

Plaque assays are routinely used to discover new phage strains from a wide range of sources such as sewage, bodies of water, liquefied soil, and bodily fluids. We use a modified agarose overlay technique described previously[18] where a filtered natural sample is serially diluted and poured over a lawn of exponentially growing compatible bacteria. As the bacterial lawn grows, small zones of lysis become visible. Each plaque forming unit (PFU) is derived from an initial infection with a single virion followed by phage-induced lysis of neighboring cells[18]. PFUs displaying different morphologies (for example FIG. 2a) are selected to inoculate small-scale liquid cultivation on the compatible bacteria. A critical factor in the isolation of highly functional phages is the preparation of a pure solution of identical phages. Therefore, the PFU selection process is repeated several times until all plaques exhibit a similar morphology, suggesting a single phage strain has been isolated.

Phage Titration

Agar Petri plating techniques are used routinely to quantify phage particle numbers in preparations. One option is to use the agarose overlay technique as previously described[18], which consists of mixing serially diluted phage samples with susceptible bacteria in molten agar and pouring over solid agar in a Petri plate. A more rapid option is to perform a series of tenfold dilutions of a phage stock in a microplate, and spot dilution samples on a bacterial seeded agar Petri plate (FIG. 3j).

Liter-Scaled Shake Flask Cultivation

Figure 2C:
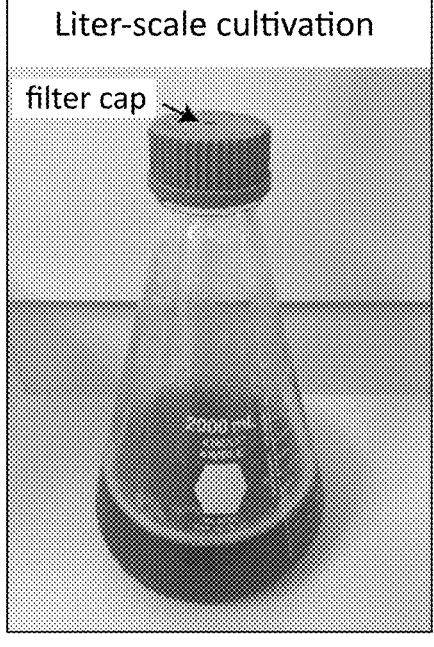
Figure 2D:
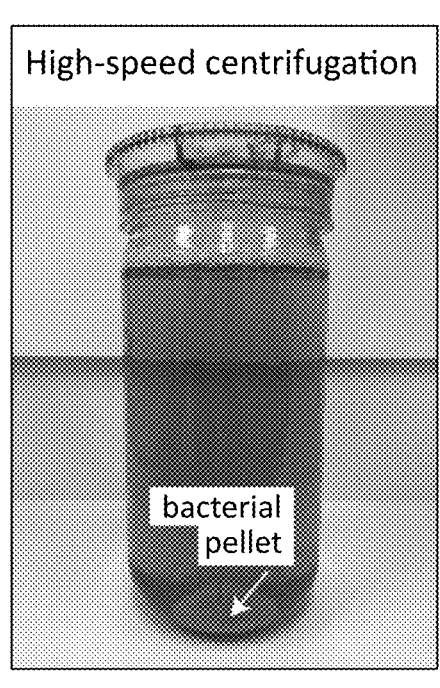
Figure 2E:
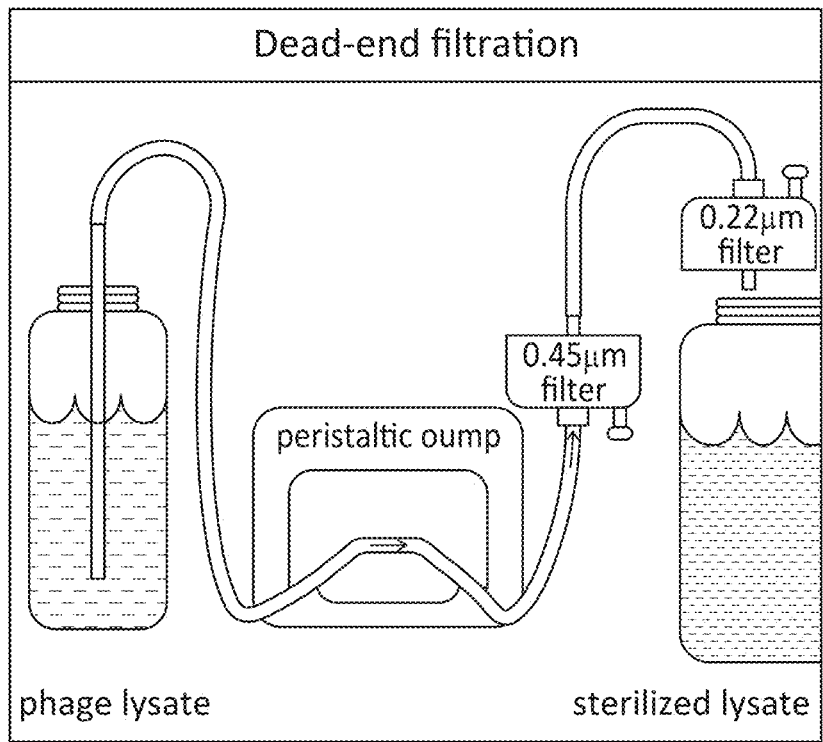

Enrichment of identical phages is prepared through infection of a compatible bacterial host. Test tube and smaller shake flask cultivation in complex medium on a rotary shaker are convenient for initial phage cultivation for bacterial susceptibility testing and DNA isolation. Large shake batch cultures in complex medium on a rotary shaker are required for downstream process sterilization of cultivated phages (FIG. 2g-i). Phage enrichment by shaking flask cultivation can be scaled to produce several liters per batch; limited only by the high-speed centrifuge rotor bottle capacity. Seeding cultures with a multiplicity of infection (MOI) of between 0.01-0.1 can produce phage lysates with about $10^9$ to $10^{10}$ PFU·mL$^{-1}$. Although, mid-log stage of bacterial growth is the most amenable to infection by most phages[70], basic parameters for specific bacteria-phage interaction can be optimized for higher phage yield. For example, selected complex medium and temperature for the bacterium are factors that influence the infectivity of phages and burst size.

Membrane Applications in Phage Production

We use two flow configurations for membrane filtration processes, namely dead-end microfiltration and cross-flow ultrafiltration (CFF). These filtration modes are illustrated in FIG. 3. We use dead-end microfiltration for both the reduction of bioburden in phage lysates and between processing steps, as it has high product recovery, low cost, and simple operation. The direction of the fluid flow is perpendicular to the membrane surface. Accordingly, the retained bacterial cells and particulate are collected on the membrane surface forming a filtration cake. This layer then makes additional filtration effects, improving the separation efficiency. Dead-end filtration is a batch-type process, with extensive membrane fouling being its main disadvantage.

We employ several methods to minimize membrane fouling while filtering phage lysates. First, we avoid the bacterial cell wall disruption with chloroform to reduce bacterial debris of uninfected phage-resistant cells, which typically develop with prolonged culturing. Moreover, chloroform can harm certain phages[28]. Second, we subject phage lysates to two rounds of high-speed centrifugation with a sterile bottle change in between. Third, we use a pleated cartridge filter design, which provides a higher surface area. Lastly, two pleated cartridge filters are used for two-step membrane pore sizing (FIGS. 2e and 3a).

Figure 2F:
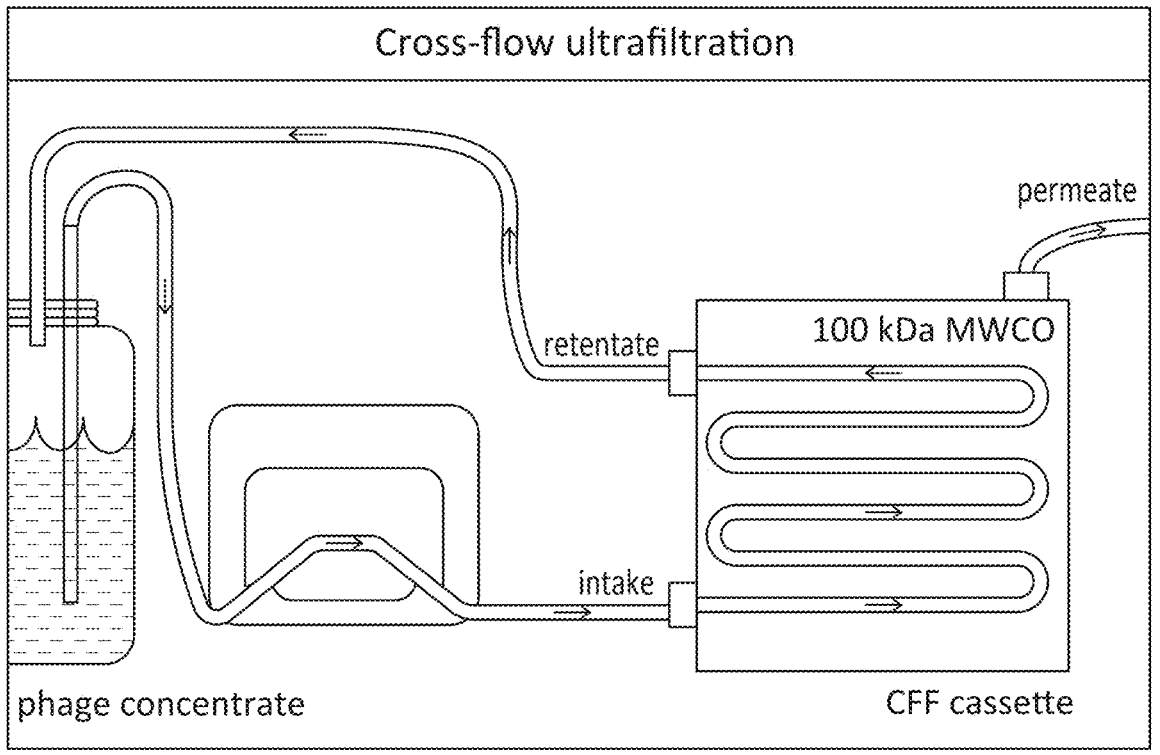
Figure 2G:
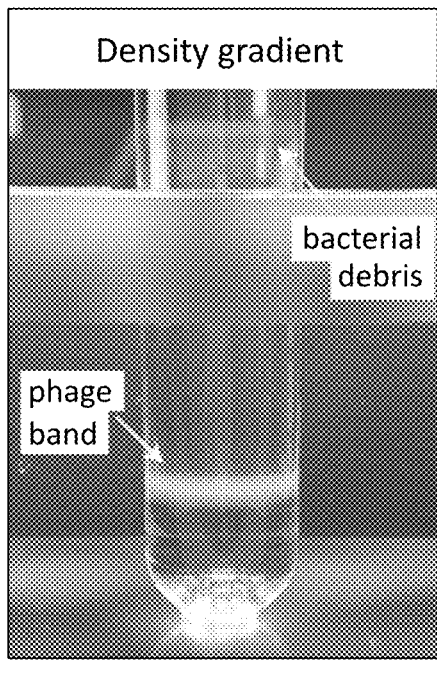
Figure 2H:
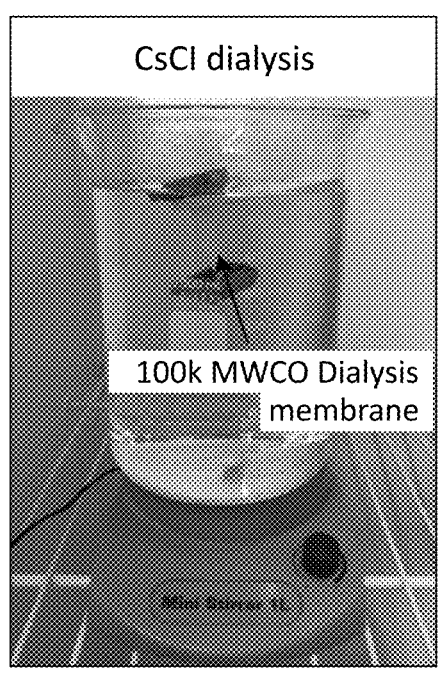
Figure 2I:
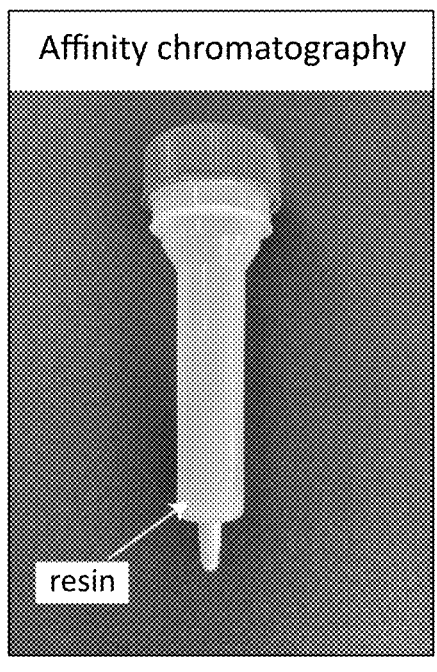
Figure 2J:
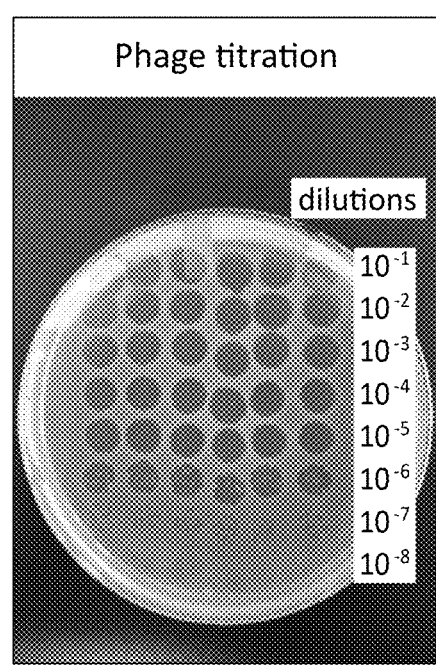

Next, we use the Vivaflow™ CFF cassette as an efficient way to ultrafilter lysates with a high concentration of phages (FIGS. 2f and 3b). CFF works by introducing dead-end filtered lysate under pressure across the membrane surface, instead of directly onto the micro-filter. During filtration, any material smaller than the cross-flow membrane pore passes through the membrane, while larger phage particles remain in the retentate stream. CFF with a 100 kDa membrane pore size can theoretically remove both free endotoxin, which are approximately 10 kDa in size, and all known exotoxins, which are typically smaller than 30 kDa[41]. Moreover, a membrane pore size of 100 kDa provides an equivalent to a spherical particle with a 3 nm diameter and is therefore sufficient to retain most known phages[71]. We employ diafiltration with freshly autoclaved buffer to increase the purity and improve the separation of phages from bacterial debris and the complex growth medium. Simultaneously, permeate is withdrawn at the same rate that the buffer is added and so the gross impurities are washed out of the phage product solution. Thus, CFF is used to "wash" the phage particles while rapidly concentrating up to 2 liters by a factor of 30 with per CFF cassette.

For further cost reduction, cartridge filters can be flushed to remove membrane pore blockage for reuse after autoclaving. In addition, the Vivaflow™ cassettes can be cleaned and re-used several times.

Upscale of the Purification Process Using Density Gradient Ultracentrifugation

Density gradient ultracentrifugation developed by Brakke[72] is a common technique used to isolate and purify a wide range of phages purely on the basis of their density[27, 33]. We perform a self-forming density gradient isopyknic ultracentrifugal separation technique making use of differences in density between gross impurities and viruses of a CFF phage preparation (FIG. 2g). In self-forming gradients, the phage solution is layered on top of the gradient medium, centrifuged, and as the solute molecules sediment to form the gradient identical phages band at their isopyknic points. Following ultracentrifugation, virus bands may be visualized as a result of their light scattering. We employ this technique for accomplishing both removal of other unwanted phage strains and gross impurities. That is, different phages will be separated by their different densities during ultracentrifugation[11]. In addition, large bacterial debris aggregates will remain near the top of the gradient, while microsolutes will pass to the bottom of the gradient.

We then use dialysis to facilitate the removal of unwanted CsCl from phage particles in solution by selective and passive diffusion through a semi-permeable membrane (FIG. 2h). As mentioned, phage particles are larger than the 100 kDa membrane-pores, while CsCl and buffer salts pass freely through the membrane, reducing the concentration of those molecules in the phage preparation. Dialysis also accomplishes further removal of bacterial microsolutes (for example LPS molecules) and storage buffer exchange for phage products, but dilutes the phage preparation.

Chromatographic Removal of Endotoxins

Endotoxin removal is critical when producing therapeutic phages in bacterial systems. We further removed this hydrophobic molecule through commercial purification affinity chromatography (FIG. 2i), which is likely the most reliable and widely applied method used to remove endotoxin. We then used the Limulus amoebocyte lysate (LAL) assay because of its sensitivity, reproducibility, and simplicity for endotoxin detection; which uses the blood coagulation system of the horseshoe crab, and clots upon exposure to endotoxin[74].

Limitations of our GLMP Phage Preparations

A drawback with our protocol, like with most phage purification techniques, is the loss of phages scaled with an increase in manipulation techniques. For instance, we found reductions in phage yield after dialysis and affinity chromatography. Dialysis may lead to phage loss due to osmotic shock. Indeed, phages tend to be less sensitive to environmental osmotic pressure changes. However, ultracentrifugation can injure phage particles due to high gravitational force[31], which are then likely to be more susceptible to osmotic changes. Affinity chromatography commonly leads to significant phage loss, and we propose that these losses are dependent on how strongly phages associate with free LPS in the preparation. The overall degree of loss is dependent on the specific phage:bacteria interactions.

Another drawback is the potential health risk of using cesium for density gradient ultracentrifugation. Although, radioactive cesium can cause seizure, syncope, hypokalemia, and chronic diarrhea[75], non-radioactive cesium is readily found in the body, mostly derived from consumption of plant and animal products[76]. Our protocol includes phages retrieved in 1500 mg·mL⁻¹ CsCl, followed by 1:1000 dialysis against phage storage buffer. This implies only trace amounts of cesium would remain in phage preparations.

Future pharmaceutical demand for phage products necessitates scalable GLMP phage production processes. Our GLMP phage production protocol was optimized for laboratory-scale performance, the principles of exemplary protocol as provided herein are compatible with other existing bioprocess methods used in the manufacture of biotherapeutics. For example, in alternative embodiments, cultivation of phages in large bioreactors offers scalability over the use of shake-flasks[77]. Bioreactor enrichment of phages can be compatible with our downstream filtration steps that are scalable to industrial processes.

Reliance on centrifugation can have scalability limitations. However, many bulk drugs and biological products are produced through centrifugation. For example, purification of insulin and separation of blood cells are separated through the process of centrifugation.

Lastly, affinity chromatography is not ideal for high throughput process. Although the basis of many endotoxin removal techniques is the structure of endotoxin complexes themselves (hydrophobic, hydrophilic, and charge), most methods often fall short of industrial manufacturing controls. We found that our upstream processes, including the scalable CFF, remove the bulk of endotoxins to satisfy regulations.

Materials

Reagents

Prepare all solutions and regents with sterile deionized water, unless otherwise indicated. Tryptone (Fisher, cat. no. BP1421-2)

Yeast Extract (Fisher, cat. no. BP1422-2)

Sodium chloride (NaCl; Fisher, cat. no. 7647-14-5)

Agar (CulGenes, cat. no. C6002)

Phosphate buffer saline (BioPioneer, cat. no. MB1001)

Tris base (Fisher, cat. no. 77-86-1)

Ethanol, 200 proof (Millipore Sigma, cat. no. E7023-500 ml)

DNA Extraction Reagents:

Glycine (Millipore Sigma, cat. no. G4392)

SDS (Fisher Scientific, cat. no. BP166-500)

Nanobind CBB Big DNA Kit (Circulomics, cat. no. NB-900-001-01)

DNase I (Life Technologies, cat. no. 90083)

RNase A (Life Technologies, cat. no. EN0531)

PEG-8000 (Fisher Scientific, cat. no. BP233-100)

Magnesium sulfate heptahydrate (MgSO4; Fisher Scientific, cat. no. M63-500)

Acetic acid (Fisher Scientific, cat. no. A38S 500)

Equipment

Biosafety cabinet (ESCO, cat. no. AC2-459-NS)

Microtiter plate reader (BMG, model: Clariostar, cat no. 0430-100)

Vortex mixer (VWR, cat. no. 12620-838)

Spectrophotometer (Denovix, model. no. DS-11 FX+)

High-speed Centrifuge (Beckman Coulter, model: Avanti JXN-26 IVD, cat. no. B38623)

Fixed-angle centrifuge rotor for 1 L (Beckman Coulter, model: JLA-8.1000, cat. no. 969328)

Ultracentrifuge (Beckmann Coulter, Optima-L-90K, cat. no. 365672)

SW41 rotor (Beckman Coulter, cat. no. 331336)

Microcentrifuge (Sartorius, cat. no. A-14C)

Bunsen burner (VWR, model no. 89038-530)

Multichannel pipette (8×10 µl; Sartorius, cat. no. UX-24505-44)

Single Channel Pipets: 1,000, 200, 20 and 10 µL; Sartorius, cat. no. UX-24505-33, -34, -35 and -36, respectively.

Electronic pipette controller (Argos, model: OmegaZen, cat. No. 25300-96)

10 L water bath (Cole Parmer, cat no. WE-14576-08)

Peristaltic pump (Cole Parmer, model: Masterflex, cat. no. EW-07522-20)

Pump head (Cole Parmer, cat. No. EW-77253-00)

Tubing (Thermo Scientific, cat. no. 8060-3015; Cole-Parmer, cat. no. ZX-06422-01)

Microbiological incubator/shaker (Eppendorf, model: S44i, cat. no. S44I200005)

Incubator (VWR, model: 5420, cat. no. 97005-252)

Cell incubator (Eppendorf, model: C170i, cat. no. 6731010015)

Hemocytometer (Hauser Scientific, cat. no. 3110V)

Thermomixer (Eppendorf, cat. no. 2231000574)

Stir plate (Heathrow, cat. no. HP8885794)

Water Purification System (Millipore, cat. no. ZRXQ010T0)

Consumables

Autoclave glassware and tubing to degrade phage particles before use.

10 cm petri plate (Fisher Scientific, cat. no. 08-757-100D)

1.7 mL microcentrifuge tubes (Sorenson, cat. no. 11500)

2.0 mL microcentrifuge tubes (Sorenson, cat. no. 12030)

Glass test tubes (VWR, cat. no. 10545-922)

Glass 2 L Erlenmeyer flasks with GL-45 screw-cap (Kimble-Chase, cat. no 26720-2000)

GL45 0.22 µm PTFE membrane vented cap (Corning cat. no. 1395-45LTMC)

1 L centrifuge bottles (Beckman Coulter, cat. no. A98812)

0.8/0.45 µm and 0.45/0.22 µm capsule filters (Sartorius, model: Sartopore 2, cat. no. 5441306G5, 5441307H5)

100 kDa Cross-flow ultrafiltration cassette (Sartorius, model: Vivaflow 50R, cat. no. VF20P4; and Vivaflow 200™, 100,000 MWCO PES Item no.: VF20P4

Ultraclear Tubes (14×89 mm) (Beckman Coulter, cat. no. 344059)

Luer-Lok™ syringe (5 ml; BD, cat. no. 309628)

0.45 and 0.22 µm syringe filters (Sartorius, cat. no. 16537, 16541)

0.22 µm GL45 filter caps (Sartorius, cat. no. 16541-k)

26 G needle (BD, cat. no. 305111)

15 and 50 mL conical centrifuge tubes (VWR, cat. no. 430790 and 430828)

2 L glass beaker (VWR, cat. no. 10754-760)

Dialysis membrane tubing, 100 kDA MWCO (Spectra/Por, cat. no. 131408)

96-well clear microplate (Corning, cat no. 35177)

96-well white microplate (Greiner bio-one, cat no. 655088)

PCR eight-tube strips and caps (Sarstedt, cat. no. 772.991.1002)

T75 culture flask (Corning, cat. no. 430639)

MinION™ flow cell (Oxford Nanopore, cat. no. R9.4.1)

Kimtech™ wipes (Fisher Scientific, cat. no. 06-666)

Gloves (Xceed™, cat. no. XC-310-S, M, L)

Pierce High Capacity Endotoxin Removal Spin Columns, 1 mL (ThermoFisher Scientific, cat. no. 88277)

Strains and Cell Lines

Authenticity and purity of strains and cell lines needs to be verified regularly.

PAK_P1 Phage (GenBank accession no. KC862297.1)

PAK_P5 Phage (GenBank accession no. KC862301.1)

PYO2 Phage (GenBank accession no. MF490236)

E217_A65 Phage (GenBank accession no. MF490240)

*Pseudomonas aeruginosa* strain PAO1 (ATCC no. 47085)

*Pseudomonas aeruginosa* strain PAK[78]

*Serratia marcescens* strain

*Klebsiella oxytoca* strain

Reagent Set-Up

Prepare all solutions with sterile double distilled water (ddH$_2$O).

Liquid Growth Medium Mix 10 g tryptone, 5 g yeast extract, and 5 g NaCl in 1 L of ultrapure ddH$_2$O. Autoclave and store at 22° C.

Solid Growth Medium Add 14 g of agar to growth medium and autoclave. Then, cool to 55° C. in a water bath for 30 min to 1 hour (h). Sterilely pour solid growth medium into sterile petri plates. Thickness should be approximately 5-10 mm thick. Let cool for at 22° C. for 8 hours (h) Store at 4° C.

Molten soft-agar Mix 7 g of agar to growth medium and autoclave. Then, cool to 55° C. in a water bath to prevent agar solidification before plating.

Tris-sodium chloride (TN) buffer Mix 10 mM Tris (pH 7.0) and 150 mM NaCl. Adjust to pH 7.0. Autoclave and store at 4° C.

Tris-EDTA (TE) Buffer Mix 10 mM Tris (pH 7.0) and 1 mM EDTA (pH 8.0). Adjust to pH 7.5 and store at 22° C.

10×SDS-PAGE Running Buffer Mix 30.0 g of Tris base, 144.0 g of glycine, and 10.0 g of sodium dodecyl sulfate (SDS) in 1 L of ddH$_2$O. Store at 22° C.

Cesium Chloride Solutions Mix 41.2 g (d=1.6), 34.13 g (d=1.5) or 20.49 g (d=1.3) in 50 mL of TN buffer. Sterile filter and store at 22° C.

Resuspension buffer (5 mM MgSO$_4$). Add 0.0123 g of MgSO$_4$ heptahydrate per 10 mL ddH$_2$O.

Procedure

Complete all steps under a sterile environment, for example under flame sterilization or in a biosafety cabinet.

Sourcing and Isolating Phage Strains

Timing: 3-5 d.

1| To isolate phage strains de novo, centrifuge aqueous environmental samples at 8,000×g for 30 min to remove bulk debris.

2| Decant the environmental sample without disturbing debris pellet.

3| 0.2 µm syringe filter sample.

4| In a sterile test tube, mix 100 µL of bacterial host at ° Da) 0.2 and 100 µL of filtered sample.

5| Add 3 mL of molten soft-agar, mix gently, and pour over solidified agar petri plate. If the bacterial lawn is clear after incubation, dilute the environmental sample to obtain single plaques.

6| Incubate under appropriate temperature and atmospheric growth conditions until plaques form on a confluent lawn of bacteria.

7| Using a Pasteur pipette, select plaques displaying different morphologies and re-suspend separately in 100 μL of PBS in a microcentrifuge tube.

8| Prepare serial dilutions for each plaque isolated.

9| In sterile test tubes, mix 10 μL of the dilutions with 500 μL of bacteria grown to ° Dam 0.2.

10| Add 3 mL of molten soft-agar to each, mix gently, and pour over solidified agar petri plate.

11| Incubate under appropriate temperature and atmospheric growth conditions until plaques are visible on a confluent lawn of bacteria.

Repeat steps 7 through 10 until each phage stock exhibits only a single plaque morphology.

Phage Titration

Timing: 6-18 h

Phage titer can be determined by either (12a) plaque assay, or (12b) spot plaque assay.

12a| Agar Overlay Tittering
  i. Serially dilute the phage stock in microcentrifuge tubes by tenfold in PBS.
  ii. In sterile test tubes, mix 10 μL of each serial dilution with 100 μL of bacteria grown to $OD_{600}$ 0.2.
  iii. Add 3 mL of molten soft-agar, mix gently, and pour over solidified agar petri plate.
  iv. Incubate under appropriate temperature and atmospheric growth conditions until plaques form on a confluent lawn of bacteria.
  v. Determine phage stock concentration as $PFU \cdot mL^{-1}$.

12b| Spot Plaque Titering
  i. Dry growth agar petri plate for 30 min in a biosafety cabinet.
  ii. To seed a lawn of bacteria, pour 3 mL of bacteria grown to $OD_{600}$ 0.2 onto the dry growth agar petri plate and quickly remove excess culture.
  iii. Dry in a biosafety cabinet for 15 min.
  iv. While drying, add 90 μL of PBS to 8 wells row-by-row in a 96-well microtiter plate.
  v. Add 10 μL of phage sample to the first well, mix well.
  vi. Pipette 10 μL from the $1^{st}$ well into the $2^{nd}$ well, mix well.
  vii. Repeat step vi between the remaining wells to create a dilution series ($10^{-1}$ to $10^{-8}$).
  viii. Using an 8-channel pipette, spot 4 μL from each well onto a dried seeded lawn of bacteria prepared in (i-iii).
  ix. Incubate plate at appropriate temperature and atmospheric growth conditions until plaques form on a confluent lawn of bacteria.
  x. Determine phage stock concentration as $PFU \cdot mL^{-1}$.

Small-Scale Cultivation

Timing: 18-24 h

13| Warm 50 mL of growth medium in a sterile 250 mL GL45 screw-top flask with a GL45 0.22 μm PTFE membrane vented cap.

14| Add 500 μL of bacteria grown to $OD_{600}$ 0.2 and incubate at appropriate temperature and atmospheric growth conditions for 20 min.

15| Add phage at a multiplicity of infection (MOI) of between 0.01 to 0.1 and incubate under appropriate bacterial growth conditions.

16| To remove bulk bacterial debris, transfer lysates to 50 mL conical centrifuge tubes and centrifuge at 6,000×g for 30 min.

17| Filter sterilize the supernatant with a 0.2 μm syringe filter into a sterile 50 mL conical tube. Do not disturb the pellet during decanting.

18| Titer and stored at 4° C.

Liter-Scale Shake Flask Cultivation

Timing: 24-30 h

Large phage production batches are limited by rotor capacity (for example, 6 L per BeckmanCoulter Avanti high-speed centrifugation). This protocol is for processing 6×1 L cultures in parallel.

64| In a sterile 2 L GL45 screw-top flask with a GL45 0.22 μm PTFE membrane vented cap, warm 1 L of complex growth medium (FIG. 2c).

65| Add 5 mL of bacteria grown to $OD_{600}$ 0.2 and incubate appropriate temperature and atmospheric growth conditions for 20 min.

66| Add phage a MOI of between 0.01 to 0.1 and incubate under appropriate bacterial growth conditions until outgrowth of phage insensitive/resistant cells are initially visible as medium haziness/cloudy appearance (or $OD_{600}$ greater than (>) 0.1) in the flask; and optionally, at that point, cool culture for example to about 4° C. or between about 4° C. to 30° C., or cool to below 37° C., and continue culturing to maximize phage production and minimize phage insensitive/resistant cell growth.

67| To remove bulk bacterial debris, transfer lysates to 1 L centrifuge bottles and centrifuge at 8,000×g for 45 min (see FIG. 2D).

68| Decant lysates into fresh, sterile 1 L centrifuge bottles without disturbing the bacterial pellet.

69| Repeat step 21.

70| Decant supernatant into sterile 1 L glass bottle.

71| Assemble 0.8/0.45 μm and 0.45/0.2 μm capsule filters inline as shown in FIG. 2e. Use the peristaltic pump to filter sterilized supernatant into a sterile glass bottles.

72| Titer and store at 4° C.

Ultrafiltration, Diafiltration, and Concentration

Timing: 2-4 h

73| Assemble the peristaltic pump and CFF cassette as shown in FIG. 2f

74| Circulate 500 mL of sterile $ddH_2O$ through the cassette and discard.

75| Place the intake and retentate hoses into the 0.2 μm sterile phage supernatant solution.

76| Place the filtrate hose into a sink or waste container.

77| Recirculate (processing up to a total of 1.5 L) supernatant until approximately 200 mL remains.

78| Add 400 mL of sterile $ddH_2O$.

79| Recirculate supernatant until approximately 200 mL remains.

80| Add 400 mL of sterile TN buffer.

81| Recirculate supernatant until approximately 200 mL remains.

82| Repeat steps 34 and 35, until supernatant becomes clear and colorless.

83| Pause pump, place intake and retentate hose in a sterile 50 mL conical tube, and recirculate while continuously adding remaining supernatant until 40 mL of concentrate remains ($1^{st}$ fraction).

84| Pause pump, place intake hose with retentate hose into a sterile 50 mL conical tube with 30 mL of TN buffer. Circulate briefly and remove intake hose. Collect 30 mL of concentrate ($2^{nd}$ fraction). Subsequent fractions can be collected if lower concentration phage stocks are also desired.

85| Titer and store at 4° C.

Density Gradient Ultrapurification

Timing: 4-28 h

86| In an open top ultraclear round bottom tube, 14×89 mm, prepare a CsCl step density gradient by layering 2 mL of d=1.6, 3 mL of d=1.5, and 3 mL of d=1.3, from the bottom up.

87| Fill the remaining tube volume with phage concentrate (~4 mL).

88| Place tubes inside buckets and balance on a SW41 rotor.

89| Ultracentrifuge at 28,000×g for 4 h at 4° C.

90| Carefully extract tubes from buckets using tweezers.

91| With a concentrated light source, extract the visible band containing the phage particles by puncturing the thin-walled ultraclear tube with a 26G needle and syringe (FIG. 2g).

If multiple bands are formed, repeat steps 40-44, but with 7 mL of d=1.5 and ultracentrifugation at 38,000×g for 18 h at 4° C.

CsCl Concentrate Dialysis

Timing: 1 d

92| Chill up to 3 L of sterile ddH$_2$O in a large beaker placed on a stir plate.

93| Place a magnetic stir bar in the beaker.

94| Clamp one end of the 100 k MWCO dialysis tubing and add CsCl phage concentrate.

95| Clamp other end and secure the tubing to a floaty.

96| Dialyze CsCl phage concentrate in the pre-chilled sterile ddH$_2$O and stir for 30 min (FIG. 2h).

97| Exchange ddH$_2$O with up to 3 L of pre-chilled sterile storage buffer (for example PBS) and dialyze for 1 h.

98| Repeat step 51, but prolong dialysis for 24 h.

99| Recover phage concentrate, titer, and store at 4° C.

LPS-Affinity Chromatography

Timing: 2 h

This protocol is specific to the Pierce™ High Capacity Endotoxin Removal Spin Column (FIG. 2I) (and equivalent protocols can be used). Briefly:

100| Equilibrate and regenerate the spin column as per the manufacturer's instructions.

101| Place the spin column into a collection tube and centrifuge at 500×g for 1 min to discard the regeneration solution.

102| Remove the cap and insert the bottom plug. Add 8 mL of 2M NaCl, replace the cap and invert the column several times.

103| Loosen the cap and remove the bottom plug. Place the column in a collection tube and centrifuge at 500×g for 1 min to discard the solution.

104| Remove the cap and insert the bottom plug. Add 8 mL of supplied endotoxin-free H$_2$O. Replace the cap and invert the column several times.

105| Loosen the cap and remove the bottom plug. Place the column in a collection tube and centrifuge at 500×g for 1 min to discard the water.

106| Remove the cap and insert the bottom plug. Add 8 mL of endotoxin-free PBS, replace the cap and invert the column several times.

107| Loosen the cap and remove the bottom plug. Place the column in a collection tube and centrifuge at 500×g for 1 min to discard the PBS.

108| Repeat steps 60 and 61 two additional times.

109| Remove the cap and insert the bottom plug. Add 10 mL dialyzed phage concentrate to the resin, replace the cap and invert the column several times.

110| Incubate the column with gentle end-over-end mixing at 4° C. for 45 min.

111| Loosen the cap and remove the bottom plug. Place column in a sterile collection tube and centrifuge at 500×g for 1 min to collect the sample.

112| Repeat steps 56-65 until all phage concentrate is processed.

113| Titer sample and store at 4° C.

Endotoxin Quantification

Timing: 2 h

In alternative embodiments, optionally, for endotoxin removal, this protocol is specific to the Pierce™ LAL Chromogenic Endotoxin Quantitation Kit (and equivalent protocols can be used). Briefly:

114 Equilibrate solutions to room temperature, as per the manufacturer recommendation.

115 Prepare LPS standards using "High Standards" protocol.

116 Add standards, blank, and samples to a 96 well microtiter plate. Appropriately dilute phage samples to be within the linear range of the high standard.

117 Warm plate to 37° C. and add 50 μL of LAL to each well. Tap plate lightly 10 times to mix.

118 Reconstitute the chromogenic substrate solution and warm it at 37° C., 5 min before use.

119 Add 100 μL of the chromogenic solution to each well.

120 At 6 min, add 50 μL of 25% acetic acid to stop the reaction.

121 Immediately, measure OD$_{405nm}$ in a microplate reader.

122 Endotoxin level is extrapolated from the standard curve.

Timing:

Steps 1-11, sourcing and isolating phage strains: 3-5 d

Step 12, phage titration: 6-18 h

Steps 13-18, small-scale cultivation: 18-24 h

Steps 64-72, large-scale cultivation: 24-30 h

Steps 73-85, ultrafiltration, diafiltration, and concentration: 2-4 h

Steps 86-91, density gradient ultrapurification: 4-28 h

Steps 92-99, CsCl concentrate dialysis: 24 h

Steps 100-113, LPS-affinity chromatography: 2 h

Steps 114-122, endotoxin quantification: 2 h

Steps Need Renumbering

Results

Process Optimization at Liter-Scale Production

Figure 4:
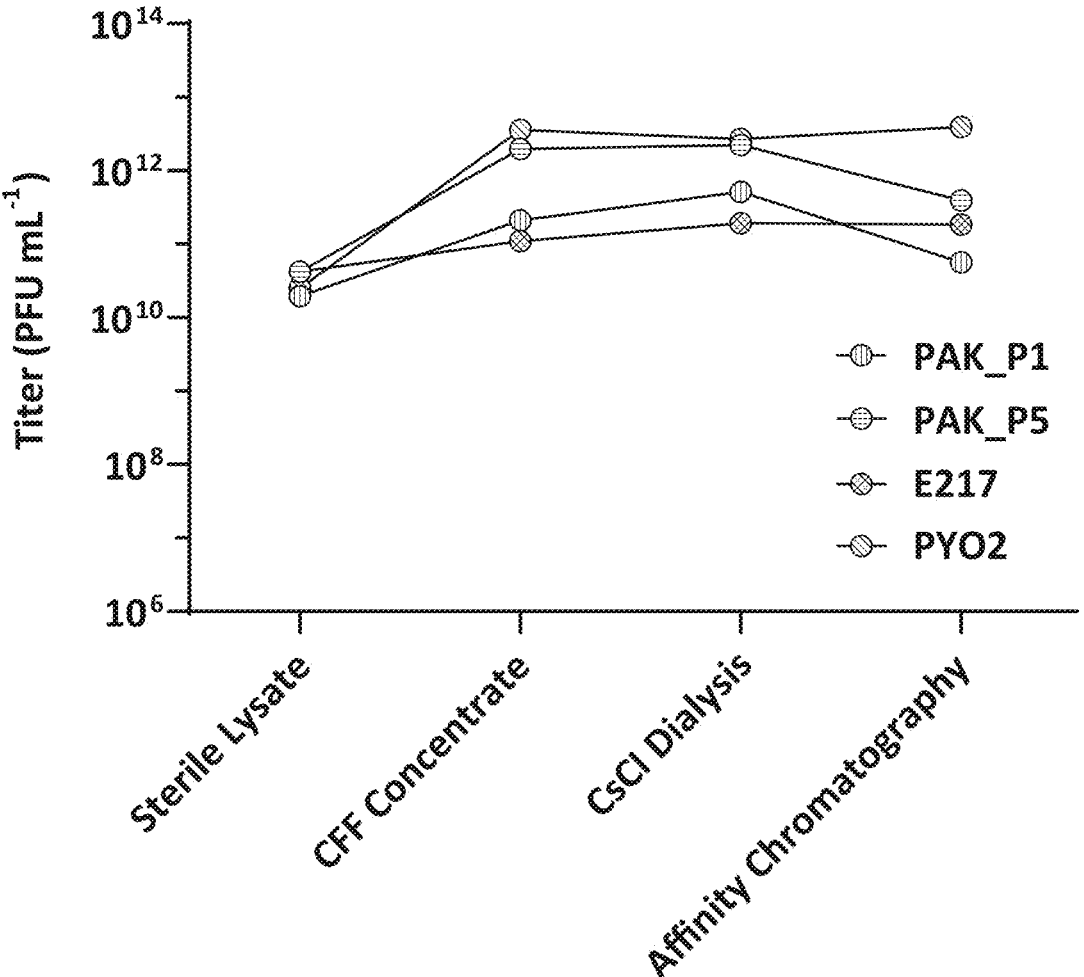
FIG. 4 graphically illustrates the *Pseudomonas* phage strain titer after each purification step in the exemplary protocol of Example 1. Phages were titrated using the spot plaque assay and plaques counted after 18 h.

Exemplary GLMP protocols as provided herein employ a combination of modified classical techniques, modern membrane filtration processes, and omission of certain common practices (FIG. 2). We found that six-liter shake-flask cultivation yielded approximately 30 mL of final phage product that contained a mean $10^{11}$ PFU·mL$^{-1}$ (FIG. 4 and FIG. 7, Table 2). Importantly, downstream processes maintained a relatively high phage titer, while reducing endotoxins to below 5.5 EU·mL$^{-1}$ (FIG. 5 and FIG. 7, Table 2). With these final values, a single production run produces at least 300 treatment doses at $10^9$ PFU, a commonly prescribed IV dose[1]. Because final phage products contained very low endotoxin levels, theoretically it is possible that treatments of up to $10^{12}$ PFU could be prescribed to humans, and be within regulatory limits of 5 EU·kg$^{-1}$ h$^{-1}$ [40]. In comparison, Belgium is the only western country that routinely produces phages in a laboratory under prescription, as a "magistral" preparation (i.e. drug compounding)[38]. To the best of our knowledge, magistral phage products are typically purified by lysate high-speed centrifugation and subsequent affinity chromatography endotoxin removal. In practice, this approach yields approximately $10^7$ PFU·ml$^{-1}$ and endotoxins of 12.5 EU·ml$^{-1}$ [39]. A recent extended access phage therapy reported PEG/NaCl, density gradient ultracentrifugation and dialysis purification of *Mycobacterium* phages yielded to a comparably high $10^{11}$ PFU·ml$^{-1}$ and undetectable endotoxin (because they are not produced by Mycobacteria)[2]. Although Mycobacteria do not produce endotoxins, PEG-CsCl-dialysis can adequately reduce LPS to <0.05 EU·ml$^{-1}$ experimentally, it does so at the expense of phage yield[21].

Figures 5A, 5B, 5C, 5D, 5E, 5F, 5G:
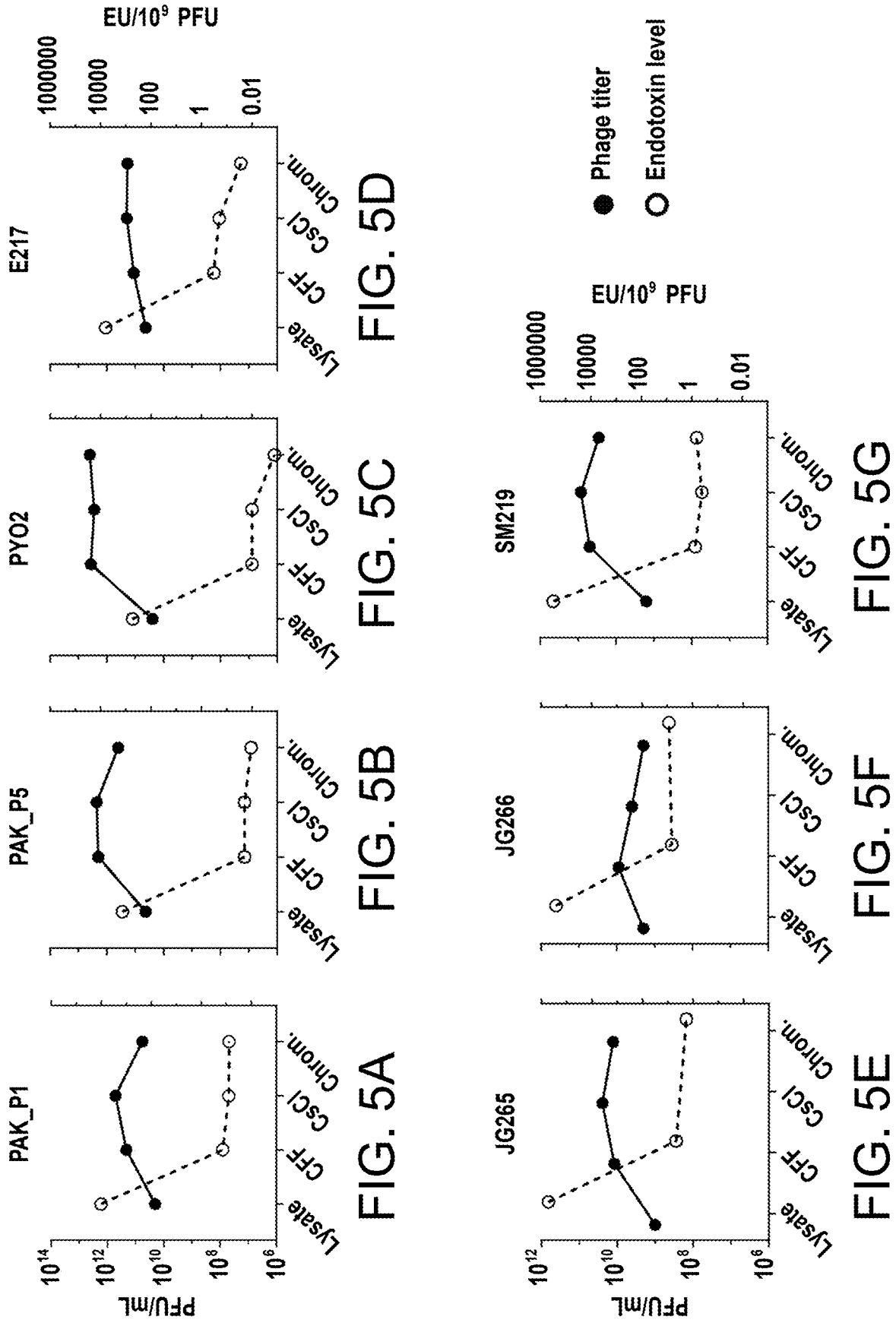
FIG. 5A-G graphically illustrates phage strain titer and normalized endotoxin concentration: Phage titers (PFU $mL^{-1}$) were measured by spot plaque titering after each purification step (black circles); Limulus amoebocyte lysate chromogenic endotoxin quantitation (EU) was measured at $OD_{405}$ after each purification step (white circles), endotoxin concentration was normalized against a phage therapeutic titer ($10^9$ PFU $mL^{-1}$)

High titer and low endotoxin phage preparation was shown to be independent of the bacterial host strain, phage strain, and viral structure. Phages PAK_P1 and PAK_P5 were isolated from French wastewater with the *P. aeruginosa* strain PAK[82], while phages E217 and PYO2 were isolated from Italian wastewater with the *P. aeruginosa* strain PAO1[23]. Phages PAK_P1, PAK_P5, and E217 are myoviruses with a long contractile tail, while PYO2 is a podovirus with a short noncontractile tail[23,82]. By contrast, other practiced laboratory phage cultivation and purification approaches, such as polyethylene glycol precipitation, centrifugal ultrafiltration, organic solvent extraction, enzymatic inactivation, and anion-exchange chromatography were previously shown to be phage and bacterial strain dependent[11,18,26-34]. Although these techniques can produce equally high phage concentrations, they often retain high amounts of endotoxins. Our protocol focuses on removing LPS early with double centrifugation, direct washing, microfiltration, and cross-flow ultrafiltration, which reduces endotoxin to below 40 EU·mL$^{-1}$ (FIG. 5*a*). We found the subsequent CsCl density gradient ultracentrifugation purification step led to, in some preparations, 8-30% increase in endotoxin concentration. Our results conflict with the recent study by Van Belleghem et al., which compared several phage cultivation and endotoxin removal methods[33]. The study concluded that CsCl density gradient ultracentrifugation was the most effective at removing endotoxin but at the expense of up to a 100-fold loss in phage titer[33]. Exemplary protocols can use a smaller fraction withdrawal (visible band only) from the density gradient tube, which concentrates both the phage sample and endotoxin (FIG. 2*g*).

Our results demonstrate that after cross-flow ultrafiltration with a MWCO 100 kDa pore size, and in combination with several buffer washes, endotoxin levels are already within regulatory limits for human use. The semi-automated CFF is a pressure-driven membrane filtration process that was able to concentrate phages >10-fold, reduce endotoxin by 4000-fold, and buffer exchange, in a single-step (FIGS. 4 and 5*a*). Other studies have similarly shown CFF to be an effective phage concentration technique[31,32]. Exemplary techniques as provided herein markedly decrease labor and improve purification reproducibility, and the use of lower MWCOs tends to concentrate endotoxins along with the phage particles[31]. The recent "Phage On Tap" purification protocol showed that centrifugal ultrafiltration offers a more rapid phage concentration and buffer exchange method, but is ineffective at reducing endotoxins[32]. It is important to note that most exotoxins are smaller than 100 kDa[41]. Nonetheless, endotoxins in CFF samples can be further reduced by affinity chromatography (data not shown).

Example 2: Exemplary Protocols for Isolating and Purifying Bacteriophage

In this Example we outline an exemplary systematic, comprehensive, and practicable procedure for phage isolation, selection, liter-scale cultivation, concentration and purification. This exemplary protocol utilizes aspects to demonstrate product identity, purity, and quality while protecting scientific data integrity for batch therapeutics. This production process utilizes typical microbiology laboratory equipment and no organic solvents. The method yields sufficient phages for most expanded access eIND and potentially for clinical phase I/II applications. We show phage preparations obtained using this protocol have high phage purity measured by Limulus amoebocyte lysate (LAL) chromogenic assays, protein analysis, and cell viability analyses. All executed runs of this exemplary procedure were successful, vouching reproducibility of this protocol.

In recent years, the demand for small quantities of phages for expanded access eIND and clinical phase I/II trials has been growing. Small aliquots of phages are useful for animal experiments and pilot studies in which high-titer and high-purity are required. For this purpose, we developed a liter-scale phage production process. This exemplary production method is able to deliver high-titer phages ($10^9$-$10^{12}$ plaque forming units (PFU)) with low endotoxin (4.3-24.1 units) per milliliter (Table 3, or FIG. 11). We are currently in the process of using final patient formulations in expanded access eIND phage therapy.

In alternative embodiments, the production method provided herein has three major advantages: 1) It does not require specialized production equipment, like a bioreactor or chromatography system, 2) By using a cross flow filtration (CFF) method to concentrate phages (Steps 93-105) and exchange growth medium, no organic solvents are required, 3) Filtration materials are disposable, avoiding any cleaning validation, which saves additional time and costs. Therefore, this protocol provides a standard-of-production for medicinal phages, allowing expanded access phage therapy, to reach more of those in need, starting by increasing the global production of safe personalized phage products.

Recently, phages have been shown to play important roles in health through unexpected host immune interactions[21,25,35,36]. However, immunological response studies have used varying degrees of purified phages, ranging from sterile filtered lysates to low endotoxin preparations in saline buffer[25,37,38] Although, there is no evidence of direct toxicity induced by phage particles, study of mammalian cell-phage interaction requires phage preparations to be free of bacterial cells, toxins and other compounds to avoid skewing host responses. Due to the high-titer and purity of phage production, it is suitable for cell culture and animal studies.

We have used this exemplary protocol for the production of four *Pseudomonas* phages PAK_P1, PAK_P5, E217 and PYO2, two *Klebsiella* phages JG265 and JG266, and a *Serratia* phage SM219 (Table 3, or FIG. 11, and Supplementary Table 1). Although the selection criteria of therapeutic phages is still under investigation[7,9,25], this exemplary production method can be generally used for other Gram-negative phage and final formulation designs.

In alternative embodiments, this exemplary phage production protocol offers several distinct advantages over currently practiced methods conducted at laboratory scales. Table 3 shows that a six-liter production run can produce between $6.0 \times 10^{10}$-$6.4 \times 10^{13}$ phage virions in total, providing between 58 to 64,0000 doses at $10^9$ PFU; a commonly prescribed intravenous treatment dose[1,2,39]. In addition, endotoxin measured by LAL chromogenic analysis ranged between 0.0003-0.03 EU (endotoxin units) per $10^9$ PFU dose (Table 3, or FIG. 11). In comparison, phages prepared under prescription as "magistral preparations" for human treatment in Belgium[40] and for expanded access eINDs by Chan et al[39] were reported to yield about 10[7] PFU·ml[−1] at greater than (>) 10 EU·ml[−1]. Because our phage preparations are of higher titer and purity than those reported as being administered to patients for expanded access phage therapy, implementation of our protocol would conceivably allow for administration of higher phage titer per treatment dose and maintain a FDA human intravenous limit of less than (<5) EU·kg[−1] h[−1] [41].

Figure 8:
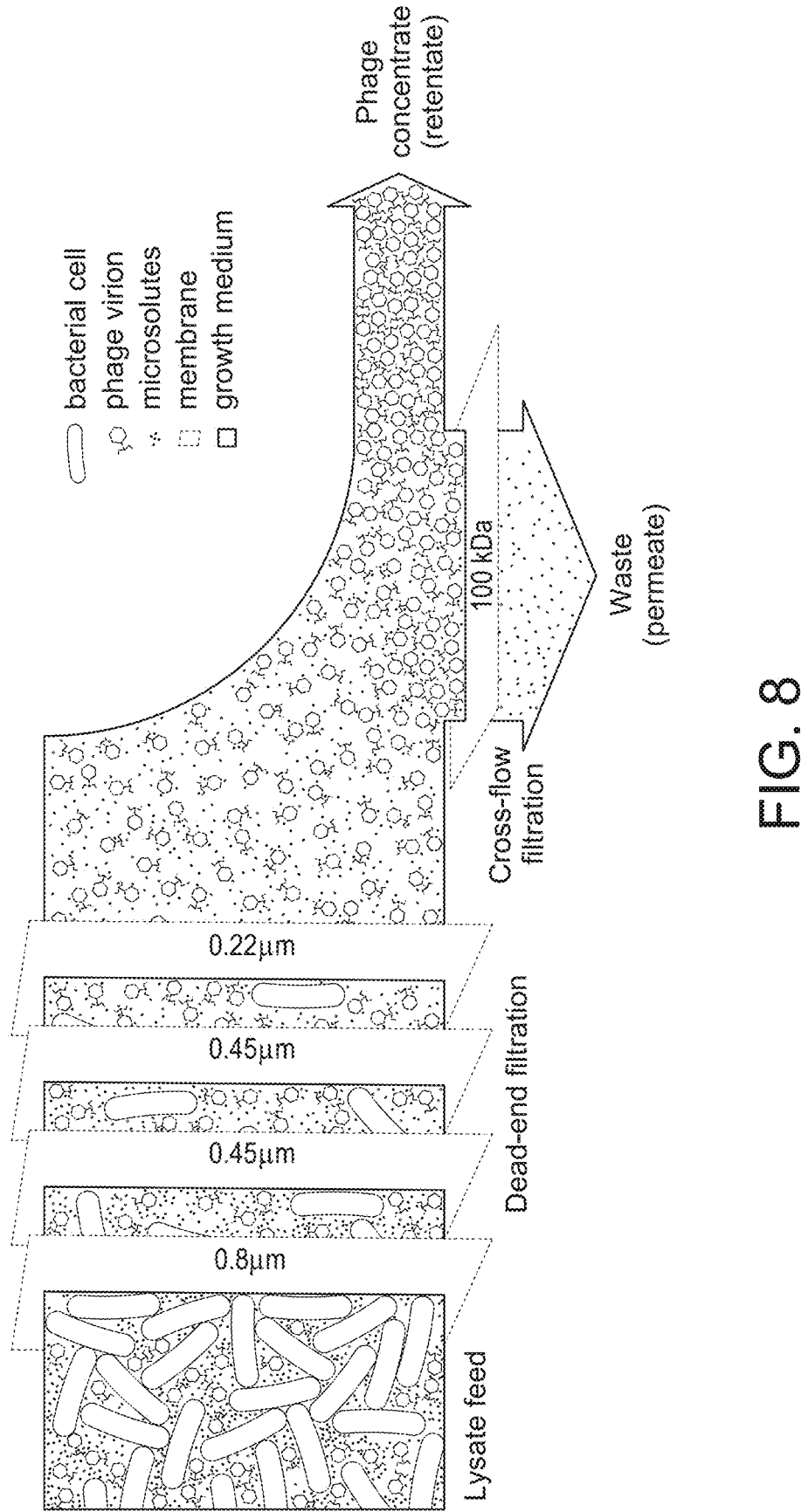
FIG. 8 illustrates a schematic of phage lysate dead-end filtration (see for example, step 91 in Example 2) and cross-flow filtration (see for example, steps 93 to 104, in Example 2) removal of impurities; phage lysates are sterilized by inline 0.8, 0.45, 0.45 and 0.22 μm membrane filtration to remove whole bacterial cells and cellular debris; then cross-flow filtration (CFF) is used to remove growth medium and microsolutes smaller than 100 kda (for example, endotoxin, peptidoglycan, exotoxins, flagella, nucleic acids, etc.), while concentrating the phages in phosphate buffer.
Figure 10A:
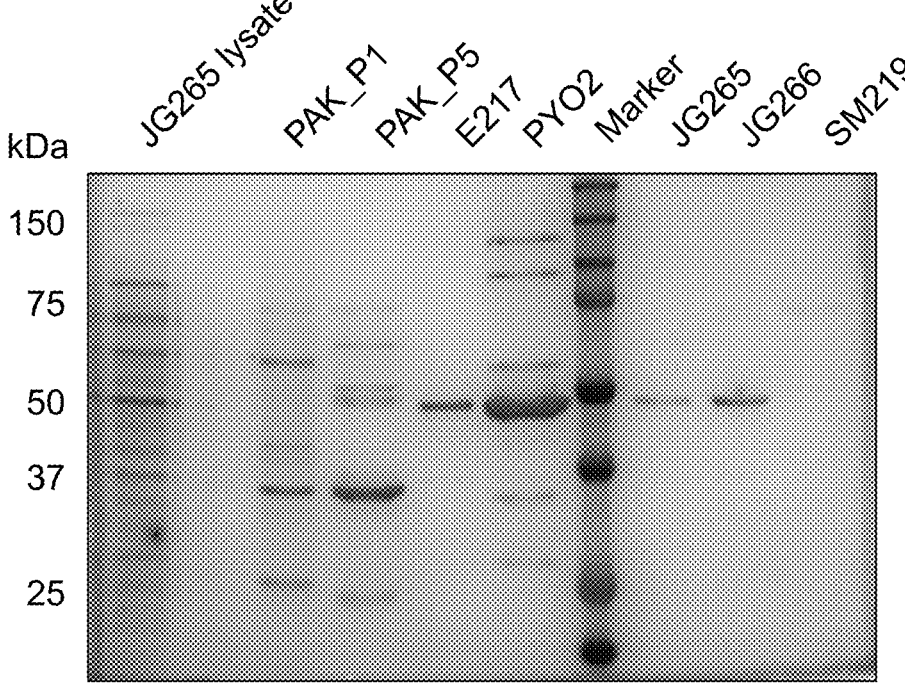
FIG. 10A-G illustrate purity and safety analyses of final phage preparations.
Figure 10B:
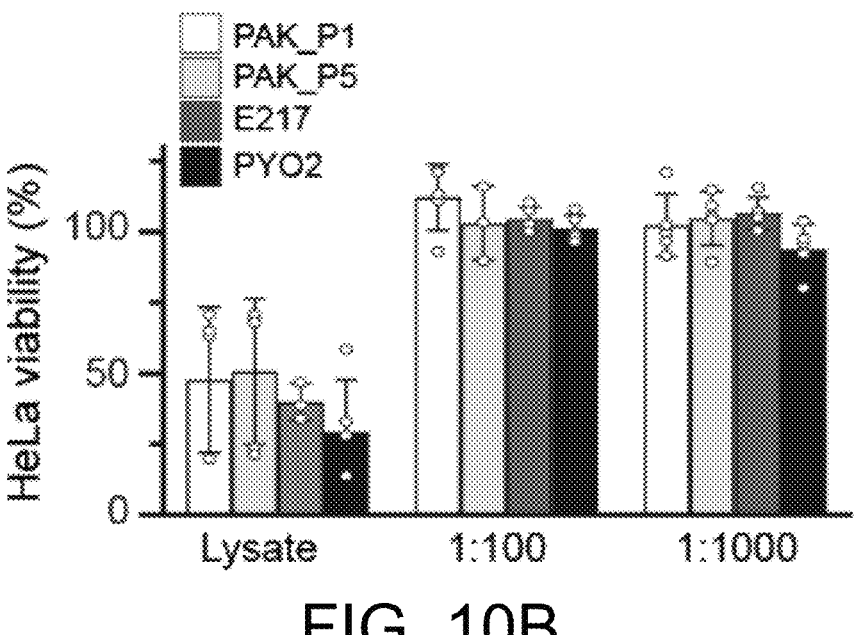
Figure 10C:
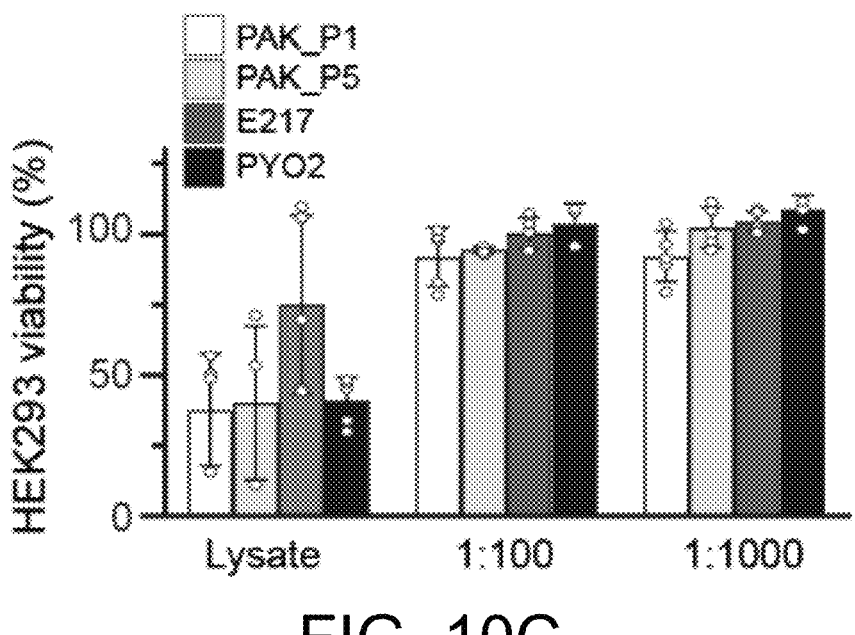
Figure 10D:
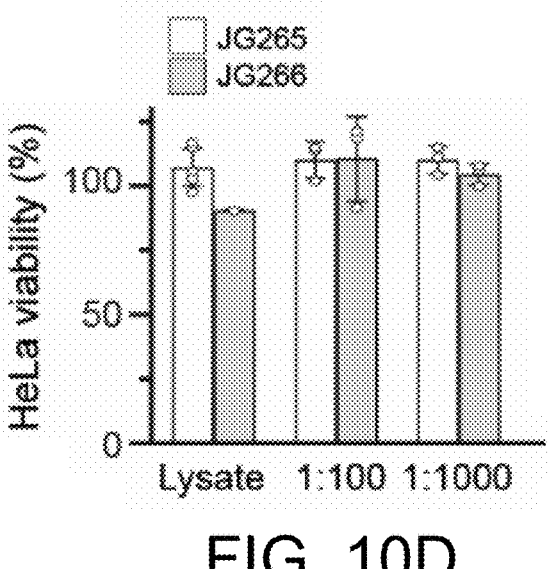
Figure 10E:
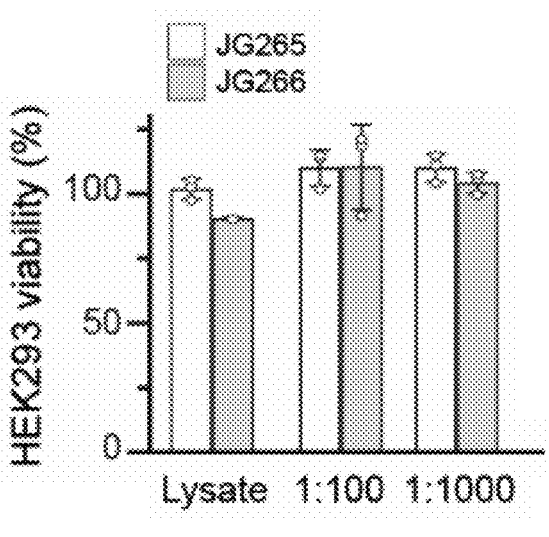
Figure 10F:
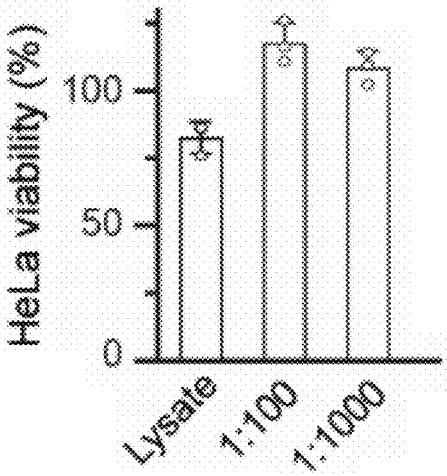
Figure 10G:
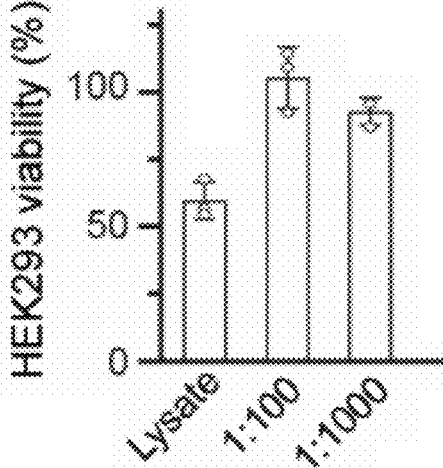

In contrast to the polyethylene glycol (PEG) precipitation method conducted in the majority of competing protocols (for example[9,32]), the CFF method employed here (Steps 93-105) is a pressure-driven scalable membrane filtration process that markedly decreases labor and improves purification reproducibility (FIG. 8). PEG precipitation methods can produce comparably high phage yields[2,21]. However, high yields are phage strain dependent[31,32,34] and PEG precipitation does not effectively remove endotoxin[21]. Therefore, PEG precipitated phages typically require substantial dilution or implementation of other endotoxin removal techniques. CFF is able to reliably fractionate phages from gross bacterial impurities (for example <40 EU·ml[−1]) and diafilter and concentrate phage particles 4-100 fold (FIG. 9). Importantly, this all occurs in a cost-effective, programmed and semi-automated single-step. CFF was shown to be highly effective at concentrating phages[32]. The use of a CFF molecular weight cut-off (MWCO) of 100 kDa in combination with several sterile washes appear to be important for the significant removal of endotoxin from phage lysates because CFF using MWCO <30 kDa has been shown to concentrate endotoxin along with phages[32]. In addition, CFF with MWCO of 100 kDa would potentially remove exotoxins, which all have been found to be smaller than 100 kDa[42]. Together, the inclusion of CFF is a cost-efficient way to concentrate and purify phages. It is also scalable with no barrier to running several apparatuses with additional hardware (not described in this protocol).

The downstream cesium chloride (CsCl) density gradient ultracentrifugation (Steps 106-111), dialysis (Steps 112-120), and affinity chromatography (Steps 123-134) processes may not be required to meet FDA drug product endotoxin safety limits[41]. Without including these steps, our approach yields ~30 mL of between 2.7×10[11] to 1.1×10[14] phage virions in total per six-liter batch post CFF (Supplementary Table 1). This provides an estimated 270-110,000 doses at 10[9] PFU with <0.22 EU; the allowable endotoxin exposure for a 70 kg person would be 350 EU h[−1]. Omission of lengthy and costly density gradient ultracentrifugation, dialysis, and affinity chromatography steps would reduce phage preparation time to approximately five days. However, if time permits, CsCl density gradient ultracentrifugation, dialysis, and affinity chromatography offer further separation of potential gross impurities and provide a strategy to avoid unwanted phage contaminants[11,34] Density gradient ultracentrifugation can offer visual confirmation that preparations are homogeneous containing a single phage strain because unwanted contaminating phages appear as a second band due to their differing density.

Our protocol avoids the use of chloroform, denaturing solvents and detergents. Competing protocols often recommend using chloroform to disrupt the bacterial cell wall to release internal phage particles in lysates or as standard procedure to remove PEG after precipitating phages[43]. There are risks with adding chloroform in the purification process such as denaturing certain phages[18,29]. Long-term exposure to chloroform by inhalation in humans has resulted in hepatitis, jaundice, and central nervous system effects and it has been shown to be carcinogenic in animals after oral exposure, resulting in kidney and liver tumors[44]. In our experience, chloroform also increases the amount of bacterial cell debris by lysing phage resistant cells—which harbor no phage particles—that can emerge with extended bacterial culturing. Organic solvents and detergents can be an effective method to reduce endotoxins in phage lysates[33,34,45]. However, they can be toxic to users, inhibit chromogenic-based endotoxin quantification methods and decrease phage stability in storage[34].

Lastly, we use Oxford Nanopore MinION sequencing over other sequencing technologies due to several added benefits. The MinION offers rapid generation of sequence information, with the reads being generated and available for study within minutes after initiation of the run. Importantly, the latest generation of the MinION sequencer (cat. no. SQK-RAD004), in our recent experience with phage genomics, allows a few reads to cover the whole genome. Furthermore, the assembly of the sequences generated are nearly identical to the Illumina assembled sequences, in our case by only a single base. Finally, the Oxford Nanopore sequencing is significantly cheaper than other sequencing technologies, with a FLONGLE™ (flow cell dongle) generating over 1 GB of sequence data, more than sufficient to accurately assemble a phage genome.

We have used the exemplary production method for the cultivation and purification of phages that infect Gram-negative bacteria including *Pseudomonas aeruginosa, Klebsiella oxytoca* and *Serratia marcescens* grown aerobically at 37° C. Pathogenic strains of *Pseudomonas aeruginosa* and *Klebsiella*, along with Gram-negative *Escherichia coli* and *Acinetobacter*, according to the CDC, are becoming increasingly resistant to most available antibiotics[15]. Therefore, the case studies presented here are relevant for current expanded access eIND phage therapy global needs. Notwithstanding, the individual culture conditions for each bacterium-phage pair, there should be minor optimization needed to use this protocol for the production of a variety of phages. For instance, larger volumes of low-titer phage lysates can be processed with CFF to obtain a sufficiently high titer sample for downstream procedures. Nonetheless, further validation of this protocol with other phages such as those that infect Gram-positives or anaerobes is needed.

In alternative embodiments, a possible drawback, as with most purification techniques, is the loss of phages with increased number of manipulation techniques. For instance, we found phage yield decreases significantly after LPS-affinity chromatography, which appear to be phage strain dependent. For example, *Pseudomonas* phage PAK_P1 and PAK_P5 use LPS as its bacterial cell wall binding site. We found PAK_P1 and PAK_P5 titers each decreased from 5.19×10[11] to 5.78×10[10] and 2.30×10[12] to 4.00×10[11] PFU·mL[−1], respectively (Supplementary Table 1). In contrast, the titers pre- and post-affinity chromatography remained stable for the other phages tested. We propose that the losses for some phage strains are dependent on how strongly phages associate with the remaining LPS in samples prior to affinity chromatography.

There might be a health risk of using CsCl. Our protocol includes phages retrieved in 1500 mg·mL−1 CsCl, followed by 1:1000 dialysis against phosphate buffer saline (PBS) and high-titer aliquots diluted in sterile saline to the required therapeutic phage dose. This suggests that treatments may contain trace amounts of cesium (<80 ng·mL[−1]). Although, radioactive cesium can cause seizure, syncope, hypokalemia, and chronic diarrhea[46], non-radioactive cesium is readily found in the human body, mostly derived from consumption of plant and animal products[47].

The scalability of the presented phage production process is unclear. The principles of this exemplary protocol are compatible with other existing bioprocess methods used in the manufacture of biotherapeutics. For example, cultivation of phages in bioreactors would offer scalability over the use of shake-flasks[48], while still being compatible with presented downstream filtration steps that are easily scalable with larger filters. Centrifugation steps however can have scalability limitations and affinity chromatography is not ideal for high throughput processes.

Experimental Design

This exemplary protocol outlines a combination of classical and modern viral cultivation and purification techniques, which are experimentally validated for Gram-negative phages. This exemplary protocol's design is modular and adaptable, allowing each laboratory to decide how to best implement the necessary controls, by using scientifically sound design, and testing procedures to achieve higher quality through continual improvement. Implementing this formal system will ensure the identity, titer, quality, and purity of human and animal phage products and prevent instances of contamination, mix-ups, deviations, and errors.

Plaque Assay Phage Isolation

Plaque assays are routinely used to discover new phage strains from a wide range of sources such as sewage, bodies of water, liquefied soil, and bodily fluids. We use a modified agarose overlay technique, described previously[18], where a filtered natural sample is serially diluted and poured over a lawn of exponentially growing compatible bacteria (Steps 1-12). As the bacterial lawn grows, small zones of lysis become visible. Each PFU is derived from an initial infection with a single virion followed by phage-induced lysis of neighboring cells[18]. PFUs displaying different morphologies are selected to inoculate small-scale liquid cultivation on the compatible bacteria. A critical factor in the isolation of highly functional phages is the preparation of a pure solution of identical phages. Therefore, the PFU selection process is repeated several times until all plaques exhibit a similar morphology, suggesting a single phage strain has been isolated.

Phage Titration

Agar Petri plating techniques are routinely used to quantify phage particle numbers in preparations. One option is to use the agarose overlay technique as previously described[18], which consists of mixing serially diluted phage samples with susceptible bacteria in molten agar and pouring over solid agar in a Petri plate (Step 20 Option A). A more rapid option is to perform several tenfold serial dilutions of a phage stock in a microplate and spot these dilutions on a bacterial seeded agar Petri plate (Step 20 Option B; FIG. 1). Conventional plaque titering can also be substituted or supplemented by the use of real-time quantitative PCR (qPCR) if primers for the phage strain are available[49,50].

Annotation and Bioinformatic Analysis of Phage Genomes

The primary goals of genome sequencing and analysis (Steps 57-83) are different when the phages are required for human therapeutic applications than when they are used for research purposes. For phages that will be used for expanded access phage therapy, the primary goal of sequencing and annotation is to ensure that no harm is likely to be introduced by the phage preparation, and the primary concern is the transfer of genetic material between bacteria by transduction. Prophages directly influence the microbes where they reside: they often express genes that are beneficial to the bacteria (called lysogenic conversion factors)[51]. There are three elements that are the primary concern for transfer: 1) toxins, 2) antibiotic resistance genes, and 3) virulence factors. The toxins associated with cholera[52], diphtheria[53], scarlet fever[54], shigella[55-57], and botulinum[58] are all encoded by phages integrated into their host bacterial genome[59,60]. Were one of those toxins to be transferred by a phage used for expanded access phage therapy, the expression of the toxin may lead to increased morbidity and mortality[57]. Similarly, the introduction of antibiotic resistance genes either already on the phage genomes[61] or transferred between bacterial hosts by specialized or generalized transduction[62] may render traditional antibiotic therapies ineffective. Although the precise role of phages in the spread of antibiotic resistance genes between bacteria is somewhat controversial[63], it has been demonstrated previously[64,65]. Moreover, the relative ease of antibiotic resistance gene(s) identification warrants analysis. In addition to antibiotic resistance genes and toxins, phages are also implicated in the horizontal transfer of virulence genes[66].

Computational analysis of toxins, antibiotic resistance, and bacterial virulence factors present their own challenges. Novel toxins and mechanisms of virulence are continually being discovered[67]. This limits understanding of the mechanisms of disease and our ability to predict the detrimental effect of horizontal gene transfer. The identification of genes that provide direct antibiotic resistance mechanisms is straightforward, however the identification of resistant alleles of housekeeping genes is more complex. For example, it is trivial to identify a $\beta$-lactamase encoding gene, but associating specific point mutations with resistance is more computationally challenging without thousands of genomes[68]. Multiple databases can be used to identify toxins, antibiotic resistance alleles, and virulence factors. For example, Abricate (https://github.com/tseemann/abricate) uses ensemble methods to compare sequences to the most up-to-date databases including the Comprehensive Antibiotic Resistance Database (CARD)[69], ResFinder[70], NCBI's AMRFinder[71], Antibiotic Resistance Gene-ANNOTation (ARG-ANNOT)[72], the virulence factor database[73], and PlasmidFinder[74].

In expanded access phage therapy, care must be taken to avoid temperate phages that are able to lysogenize their bacterial host. While there are genetic approaches to inactivate the lysogenic lifecycle[2], it is preferable to begin with phages that are unable to lysogenize their host. Phage genome sequencing allows rapid confirmation of whether a phage is likely to be temperate or virulent. Whole-genome sequencing may also provide clues to other biological contaminants in the preparation, depending on the abundance of the contaminants relative to the phage. However, in each of these considerations, phage genome sequencing will only identify known features. Computational identification of a toxin, antibiotic resistance gene, or virulence factor should not infer that these elements are not present, rather than known elements are not present.

The Oxford Nanopore MinION sequencer is the most convenient "long-read" sequencer currently on the market, and sequencing phages with this device often results in a single read representing the entire phage[75]. After sequence assembly, the genomes are explored for antibiotic resistance genes and virulence factors (for example with the aforementioned Abricate) and by annotating with PATRIC[76]. PHACTS is used to determine whether the phages are likely to be virulent or temperate[77]. Phages without genes of concern and that are predicted to be virulent (i.e. strictly lytic lifecycle) are selected for downstream liter-scale cultivation.

Finally, the approach described in this protocol is appropriate for the rapid analysis of phage genomes for expanded access therapy. As we focus on those characteristics of the phage however, further techniques should be applied to the phage and its genome for full characterization[78-80].

Liter-Scaled Shake Flask Cultivation

Test tube and smaller shake flask cultivation in complex medium on a rotary shaker are convenient for initial phage cultivation for bacterial susceptibility testing and DNA isolation. Large shake batch cultures in complex medium on a rotary shaker are required for downstream process sterilization of cultivated phages (FIG. 1). Phage enrichment by shaking flask cultivation can be scaled to produce six liters per batch, limited here by centrifuge rotor capacity. Seeding cultures with a multiplicity of infection (MOI) of 0.1 can produce phage lysates with about $10^9$ to $10^{10}$ PFU·mL$^{-1}$. Although, mid-log stage of bacterial growth is the most amenable to infection by most phages[81], basic parameters for bacteria-phage interaction should be optimized. For example, selected complex medium and temperature for the bacterium are factors that influence the infectivity of phages and burst size.

Membrane Applications in Phage Production

We use two flow configurations for membrane processes, namely dead-end microfiltration (Steps 91-92) and cross-flow ultrafiltration (Steps 93-105; illustrated in FIG. 2). Dead-end microfiltration is used to retain both bacterial cells and particulates that are collected on the membrane surface forming a filtration cake. This layer then makes additional filtration effects, improving the separation efficiency. Dead-end filtration is usually a batch-type process, with extensive membrane fouling being its main disadvantage.

We employ several methods to minimize membrane fouling while filtering phage lysates. First, we avoid the use of chloroform to sterilize lysates to help reduce bacterial debris that would otherwise be derived from the final lysis of phage-resistant bacterial cells, which typically develop with prolonged culturing. Moreover, in our experience, chloroform lysis does not significantly improve phage yield and it can harm certain phages[29]. Second, we subject phage lysates to two rounds of centrifugation with a sterile bottle change in between. Third, we use a pleated cartridge filter design, which provides a higher surface area. Lastly, two pleated cartridge filters are used for two-step membrane pore sizing.

Next, we use the Vivaflow™ CFF cassette as an efficient way to ultrafilter lysates with a high concentration of phages (Steps 93-105). CFF works by introducing dead-end filtered lysate under pressure across the membrane surface, instead of directly onto the micro-filter. During filtration, any material smaller than the cross-flow membrane pore of 100 kDa passes through the membrane, while larger suspended phage particles remain in the retentate stream. A membrane pore size of 100 kDa provides an equivalent to a spherical particle with a 3 nm diameter and is therefore sufficient to retain all known phages[82]. We employ diafiltration with freshly autoclaved buffer to increase the purity and improve the separation of phages from bacterial debris and the complex growth medium. Simultaneously, permeate is withdrawn at the same rate that the buffer is added, to flush out microsolutes from the phage solution. For instance, CFF with a 100 kDa membrane pore size can remove both endotoxins, which are approximately 10 kDa in size, and all known exotoxins, which are typically smaller than 30 kDa[42]. Thus, CFF is used to "wash" the phage particles while concentrating up to 2 L by a factor of 30.

Upscaling the Purification Process Using Density Gradient Ultracentrifugation

Density gradient ultracentrifugation developed by Brakke[83] is a common technique used to isolate and purify a wide range of phages purely on the basis of their density[28,]

34. We perform a self-forming density gradient isopycnic ultracentrifugal separation technique making use of differences in density between gross impurities and viruses of a CFF phage preparation (Steps 106-111; FIG. 2). In self-forming gradients, the phage solution is layered on top of the gradient medium, centrifuged, and as the solute molecules sediment to form the gradient identical phages band at their isopycnic points. Following ultracentrifugation, virus bands may be visualized as a result of their light scattering. We employ this technique for accomplishing both removal of other unwanted phage strains and gross impurities. That is, different phages will be separated by their different densities during ultracentrifugation[11]. In addition, large endotoxin aggregates will remain near the top of the gradient, while microsolutes will pass to the bottom of the gradient.

We then use dialysis to facilitate the removal of small, unwanted CsCl from phage particles in solution by selective and passive diffusion through a semi-permeable membrane (Steps 112-120; FIG. 2). Phage particles that are larger than the 100 kDa membrane-pores are retained, but small molecules and buffer salts pass freely through the membrane, reducing the concentration of those molecules in the phage preparation. Dialysis also accomplishes both removal of bacterial small molecules (for example 2.5 to 7000 kDa LPS molecules) and storage buffer exchange for phage products, but dilutes the phage preparation.

Chromatographic Removal of Endotoxins

Endotoxin removal is critical when producing therapeutic phages in bacterial systems. We further remove this hydrophobic molecule through commercial purification affinity chromatography (Steps 121-134), which is likely the most reliable and widely applied method used to remove endotoxin. We then use the Limulus amoebocyte lysate (LAL) assay (Steps 135-143) because of its sensitivity, reproducibility, and simplicity for endotoxin detection; which uses the blood coagulation system of the horseshoe crab, and clots upon exposure to endotoxin[84].

Phage Preparation Protein Analysis

Bacterial protein contamination is an immunogenic component of phage preparations. We use semi-quantitative sodium dodecyl sulfate polyacrylamide gel electrophoresis (SDS-PAGE) and Coomassie staining to visualize potential bacterial protein contamination in the final phage preparations (Steps 144-156; FIG. 4a). For example, the presence of protein smears across a variety of sizes indicates high bacterial protein contaminants as seen in the *Klebsiella* phage JG265 lysate in FIG. 4. Phage structural proteins will dominate clean preparations.

Phage Preparation Effects on Human Cell Viability

Phages cannot infect human cells. However, phages can indirectly influence mammalian cell activities[35,36,85]. In addition, bacterial contaminants in phage preparations may elicit cell inflammatory responses[38,86]. Cell-based assays are often used for screening medicinal products to determine if the test molecules have effects on cell proliferation or show direct cytotoxic effects that eventually lead to cell death[87]. In this protocol, we describe a method to test the effects of phage preparations on human cells that is based on a multi-well format where adenosine triphosphate (ATP) production is recorded using a plate reader (Steps 157-167). ATP has been widely accepted as a valid marker of viable cells[87]. When cells lose membrane integrity, they lose the ability to synthesize ATP and endogenous ATPases rapidly deplete any remaining ATP from the cytoplasm. The measurement of ATP using luciferase is the most commonly applied method for estimating the number of viable cells in high throughput screening applications. The ATP assay has a high sensitivity and is less prone to artifacts. The ATP detection reagent contains a cell lysing detergent, ATPase inhibitors to stabilize released ATP, luciferin as a substrate, and luciferase to catalyze the reaction that generates luminescence[87].

Biological Materials

Strains

PAK_P1 Phage (GenBank accession no. KC862297.1|RRID:NCBITaxon_743813)

PAK_P5 Phage (GenBank accession no. KC862301.1|RRID:NCBITaxon_1327964)

PYO2 Phage (GenBank accession no. MF490236|RRID:NCBITaxon_2034342)

E217_A65 Phage (GenBank accession no. MF490240|RRID:NCBITaxon_2034346)

SM219 Phage (this study, available from the corresponding author upon request)

JG265 Phage (this study, available from the corresponding author upon request)

JG266 Phage (this study, available from the corresponding author upon request)

*Pseudomonas aeruginosa* strain PAO1 (ATCC no. 47085|RRID:NCBITaxon_208964)

*Pseudomonas aeruginosa* strain PAK[88] (RRID:NCBITaxon_1009714)

*Serratia marcescens* strain (this study, available from the corresponding author upon request)

*Klebsiella oxytoca* strain (this study, available from the corresponding author upon request)

Cell Lines

HeLa Cells (ATCC no. CRM-CCL-2|RRID:CVCL_0030)

HEK293 Cells (ATCC no. CRL-157|RRID:CVCL_0045)

Reagents: See Example 1

Reagent Set-Up

Prepare all solutions with sterile double distilled water (ddH$_2$O) and store at room temperature (RT; 20 to 25° C.) for up to 3 months, unless otherwise indicated.

Liquid Growth Medium: Mix 10 g tryptone, 5 g yeast extract, and 5 g NaCl in 1 L of ultrapure ddH$_2$O. Autoclave.

Solid Growth Medium: Add 14 g of agar to growth medium and autoclave. Then, cool to 55° C. in a water bath for 30 min to 1 h. Sterilely pour solid growth medium into sterile Petri plates. Thickness should be approximately 5-10 mm thick. Let cool at room temperature and store at 4° C. for up to 2 weeks.

Molten soft-agar: Mix 7 g of agar to growth medium and autoclave. Then, cool to 55° C. in a water bath to prevent agar solidification before plating. Make fresh.

Tris-sodium chloride (TN) buffer: Mix 10 mM Tris (pH 7.0) and 150 mM NaCl. Adjust to pH 7.0. Autoclave and store at 4° C. for up to 3 months.

Tris-EDTA (TE) Buffer: Mix 10 mM Tris (pH 7.0) and 1 mM EDTA (pH 8.0). Adjust to pH 7.5.

10×SDS-PAGE Running Buffer: Mix 30.0 g of Tris base, 144.0 g of glycine, and 10.0 g of sodium dodecyl sulfate (SDS) in 1 L of ddH$_2$O. Make fresh.

Cesium Chloride (CsCl) Solutions: Mix 41.2 g (d=1.6), 34.13 g (d=1.5) or 20.49 g (d=1.3) in 50 mL of TN buffer. Sterile filter.

Nuclease solution: Mix 20 mg·mL$^{-1}$ DNase I and 20 mg·mL$^{-1}$ RNase A. Store at –20° C. for up to 30 months.

Precipitant solution: (30% w/v PEG-8000 and 3 M NaCl). In a sterile bottle add 110 mL ddH$_2$O and 35 g NaCl, dissolve completely. Add 60 g PEG-8000, cap bottle and shake. Incubate bottle in a 50-60° C. water bath for about 2 h, shaking occasionally (at this point, it is normal for the solution to be turbid and separated into two phases). Remove and let cool to RT, shaking occasionally. The solution should be clear or slightly turbid. Dilute to 200 mL with ddH$_2$O.

Resuspension buffer (5 mM MgSO$_4$): Add 0.0123 g of MgSO$_4$ heptahydrate per 10 mL ddH$_2$O.

Sourcing of Phages: We outline sourcing phages without enrichment cultures by plating environmental samples directly onto an isolation host and sample from formed plaques (i.e. zones of lysis). For rarer phage sourcing, an enrichment step may be required. For details see[89]. Solid source material like soil or feces should be suspended in buffer or liquid growth medium to generate an aqueous sample that can be plated directly on an isolation host.

Procedure:

Phage Plaque Isolation Timing: 3-5 d, Depending on Repetitions Needed to Obtain a Single Plaque Morphology for Each Isolated Phage.

Phage isolation (Steps 1-12) should be completed in a Class II Biosafety cabinet.

1. To isolate phage strains de novo, centrifuge aqueous environmental viral sample at 8,000×g for 30 min at 4° C. to remove bulk debris. Volume of aqueous viral sample will be dependent on separation of liquid from solid debris after centrifugation.

2. Decant the supernatant into a clean tube without disturbing debris pellet.

3. 0.2 μm syringe filter the environmental viral sample.

4. In a sterile test tube, mix 100 μL of bacterial host at OD$_{600}$ 0.2 and 100 μL of the filtered viral sample.

5. Add 3 mL of molten soft-agar, mix gently, and pour over solidified agar Petri plate. If the bacterial lawn is clear after incubation, dilute the environmental sample to obtain single plaques.

6. Incubate under appropriate temperature and atmospheric growth conditions for 12-18 h or until plaques form on a confluent lawn of bacteria.

7. Using a Pasteur pipette, select one PFU and re-suspend in 100 μL of PBS in a microcentrifuge tube.

8. Prepare serial dilutions (for example tenfold) in PBS.

9. In sterile test tubes, mix 10 μL of the 10$^{-5}$, 10$^{-6}$ or 10$^{-7}$ dilutions with 500 μL of bacteria grown to OD$_{600}$ 0.2.

10. Add 3 mL of molten soft-agar to each, mix gently, and pour over solidified agar Petri plate.

11. Incubate under appropriate temperature and atmospheric growth conditions for 12-18 h or until plaques are visible on a confluent lawn of bacteria.

12. Repeat Steps 7 through 11. In alternative embodiments, repeat Step 12 three times, or until all PFUs exhibit the same observed plaque morphology.

Small-Scale Cultivation, Timing 15-21 h

13. Using a Pasteur pipette, select one PFU and re-suspend in 100 μL of PBS in a microcentrifuge tube.

14. Warm 50 mL of growth medium in a sterile 250 mL GL45 screw-top flask with a GL45 0.22 μm PTFE membrane vented cap.

15. Add 500 μL of bacteria grown to OD$_{600}$ 0.2 and incubate at appropriate temperature and atmospheric growth conditions for 20 min.

16. Add 50 μL phage obtained in Step 13 and incubate under appropriate bacterial growth conditions for 12-18 h.

17. To remove bulk bacterial debris, transfer lysates to 50 mL conical centrifuge tubes and centrifuge at 6,000×g for 30 min at 4° C.

18. Filter sterilize the supernatant with a 0.2 μm syringe filter into a sterile 50 mL conical tube. Do not disturb the pellet during decanting.

19. Titer the sample as described in Step 20.

Store phage lysate at 4° C. for up to 12 months.

Phage Titration

20. For routine phage titering, we describe two techniques (see Experimental Design—Phage titration): Follow 'Option A' for agar overlay titering and 'Option B' for spot plaque titering. Alternatively, phages can be quantified via their genome copy number by qPCR (For details see[49,50]).

OPTION A| Agar Overlay Tittering, Timing 20 h i. Add 100 μL of phage sample into a microcentrifuge tube containing 900 μL of PBS, mix well.

ii. Pipette 100 μL from Step i dilution into a $2^{nd}$ a microcentrifuge tube containing 900 μL of PBS, mix well.

iii. Repeat step ii for the remaining microcentrifuge tubes to create a dilution series of $10^{-1}$ to $10^{-8}$.

iv. In sterile test tubes, mix 100 μL of each serial dilution with 100 μL of bacteria grown to $OD_{600}$ 0.2.

v. Add 3 mL of molten soft-agar, mix gently, and pour the mixture over a solidified agar Petri plate.

vi. Incubate under appropriate temperature and atmospheric growth conditions for 12-18 h or until plaques form on a confluent lawn of bacteria.

vii. Determine phage stock concentration as $PFU \cdot mL^{-1}$.

OPTION B| Spot Plaque Tittering, Timing 19 h i. Dry a growth agar Petri plate for 30 min in a biosafety cabinet.

ii. To seed a lawn of bacteria, pour 3 mL of bacteria grown to $OD_{600}$ 0.2 onto the dry growth agar Petri plate and quickly remove excess culture.

iii. Dry the Petri plate in a biosafety cabinet for 15 min.

iv. While drying, add 90 μL of PBS to 8 wells row-by-row in a 96-well microtiter plate.

v. Add 10 μL of phage sample to the first well, mix well.

vi. Pipette 10 μL from the $1^{st}$ well into the $2^{nd}$ well, mix well.

vii. Repeat step vi for the remaining wells to create a dilution series ($10^{-1}$ to $10^{-8}$).

viii. Using an 8-channel pipette, spot 4 μL from each well onto a dried seeded lawn of bacteria prepared in (i-iii). Completely dry spots before moving the plate to incubator.

ix. Incubate plate at appropriate temperature and atmospheric growth conditions for 12-18 h or until plaques form on a confluent lawn of bacteria.

x. Determine phage stock concentration as $PFU \cdot mL^{-1}$.

DNA Extraction, Timing 2 h

Steps 21-56 describe how to extract genomic DNA from small scale phage lysates following a modified version of a previously published protocol[90]. There are many DNA extraction kits, including the Promega Wizard, Qiagen PowerViral Kit, and Norgen Biotek. This protocol uses the Ciculomics Nanobind Tissue Big DNA Kit to generate long DNA fragments suitable for the Oxford Nanopore MinION sequencer.

21. Place the lysate from Step 18 into a clean 50 mL centrifuge tube. Add 0.5 μL of nuclease solution per mL of lysate ($10 \ \mu g \cdot mL^{-1}$ DNase & RNase final). Incubate the lysates at 37° C. for 30 min, or at RT for 2 h.

22. Add ½ volume of the precipitant solution compared to the lysate (10% (wt/vol) PEG-8000, 1 M NaCl final concentration). Mix gently by inversion. Incubate on ice for at least 60 min; precipitation works best when incubated at 4° C. overnight. Most phages are stable in this state for several days.

23. Centrifuge the precipitated phage lysate at 10,000×g, 4° C., 10 min.

24. Carefully remove the supernatant by either aspiration or carefully pouring into a separate tube, and retain the transparent or slightly opaque pellet in the original tube.

25. Gently, resuspend the pellet in 0.5 mL of 5 mM $MgSO_4$ and briefly (5-10 s) centrifuge at 10,000×g at RT to pellet any remaining insoluble particles.

26. Transfer the supernatant to a sterile microcentrifuge tube for the remaining steps.

27. Before proceeding, dilute the supplied CW1 and CW2 buffers with 96%-100% ethanol, as described by the manufacturer.

28. Add 20 μL of proteinase K solution.

29. Add 20 μL of the supplied CLE3 buffer.

30. Pulse vortex 10 times for 1 s each.

31. Incubate in the ThermoMixer at 56° C. and 900 rpm for 30 min.

32. Add 200 μL of the supplied BL3 buffer.

33. Pulse vortex 10 times for 1 s each.

34. Incubate microcentrifuge tube in the ThermoMixer at 56° C. and 900 rpm for 30 min.

35. Add the Nanobind disks to the lysate.

36. Add 300 μL of isopropanol.

37. Mix microcentrifuge tube by inversion 5 times.

38. Mix on a rotator at 10 rpm for 10 min.

39. Place microcentrifuge tube in the Magnetic Tube Rack.

40. Carefully remove the supernatant taking care not to disturb the Nanobind disks.

41. Add 700 μL of the supplied CW1 buffer.

42. Mix microcentrifuge tube by vigorous inversion 4 times.

43. Place microcentrifuge tube in the Magnetic Tube Rack

44. Carefully remove the supernatant taking care not to disturb the Nanobind disks.

45. Add 500 μL of the supplied CW2 buffer.

46. Repeat Steps 42-45.

47. Mix by vigorous inversion 4 times.

48. Place microcentrifuge tube in the Magnetic Tube Rack.

49. Carefully remove the supernatant taking care not to disturb the Nanobind disks.

50. Spin the microcentrifuge tube for 5 s.

51. Remove any remaining liquid without disturbing the Nanobind disks.

52. Repeat Steps 50-51.

53. Add 100 μL of the supplied elution buffer (EB) and incubate at RT for 10 min.

54. Transfer the DNA eluate to a new, sterile, microcentrifuge tube.

55. Spin the microcentrifuge tube containing the Nanobind disks for 5 s. Remove additional eluate and pipette into the same microcentrifuge tube in Step 54.

56. Leave at RT for approximately 1 h to let the DNA re-dissolve.

Phage DNA can be stored at 4° C. for <2 weeks and −20° C. <6 months.

Sequencing Library Preparation, Timing 10 Min

Steps 57-62 use Oxford Nanopore MinION for rapid DNA sequencing of phage genomes. Thaw all components on ice, and store on ice until needed. Centrifuge all components briefly before use.

57. In a 0.2 mL PCR tube, mix 7.5 µL of phage DNA (>400 ng) preparation from Step 56 and 2.5 µL of fragmentation mix (solution FRA).

58. Mix by gently tapping the tube, and then centrifuge briefly to bring all the contents to the bottom of the tube.

59. Incubate the tube at 30° C. for 1 min and then at 80° C. for 1 min.

60. Add 1 µL of rapid adapter (solution RAP)

61. Mix by gently tapping the tube, and then centrifuge briefly to bring all the contents to the bottom of the tube.

62. Incubate the tube at RT for 5 min.

The sequencing library can be stored briefly on ice until loaded into the DNA sequencer.

DNA sequencing, timing 1-48 h, depending on desired reads coverage, with first reads recovered in an hour. More reads will increase confidence.

63. Open MinKNOW software on the computer

64. Plugin the MinION device and insert a flow cell (FIG. 2b)

65. Enter the sample ID and flow cell ID on the computer

66. Run the Platform QC script and confirm active pores available

67. Open the cover of the flow cell, and drawback a few microliters of fluid to remove bubbles, taking care not to remove the buffer from the pores.

68. To prepare the flow cell priming mix, add 30 µL of Flush Tether (FLT) directly to the tube of mixed flush buffer (FLB), and mix by pipetting up and down. Centrifuge briefly.

69. Load 800 µL of the priming mix into the flow cell via the priming port. Be careful to avoid introducing air bubbles into the flow cell. Incubate at RT for 5 min.

70. Mix the sequencing reaction in a new tube:

34 µL Sequencing Buffer (SQB)

25.5 µL Loading Beads (LB)

4.5 µL Nuclease-free water

71 L DNA library from Step 62

71. Mix by pipetting and centrifuge briefly

72. Access the SpotON sample port by lifting the cover.

73. Load 200 µL of the priming mix into the flow cell via the priming port prepared in in Step 68. Be careful to avoid introducing air bubbles into the flow cell.

74. Carefully add the 75 µL of sequencing reaction from Step 71, in a dropwise fashion. Be careful to ensure that each drop enters the flow cell.

75. Carefully replace the SpotON sample port cover ensuring the port is filled by the bung, close the priming port cover and close the MinION lid.

76. On the MinKNOW software, click Start Run.

77. Upon completion of the sequencing, flow cells can be washed and retained for further use. DNA sequences will be available almost immediately and will continue to accumulate while there are active pores.

Bioinformatics Analysis, Timing 12 h

78. Upload the fastq files from MinKNOW to a Linux server, or equivalents

79. Assemble the long reads with canu[91] by running the following code:

b. canu-p phage-d assembly genomeSize=40 k-nanopore-raw phage.fastq The primary options are -p for the name, -d for the location to write the output, and the fastq output from MinKNOW.

80. Compare the phage genomes to antimicrobial and virulence gene databases using Abricate (https://github.com/tseemann/abricate) by running the following code:

b. for DB in argannot card megares ncbi plasmidfinder resfinder vfdb; do abricate—threads 10—db $DB assembly/done>abricate.out 81. Upload the genome to PHACTS to predict whether it is virulent or temperate virus[77].

82. Upload the genome to PATRIC (https://patricbrc.org/) to annotate other genes in the genome.

83. Select phages for large-scale production based on the lack of predicted antibiotic and virulence genes, and the likelihood that the isolated phage is virulent (i.e. strictly lytic lifecycle).

Liter-Scale Shake Flask Cultivation, Timing 18-24 h

Large phage production batches are limited by maximum centrifuge rotor capacity. Steps 84-90 describe how to process 1 L cultures; thus 6 flask cultures are performed in parallel.

84. In a sterile 2 L GL45 screw-top flask with a GL45 0.22 µm PTFE membrane vented cap, warm 1 L of complex growth medium.

85. Add 5 mL of bacteria grown to $OD_{600}$ 0.2 and incubate appropriate temperature and atmospheric growth conditions for 20 min.

86. Add phage from Step 18 at a Multiplicity of Infection (MOI) of 0.1 and incubate under appropriate bacterial growth conditions for 12-18 h.

87. To remove bulk bacterial debris, transfer lysates to 1 L centrifuge bottles and centrifuge at 8,000×g for 45 min at 4° C. (FIG. 1).

88. Decant the supernatants into fresh, sterile 1 L centrifuge bottles without disturbing the bacterial pellet.

89. Centrifuge again at 8,000×g for 45 min at 4° C.

90. Decant supernatant into sterile 1 L glass bottle.

Dead-End Filtration, Timing 1 h

91. Assemble 0.8/0.45 µm and 0.45/0.2 µm capsule filters inline. Use the peristaltic pump to filter sterilized supernatant into a sterile glass bottles. Capsule filters can process up to 2 L before clogging, but can be cleaned and reused following manufacturer's protocol.

92. Titer the sample as described in Step 20. The phage lysate titer should be >$10^9$ PFU·mL$^{-1}$.

Phage preparation can be stored at 4° C. for <6 months.

Ultrafiltration, Diafiltration, and Concentration, Timing 8 h (2 h Per 1.5 L)

93. Assemble the peristaltic pump and CFF cassette as shown in FIG. 1.

94. Circulate 500 mL of sterile ddH$_2$O through the cassette and discard.

95. Place the intake and retentate hoses into the 0.2 µm sterile phage supernatant solution from Step 92.

96. Place the filtrate hose into a sink or waste container.

97. Recirculate (up to 1.5 L per batch) supernatant until ~200 mL remains.

98. Add 400 mL of sterile ddH$_2$O.

99. Recirculate supernatant until ~200 mL remains.

100. Add 400 mL of sterile TN buffer.

101. Recirculate supernatant until ~200 mL remains.

102. Repeat steps 100 and 101, until supernatant becomes clear and colorless.

103. Pause pump, place intake and retentate hoses in a sterile 50 mL conical tube, and recirculate while continuously adding remaining supernatant until 40 mL of concentrate remains (1$^{st}$ fraction).

104. Pause pump, place intake hose with retentate hose into a sterile 50 mL conical tube with 30 mL of TN buffer. Circulate briefly and remove intake hose. Collect 30 mL of concentrate ($2^{nd}$ fraction). Subsequent fractions can be collected if lower concentration phage stocks are desired.

105. Titer the sample as described in Step 20. The phage concentrate should be >10-fold higher in titer than that in Step 92.

Phage preparation can be stored at 4° C. for <2 weeks.

Density Gradient Ultrapurification TIMING 6 h

Density gradient ultracentrifugation (Steps 106-111) and dialysis (Steps 112-120) may not be required to meet regulatory endotoxin safety limits of phage products[41]. Optionally, proceed to Step 135 for endotoxin quantification.

106. In an open top ultraclear (14×89 mm) round bottom tube, prepare a CsCl step density gradient by layering 2 mL of d=1.6, 3 mL of d=1.5, and 3 mL of d=1.3, from the bottom up. Avoid disturbing the previous density layer during preparation.

107. Fill the remaining tube volume with phage concentrate (~4 mL) from Step 104.

108. Place tubes inside buckets and balance on a SW41 rotor. Cool rotor to 4° C. and centrifuge with all buckets, even if unused.

109. Ultracentrifuge at 28,000×g for 4 h at 4° C.

110. Carefully extract tubes from buckets using tweezers.

111. With a concentrated light source, extract the visible band containing the phage particles by puncturing the thin-walled ultraclear tube with a 26G needle and syringe.

CsCl Concentrate Dialysis, Timing 1 d

112. Chill up to 3 L of sterile ddH$_2$O (4° C.) in a large beaker placed on a stir plate.

113. Place a magnetic stir bar in the beaker.

140. Clamp one end of the 100 k MWCO dialysis tubing and add the CsCl phage concentrate from Step 111.

115. Clamp the other end and secure the clamped dialysis tubing to a float.

116. Dialyze CsCl phage concentrate in the pre-chilled sterile ddH$_2$O and stir for 30 min at 4° C.

117. Exchange ddH$_2$O with up to 3 L of pre-chilled sterile storage buffer (for example PBS) and dialyze for 1 h.

118. Repeat step 117, but prolong dialysis to 24 h.

119. Recover phage concentrate.

120. Titer the sample as described in Step 20. The phage titer should be between $10^9$-$10^{12}$ PFU·mL$^{-1}$.

120. Phage preparation can be stored at 4° C. for <2 weeks.

LPS-Affinity Chromatography, Timing 2 h

Steps 121-134 are specific to the Pierce™ High Capacity Endotoxin Removal Spin Column.

121. Equilibrate and regenerate the spin column as per the manufacturer's instructions.

122. Place the spin column into a collection tube and centrifuge at 500×g for 1 min at RT to discard the regeneration solution.

123. Remove the cap and insert the bottom plug. Add 8 mL of 2M NaCl, replace the cap and invert the column several times.

124. Loosen the cap and remove the bottom plug. Place the column in a collection tube and centrifuge at 500×g for 1 min at RT to discard the solution.

125. Remove the cap and insert the bottom plug. Add 8 mL of supplied endotoxin-free H$_2$O. Replace the cap and invert the column several times.

126. Loosen the cap and remove the bottom plug. Place the column in a collection tube and centrifuge at 500×g for 1 min at RT to discard the water.

127. Remove the cap and insert the bottom plug. Add 8 mL of endotoxin-free PBS, replace the cap and invert the column several times.

128. Loosen the cap and remove the bottom plug. Place the column in a collection tube and centrifuge at 500×g for 1 min at RT to discard the PBS.

129. Repeat steps 127 and 128 two additional times.

130. Remove the cap and insert the bottom plug. Add 10 mL dialyzed phage concentrate from Step 119 to the resin, replace the cap and invert the column several times.

131. Incubate the column with gentle end-over-end mixing at 4° C. for 45 min.

132. Loosen the cap and remove the bottom plug. Place column in a sterile collection tube and centrifuge at 500×g for 1 min at RT to collect the sample.

133. Repeat steps 121-132 until all phage concentrate is processed.

134. Titer the sample as described in Step 20. The phage titer should be between $10^9$-$10^{12}$ PFU·mL$^{-1}$.

Phage preparation can be stored at 4° C. for less than (<) 6 months.

Phage Preparation Endotoxin Quantification, Timing 2 h.

Steps 135-143 are specific to the Pierce™ LAL Chromogenic Endotoxin Quantitation Kit.

135. Equilibrate solutions to room temperature, as per the manufacturer recommendation.

136. Prepare LPS standards provided in the kit using "High Standards" option.

137. Add prepared standards, the blank, and samples from Step 133 to a 96 well microtiter plate. Appropriately dilute phage samples to be within the linear range of the high standard.

138. Warm plate to 37° C. and add 50 μL of LAL to each well. Tap plate lightly 10 times to mix.

139. Reconstitute the chromogenic substrate solution and warm it at 37° C., 5 min before use. Work quickly to prevent inactivation of solutions after reconstitution.

140. Add 100 μL of the chromogenic solution to each well.

141. At 6 min, add 50 μL of 25% (vol/vol) acetic acid to stop the reaction.

142. Immediately, measure OD$_{405nm}$ in a microplate reader.

143. Extrapolate the endotoxin level from the standard curve. Refer to Supplementary Table 1 for anticipated endotoxin concentration.

Phage Preparation Protein Analysis, Timing 4 h

144. Determine the absorbance of phage preparations from Step 133 at 280 nm to measure protein level. This will vary between phage strains but should be between 1-3 mg·mL$^{-1}$.

145. Dilute phages to 15 μg in 20 μL of 1× Laemmli sample buffer.

146. Incubate samples at 90° C. for 5 min.

147. Centrifuge samples at 13,000 rpm for 60 sec at RT.

148. Prepare a 10% (wt/vol) acrylamide gel for SDS-PAGE electrophoresis.

149. Mount the gel into the tank, remove combs, and completely fill the inner chamber of the tank and ¾ of the outer chamber with 1×SDS-PAGE running buffer.

150. Pipette 3 μL of the standard and 20 μL of sample into the subsequent wells.

151. Run electrophoresis at 100V for about 60 min.

152. Wash the gel with ddH$_2$O 3 times for 15 min each.

153. Incubate the gel with 50 mL Coomassie blue staining solution at RT for 1 h.

154. Decant solution and add 50 mL ddH$_2$O. Incubate at RT for 30 min on a rocker.

150. Decant and repeat Step 154 three times.

156. Image the gel using a gel dock station or conventional camera.

Phage Preparation Effects on Human Cell Viability, Timing 3 d

In Steps 157-167, we describe how to use the CellTiter-Glo® luminescent cell viability assay (Promega) to determine the number of viable cells in culture after phage preparation exposure based on quantitation of the ATP present, an indicator of cell proliferation and cytotoxicity.

157. In a 96-well tissue culture plate, seed wells with 100 μL of media containing about 20,000 of HeLa or HEK293 cells. Use a clear bottom white walled microplate to minimize well luminescence cross talk.

158. Incubate at 37° C., 5% CO$_2$, for 24 h.

159. The next day, check for a confluent monolayer of cell culture.

160. From Step 133, dilute phage stock to 10$^8$ PFU·mL$^{-1}$ and 10$^9$ PFU·mL$^{-1}$.

161. Add 10 μL of 10$^8$ PFU·mL$^{-1}$ stock for an approximate concentration of 1 cell: 100 phages, 10 μL of the 10$^9$ PFU·mL$^{-1}$ stock for a concentration of 1:1000 phages.

162. For positive control add 10 μL 1% (wt/vol) SDS and for negative control add 10 μL PBS. Ensure that two wells are filled with medium only.

163. Incubate at 37° C., 5% CO$_2$, for 24 h.

164. Equilibrate the 96-well plate to room temperature for 30 min before adding 100 μL CellTiter-Glo™ to all wells.

165. Mix plate on an orbital shaker for 2 min to induce cell lysis.

166. Incubate at 22° C. for 10 min.

167. Measure luminescence on a microplate reader (see 'Anticipated results' below for example data).

Troubleshooting advice can be found in Table 4, FIG. 12.

Timing:

The timing information is an estimate for phages for aerobic Gram-negative bacteria.

Steps 1-12, phage plaque isolation: 3-5 d, depending on repetitions needed to obtain a single plaque morphology.

Steps 13-19, small-scale cultivation: 15-21 h

Step 20 Option A, phage titration using agar overlay titering: 20 h

Step 20 Option B, phage titration using spot plaque titering: 19 h

Steps 21-56, DNA extraction: 2 h

Steps 57-62, sequencing library preparation: 10 min

Steps 63-77, DNA sequencing: 1-48 h, depending on desired reads coverage.

Steps 78-83, bioinformatics analysis: 12 h

Steps 84-90, large-scale cultivation: 24-30 h

Steps 91-92, dead-end filtration: 1h

Steps 93-105, ultrafiltration, diafiltration, and concentration: 8 h (2 h per 1.5 L)

Steps 106-111, density gradient ultrapurification: 4 h

Steps 112-120, CsCl concentrate dialysis: 24 h

Steps 121-134, LPS-affinity chromatography: 2 h

Steps 135-143, phage preparation endotoxin quantification: 2 h

Steps 144-156, phage preparation protein analysis: 4 h

Steps 157-167, phage preparation effects on human cell viability: 3 d

Process Optimization at Liter-Scale Production

This protocol for purifying phages employs a combination of modified classical techniques, modern membrane filtration processes, and omission of certain common practices (for overview see FIG. 1). A typical six-liter shake-flask cultivation yields between 16-30 mL of final product, providing up to 64,000 treatment doses at 10$^9$ PFU—a commonly prescribed IV dose[1]—, depending on the phage-bacteria pair (Table 3 and Supplementary Table 1). Because final phage products contain very low endotoxin levels, theoretically would be possible that treatments of up to 10$^{12}$ PFU could be prescribed to humans, and be within regulatory limits of 5 EU·kg$^{-1}$ h$^{-1}$ [41]. In comparison, Belgium is the only western country that routinely produces phages in a laboratory under prescription, as a "magistral" preparation (i.e. drug compounding)[40]. To the best of our knowledge, magistral phage products are generally purified by high-speed lysate centrifugation and subsequent affinity chromatography endotoxin removal[40]. In practice, this approach yields ~10$^7$ PFU·ml$^{-1}$ and 12.5 EU·ml$^{-1}$ [39]. A recent extended access phage therapy reported PEG/NaCl, density gradient ultracentrifugation and dialysis purification of *Mycobacterium* phages yielded a comparably high 10$^{11}$ PFU·ml$^{-1}$ and undetectable endotoxin[2]. Mycobacteria however do not produce LPS. PEG-CsCl-dialysis can effectively reduce LPS to <0.05 EU·ml$^{-1}$ experimentally, it does so by adding organic solvents and generally at the expense of phage yield[21].

In FIG. 3, we show that a relatively high phage titer is maintained during downstream processes, while endotoxin is being reduced to a safe level for human intravenous use. In addition, we show that high titer and low endotoxin phage preparation is independent of phage strain and viral structure. For example, myophages PAK_P1 and PAK_P5 were isolated from French wastewater with the *P. aeruginosa* strain PAK[92], while myophage E217 and podophage PYO2 were isolated from Italian wastewater with the *P. aeruginosa* strain PAO1[24]. Final production runs produced titers of 6×10$^{10}$, 4×10$^{11}$,2×10$^{11}$ and 4×10$^{12}$ PFU·mL$^{-1}$, respectively (Table 3). High-titer final stocks are dependent on the initial phage cultivation performance. Six-liter lysates of *Pseudomonas* phages produced titers of 10$^{10}$ PFU·mL$^{-1}$ that could be concentrated up to 10$^{12}$PFU·mL$^{-1}$, whereas lysates of *K. oxytoca* and *S. marcescens* phages produced lower titers of 10$^9$ PFU·mL$^{-1}$ that could be concentrated to 10$^{10}$ PFU·mL$^{-1}$ (FIG. 3 and Supplementary Table 1). Because CFF was found to be the main phage concentrating technique, a larger volume of lysate from phages that do not produce high titers would be required to achieve higher final product concentrations.

Other practiced phage cultivation and purification approaches, such as polyethylene glycol precipitation, centrifugal ultrafiltration, organic solvent extraction, enzymatic inactivation, and anion-exchange chromatography were previously shown to produce equally high phage concentrations, but can retain high amounts of endotoxins[11,18,27-34,45]. Our protocol focuses on early removal of endotoxins by conducting multiple low-speed centrifugation steps, microfiltration and cross-flow ultrafiltration with phage particle washing steps, which reduce the majority of LPS in phage samples (FIG. 3). By contrast, we found subsequent CsCl density gradient ultracentrifugation increases, in some preparations, LPS quantity by up to 30% (Supplementary Table 1). Our results conflict with the recent study by Van Belleghem et al. that compared several endotoxin removal methods and concluded that CsCl density gradient ultracentrifugation was the most effective at removing endotoxin[34]. The study also showed effective endotoxin removal came at the expense of a phage yield reduction. In this study, we observe that the phage titer generally increases after CsCl density gradient ultracentrifugation and dialysis, except for phage JG266 (FIG. 3).

Our results suggest that CFF with a MWCO 100 kDa pore size, in combination with several buffer washes, produces a phage product with endotoxin quantities within FDA regulatory limits for human intravenous use. Importantly, most exotoxins are smaller than 100 kDa[42]. The semi-automated CFF used in our approach is able to concentrate phages between 10- to 100-fold, while removing endotoxin by >4000-fold and rich bacterial growth medium in a single-step (FIG. 3). CFF is an effective phage concentration technique[32,33]. However, using lower MWCO pore sizes appears to trap endotoxins along with the phage particles[32]. The recent "Phage On Tap" purification protocol showed that centrifugal ultrafiltration was more rapid technique to concentrate phage particles, but also trapped endotoxins[33]. Nevertheless, we show that endotoxins in phage samples can be further reduced by commercially available LPS-affinity chromatography (FIG. 3 and Supplementary Table 1).

Phage Product Safety Testing

Throughout the phage cultivation and purification process we maintain phage strain homogeneity by monitoring for changes in plaque morphology while phage titering. After each processing step, phage stocks should maintain a distinct single plaque phenotype. Homogeneity is further confirmed by obtaining a distinct single band after density gradient as would be expected with a sample containing phage particles with the same density and shape[83].

As mentioned above, at a therapeutic dose of $10^9$ PFU, endotoxin in phage lysates are reduced at least a $10^6$-fold for all seven phages tested, without the use of organic solvents (FIG. 3 and Table 3). Simultaneously, <100 kDA microsolute permeate is withdrawn from phage preparations during CFF, suggesting that small molecules, such as exotoxins that are typically smaller than 30 kDa[42], are also removed from final phage products. However, none of our phages or bacterial strains contained a known exotoxin to validate this claim.

FIG. 4a shows that our example phage preparations are free of gross bacterial proteins with SDS-PAGE staining not showing significant protein smearing. This becomes especially clear when comparing the 0.2 μm filtered lysate of Klebsiella phage JG265 with its purified preparation (FIG. 4a). The lysate displays many bands, while the purified phage preparation displays a few distinct bands unique for each denatured phage, indicating differences in their structural proteins. PAK_P1 and PAK_P5 share a major protein band at ~50 kDa, and E217, PYO2, JG265 and JG266 at 75 kDA. Between phage strains however other proteins are not conserved with a variety of bands ranging from 20 to 150 kDa. To identify these specific phage proteins further mass spectrometry analysis would need to be conducted[93].

Because SDS-PAGE is not sufficient to guarantee absence of harmful toxins, we further conducted cell viability testing[94]. In vitro models to test for phage preparation effects on human cells and exclude potentially harmful products is an important consideration, but there is no standard model of phage pharmaceutical standard available. As a rapid test for eIND request, quantitation of intracellular adenosine triphosphate can be used as a measurement of the metabolic activity of human cells. With two human cell lines, HeLa and HEK293, we show that cell viability is not significantly different from untreated cell controls after exposure to each of the phage strains purified after cultivation with Pseudomonas, Klebsiella or Serratia (FIG. 4b-g). By contrast, centrifuged phage lysate causes a significant decrease in cell metabolic activity. Therefore, our results suggest that downstream purification of phage lysates can produce a product free of harmful bacterial toxins and other components.

Together, these results suggest that our protocol for phage purification is reliable and reproducible, helping to ensure the safety and efficacy of phage products for human use.

Overview of bacteriophage cultivation and purification. The procedure starts with sourcing and isolating phages with a target bacterial strain. After multiple rounds of agar plaque isolation, a single plaque is small-scale cultivated overnight. Next, the newly isolated phage genome is sequenced, annotated, and screen for lysogenic and harmful genes. Phages deemed potentially safe for human use are then liter-scale cultivated. After overnight culturing, phage lysate is sterilized by pressure driven double dead-end filtration and cross-flow ultrafiltration (See FIG. 2 for filtration scheme). Cross-flow ultrafiltration also diafiltrates to remove growth medium and concentrates phage particles in buffer. As an option, cesium chloride (CsCl) density gradient ultracentrifugation and dialysis can be used to further confirm phage stock homogeneity. LPS-affinity chromatography is used to remove residual endotoxins. Lastly, the final phage preparation purity and safety is tested by quantifying endotoxin level, protein abundance, and cell viability after phage sample exposure.

Figure and Table Legends

FIG. 8 illustrates a schematic of phage lysate dead-end filtration (Steps 91) and cross-flow filtration (Steps 93-104) removal of impurities. Phage lysates are sterilized by inline 0.8, 0.45, 0.45 and 0.22 μm membrane filtration to remove whole bacterial cells and cellular debris. Then cross-flow filtration (CFF) is used to remove growth medium and microsolutes smaller than 100 kda (for example, endotoxin, peptidoglycan, exotoxins, flagella, nucleic acids, etc.), while concentrating the phages in phosphate buffer.

FIG. 9 graphically illustrates process stepwise phage titer and endotoxin concentration throughout processing. Plaque forming units (PFU) per mL (right y-axis; closed circles) and endotoxin units (EU) normalized to $10^9$ PFU (left x-axis, open circles) after phage lysate sterilization (Lysate, Step 92), cross-flow ultrafiltration (CFF; Step 105), density gradient ultracentrifugation and dialysis (CsCl, Step 120) and LPS-affinity chromatography (Chrom, Step 134). See Step 20 Option B and Steps 121-134 for phage titration and endotoxin quantification procedures, respectively.

FIG. 10 graphically illustrates purity and safety analyses of final phage preparations. (a) SDS-PAGE analysis of protein content in final phage samples (Step 133) at $10^9$ PFU compared to an exemplified sterilized phage lysate (produced by Steps 84-92) and Precision Plus Protein ladder (Bio-Rad). (b-g) Human HeLa cell-line (b, d, f) and HEK293 cell-line (c, e, g) viability after 24 h co-incubation with final preparations of P. aeruginosa phages (b, c), K. oxytoca phages (d, e) and S. marcescens phage (f, g) at cell:phages ratio of 1:100 and 1:1000 quantified by the CellTiter-Glo™ assay (Steps 157-167). Viability was normalized to untreated cells. Pseudomonas and Serratia sterilized phage lysates were significantly lower that corresponding final phage preparations (p<0.006), whereas there was no significant difference in cell viability between Klebsiella sterilized lysate and phage treated. One-way ANOVA; error bars represent SEM; n=3-6).

Supplementary Table 1 (see FIG. 13). Bacteriophage cultivation and purification titers and endotoxin units after each production process.

Example 3: Reducing Bacterial Toxins in Phage Lysates

Bacterial components including endotoxin in phage lysates can be significantly reduced by cooling phage lysates. A plate lysate is a concentrated liquid sample of phages that is obtained by infecting bacteria host cells with the phage strain of interest and letting the phage replicate and lyse their host cells. Lysis creates a significant amount of bacterial debris including endotoxin that is harmful to humans and animals. Typically, cultures are grown at the optimal temperature of the bacteria (for example at 37° C.) for 24 hours. However, we found that phage resistant mutants arise and repopulate the culture well before all phage susceptible host cells are infected by phages (see FIG. 14).

Figure 15:
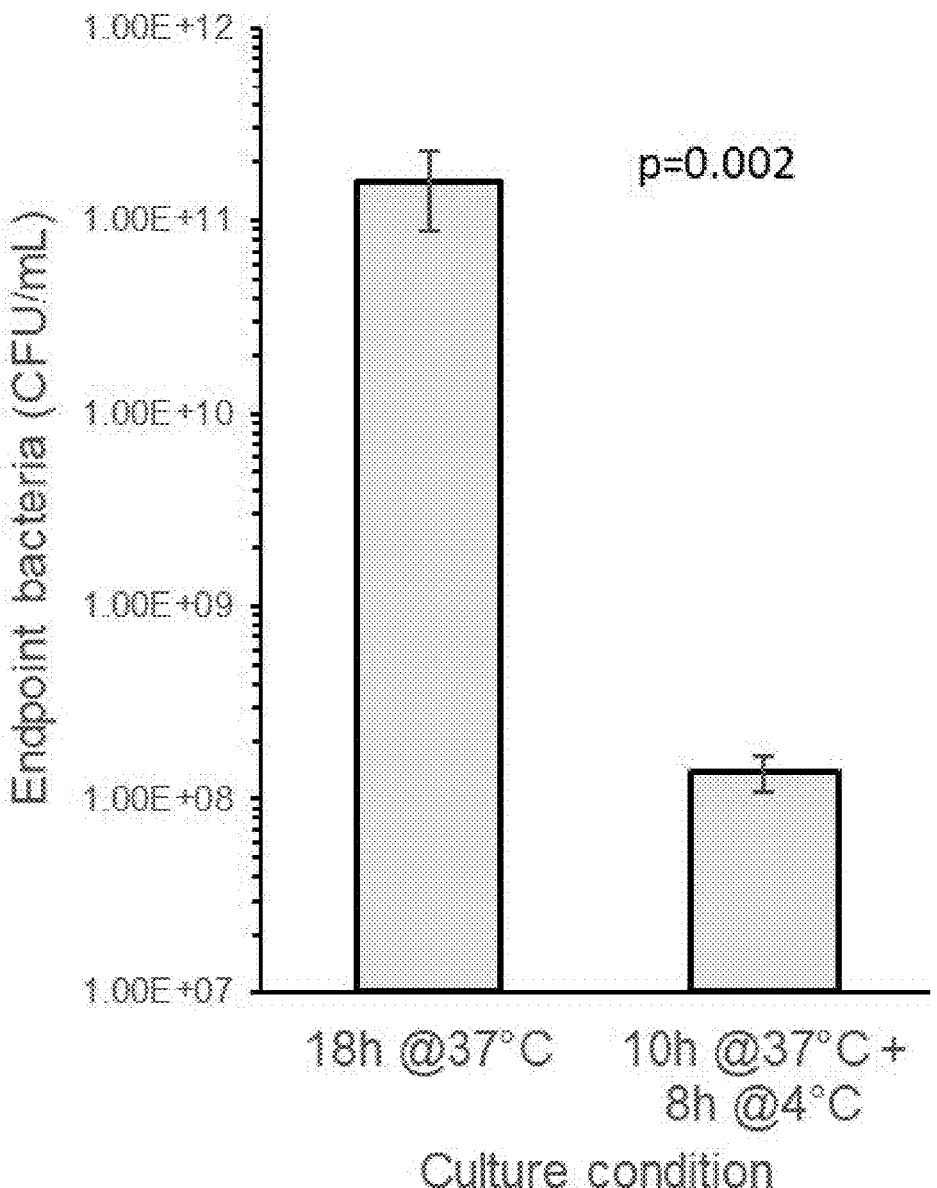
FIG. 15 graphically illustrates reduction in bacteria count after phage dultivation: at the end of phage cultivation, live bacteria counts in lysates were reduced by 3-log by cooling the culture to 4° C. after the initial appearance of phage resistant mutant outgrowth when compared to continuous culturing at 37° C., as described in Example 3.
Figure 16:
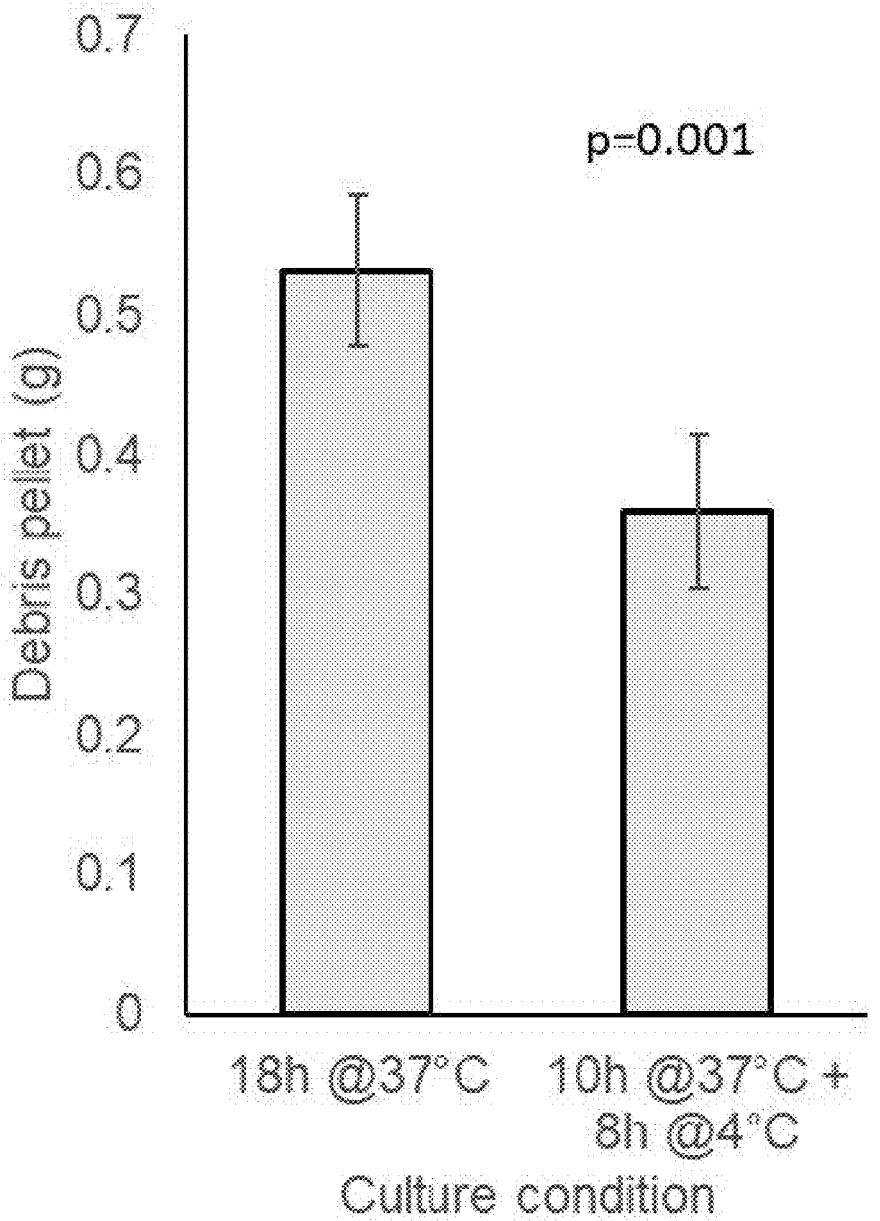
FIG. 16 graphically illustrates reduction in bacterial debris pellet weight after phage lysate centrifugation: after centrifugation of phage lysates, bacteria and phages grown continuously at 37° C. exhibited a 33% increase in bacterial debris pellet weight compared to cultures cooled to 4° C.

We found that by cooling phage cultures at the point where phage insensitive bacterial cells arise in the cultures, reduced live bacterial cells in phage lysates by 3 log after 18 hours (FIG. 15). This allowed bacterial debris to by reduced by greater than (>) 33% in phage lysates (FIG. 16). By reducing gross bacterial cells and debris in phage lysates, phage safety is increases by reducing free endotoxin that needs to be removed by subsequent purification steps. In addition, we found that the volume of cooled phage lysates that could be dead-end filter sterilized was increased by 2-fold before clogging. Importantly, cooling phage cultures did not affect total phage yield after 18 hours (FIG. 17).

Figure 14:
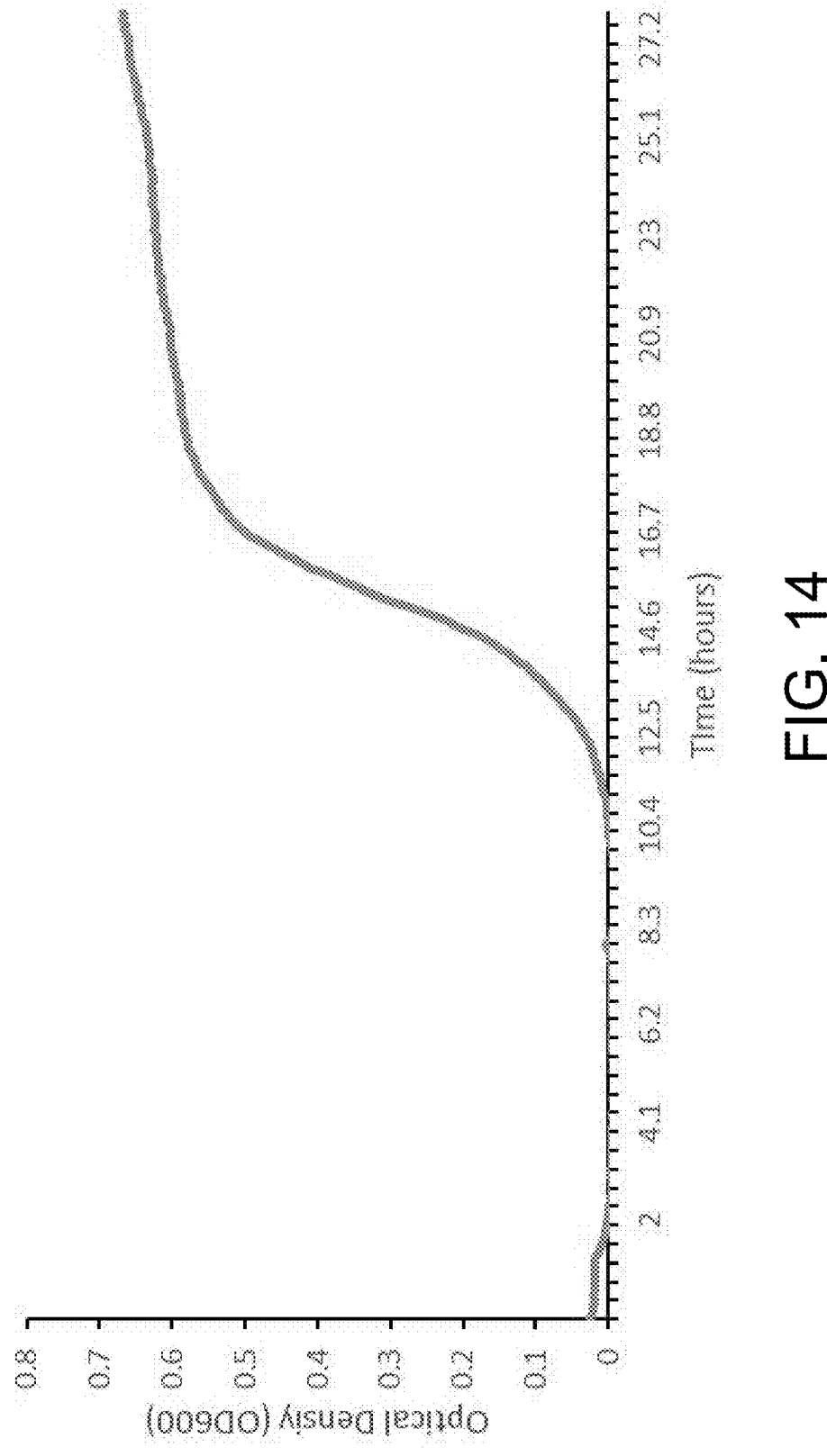
FIG. 14 graphically illustrates bacterial cell growth in phage lysates: sensitive bacterial cells and phage of interest are added at TO, which initiates phage replication and cell lysis; over time, continuous culturing at 37° C., as described in Example 3.

FIG. 14 graphically illustrates representation of bacterial cell growth in phage lysates at optimal bacterial growth temperature. For instance, sensitive bacterial cells and phage of interest are added at TO, which initiates phage replication and cell lysis. Overtime, continuous culturing at 37° C. allows bacteria to mutate and develop resistance to phage infection. Phage resistant mutants divide continuously to repopulate the culture.

FIG. 15 graphically illustrates reduction in bacteria count after phage cultivation. At the end of phage cultivation, live bacteria counts in lysates were reduced by 3-log by cooling the culture to 4° C. after the initial appearance of phage resistant mutant outgrowth when compared to continuous culturing at 37° C. (n=3, student t-test).

FIG. 16 graphically illustrates reduction in bacterial debris pellet weight after phage lysate centrifugation. After centrifugation of phage lysates, bacteria and phages grown continuously at 37° C. exhibited a 33% increase in bacterial debris pellet weight compared to cultures cooled to 4° C. after the initial appearance of phage resistant mutant outgrowth (n=3, student t-test).

FIG. 17 graphically illustrates cooling during phage cultivation does not reduce virus yield. At the end of phage counts were not statistically different between continuous culturing at 37° C. and cooled cultures after the initial appearance of phage resistant mutant outgrowth (n=3, student t-test).

We show that by cooling phage lysates at the point where phage resistant bacteria appear in culture, overall live bacterial cells and debris are significantly reduced at the end of cultivation. This modifies Step 86 in Example 2 to improve the removal of bulk bacterial debris in step 87 (Example 2). This step can be important because it improves all downstream purification steps by having less, for example, endotoxin to remove from phage preparations. In addition, it enhances filtration steps by having less gross debris that clogs the filter membranes. Importantly, there is no reduction in phage yields.

REFERENCES EXAMPLE 1

1 Schooley, R. T. et al. Development and Use of Personalized Bacteriophage-Based Therapeutic Cocktails To Treat a Patient with a Disseminated Resistant *Acinetobacter baumannii* Infection. *Antimicrob Agents Chemother* 61, e00954-00917 (2017).

2 Dedrick, R. M. et al. Engineered bacteriophages for treatment of a patient with a disseminated drug-resistant *Mycobacterium abscessus*. *Nat Med* 25, 730-733 (2019).

3 Onsea, J. et al. Bacteriophage Application for Difficult-to-treat Musculoskeletal Infections: Development of a Standardized Multidisciplinary Treatment Protocol. *Viruses* 11 (2019).

4 Nir-Paz, R. et al. Successful treatment of antibiotic-resistant, poly-microbial bone infection with bacteriophages and antibiotics combination. *Clin Infect Dis* 69, 2015-2018 (2019).

5 Van Norman, G. A. Expanding patient access to investigational drugs: single patient investigational new drug and the "Right to try". *JACC Basic Transl Sci* 3, 280-293 (2018).

6 Svircev, A., Roach, D. R. & Castle, A. Framing the future with bacteriophages in agriculture. *Viruses* 10 (2018).

7 Segall, A. M., Roach, D. R. & Strathdee, S. A. Stronger together? Perspectives on phage-antibiotic synergy in clinical applications of phage therapy. *Curr Opin Microbiol* 51, 46-50 (2019).

8 Moye, Z. D., Woolston, J. & Sulakvelidze, A. Bacteriophage Applications for Food Production and Processing. *Viruses* 10, 205 (2018).

9 Lehman, S. M. et al. Design and Preclinical Development of a Phage Product for the Treatment of Antibiotic-Resistant *Staphylococcus aureus* Infections. *Viruses* 11, 88 (2019).

10 Pirnay, J. P. et al. Quality and safety requirements for sustainable phage therapy products. *Pharm Res* 32, 2173-2179 (2015).

11 Mutti, M. & Corsini, L. Robust approaches for the production of active ingredient and drug product for human phage therapy. *Front Microbiol* 10, 2289 (2019).

12 Kutateladze, M. & Adamia, R. Phage therapy experience at the Eliava Institute. *Med Mal Infect* 38, 426-430 (2008).

13 Letkiewicz, S. et al. The perspectives of the application of phage therapy in chronic bacterial prostatitis. *FEMS Immunol Med Microbiol* 60, 99-112 (2010).

14 Jault, P. et al. Efficacy and tolerability of a cocktail of bacteriophages to treat burn wounds infected by *Pseudomonas aeruginosa* (PhagoBurn): a randomised, controlled, double-blind phase ½ trial. *Lancet Infect Dis* 19, 35-45 (2019).

15 CDC. Antibiotic resistance threats in the United States, 2019 (U.S. Department of Health and Human Services, C D C, 2019).

16 O'Neill, J. Tackling drug-resistant infections globally: Final report and recommendations. (Department of Health, United Kingdom, 2016).

17 d'Herelle, F. Bacteriophage as a treatment in acute medical and surgical infections. *Bulletin of the New York Academy of Medicine* 7, 329-348 (1931).

18 Adams, M. Enumeration of bacteriophage particles. *The Bacteriophages,* 27-34 (1959).

51

19 Walker, D., Roach, D. R. & Debarbieux, L. Phage therapy: awakening a sleeping giant. *Emerging Topics in Life Sciences* 1, 93-103 (2017).

20 Dalpke, A., Frank, J., Peter, M. & Heeg, K. Activation of toll-like receptor 9 by DNA from different bacterial species. *Infect Immun* 74, 940-946 (2006).

21 Sweere, J. M. et al. Bacteriophage trigger antiviral immunity and prevent clearance of bacterial infection. *Science* 363 (2019).

22 Capparelli, R., Parlato, M., Borriello, G., Salvatore, P. & Iannelli, D. Experimental phage therapy against *Staphylococcus aureus* in mice. *Antimicrob Agents Chemother* 51, 2765-2773 (2007).

23 Forti, F. et al. Design of a Broad-Range Bacteriophage Cocktail That Reduces *Pseudomonas aeruginosa* Biofilms and Treats Acute Infections in Two Animal Models. *Antimicrob Agents Chemother* 62 (2018).

24 Roach, D. R. et al. Synergy between the Host Immune System and Bacteriophage Is Essential for Successful Phage Therapy against an Acute Respiratory Pathogen. *Cell host & microbe* 22, 38-47 e34 (2017).

25 Chibani-Chennoufi, S. et al. In vitro and in vivo bacteriolytic activities of *Escherichia coli* phages: implications for phage therapy. *Antimicrob Agents Chemother* 48, 2558-2569 (2004).

26 Yamamoto, K. R., Alberts, B. M., Benzinger, R., Lawhorne, L. & Treiber, G. Rapid bacteriophage sedimentation in the presence of polyethylene glycol and its application to large-scale virus purification. *Virology* 40, 734-744 (1970).

27 Bachrach, U. & Friedmann, A. Practical procedures for the purification of bacterial viruses. *Appl Microbiol* 22, 706-715 (1971).

28 Ackermann, H. W. et al. Guidelines for bacteriophage characterization. *Advances in virus research* 23, 1-24 (1978).

29 Boratynski, J. et al. Preparation of endotoxin-free bacteriophages. *Cell Mol Biol Lett* 9, 253-259 (2004).

30 Gill, J. J. & Hyman, P. Phage choice, isolation, and preparation for phage therapy. *Curr Pharm Biotechnol* 11, 2-14 (2010).

31 Bourdin, G. et al. Amplification and purification of T4-like *Escherichia coli* phages for phage therapy: from laboratory to pilot scale. *Appl Environ Microbiol* 80, 1469-1476 (2014).

32 Bonilla, N. et al. Phage on tap-a quick and efficient protocol for the preparation of bacteriophage laboratory stocks. *PeerJ* 4, e2261 (2016).

33 Van Belleghem, J. D., Merabishvili, M., Vergauwen, B., Lavigne, R. & Vaneechoutte, M. A comparative study of different strategies for removal of endotoxins from bacteriophage preparations. *Journal of microbiological methods* 132, 153-159 (2017).

34 Szermer-Olearnik, B. & Boratynski, J. Removal of endotoxins from bacteriophage preparations by extraction with organic solvents. *PLoS One* 10, e0122672 (2015).

35 Van Belleghem, J. D., Dabrowska, K., Vaneechoutte, M., Barr, J. J. & Bollyky, P. L. Interactions between Bacteriophage, Bacteria, and the Mammalian Immune System. *Viruses* 11 (2018).

36 Gogokhia, L. et al. Expansion of Bacteriophages Is Linked to Aggravated Intestinal Inflammation and Colitis. *Cell host & microbe* 25, 285-299 e288 (2019).

37 Navarro, F. & Muniesa, M. Phages in the Human Body. *Front Microbiol* 8, 566 (2017).

38 Pirnay, J. P. et al. The Magistral Phage. *Viruses* 10 (2018).

52

39 Chan, B. K. et al. Phage treatment of an aortic graft infected with *Pseudomonas aeruginosa*. *Evol Med Public Health* 2018, 60-66 (2018).

40 FDA. Guidance for industry: pyrogen and endotoxins testing: questions and answers (U.S. Department of Health and Human Services, FDA, 2012).

41 Spaulding, A. R. et al. Staphylococcal and streptococcal superantigen exotoxins. *Clin Microbiol Rev* 26, 422-447 (2013).

42 Freeman, V. J. Studies on the virulence of bacteriophage-infected strains of *Corynebacterium diphtheriae*. *J Bacteriol* 61, 675-688 (1951).

43 Waldor, M. K. & Mekalanos, J. J. Lysogenic conversion by a filamentous phage encoding cholera toxin. *Science* 272, 1910-1914 (1996).

44 Hatano, M., Nakamura, K. & Kurokawa, M. Isolation of a new temperature phage causing the lysogenic conversion in *Corynebacterium diphtheriae*. *Jpn J Microbiol* 3, 301-311 (1959).

45 Weeks, C. R. & Ferretti, J. J. The gene for type A streptococcal exotoxin (erythrogenic toxin) is located in bacteriophage T12. *Infect. Immun.* 46, 531-536 (1984).

46 Schmidt, H. Shiga-toxin-converting bacteriophages. *Res Microbiol* 152, 687-695 (2001).

47 Plunkett, G., Rose, D. J., Durfee, T. J. & Blattner, F. R. Sequence of Shiga Toxin 2 Phage 933W from *Escherichia coli* 0157:H7: Shiga Toxin as a Phage Late-Gene Product. *J. Bacteriol.* 181, 1767-1778 (1999).

48 Cobian Guemes, A. G. et al. Cystic fibrosis rapid response: translating multi-omics data into clinically relevant information. *MBio* 10 (2019).

49 Eklund, M. W., Poysky, F. T., Reed, S. M. & Smith, C. A. Bacteriophage and the toxigenicity of *Clostridium botulinum* type C. *Science* 172, 480-482 (1971).

50 Brussow, H., Canchaya, C. & Hardt, W. D. Phages and the evolution of bacterial pathogens: from genomic rearrangements to lysogenic conversion. *Microbiol Mol Biol Rev* 68, 560-602, table of contents (2004).

51 Wagner, P. L. & Waldor, M. K. Bacteriophage control of bacterial virulence. *Infect Immun* 70, 3985-3993 (2002).

52 Brown-Jaque, M. et al. Antibiotic resistance genes in phage particles isolated from human faeces and induced from clinical bacterial isolates. *Int J Antimicrob Agents* 51, 434-442 (2018).

53 Purdy, A., Rohwer, F., Edwards, R., Azam, F. & Bartlett, D. H. A glimpse into the expanded genome content of *Vibrio cholerae* through identification of genes present in environmental strains. *J Bacteriol* 187, 2992-3001 (2005).

54 Enault, F. et al. Phages rarely encode antibiotic resistance genes: a cautionary tale for virome analyses. *ISMS J* 11, 237-247 (2017).

55 Billard-Pomares, T. et al. Characterization of a P1-like bacteriophage carrying an SHV-2 extended-spectrum beta-lactamase from an *Escherichia coli* strain. *Antimicrob Agents Chemother* 58, 6550-6557 (2014).

56 Zhou, W., Liu, L., Feng, Y. & Zong, Z. A P7 Phage-Like Plasmid Carrying mcr-1 in an ST15 *Klebsiella pneumoniae* Clinical Isolate. *Front Microbiol* 9, 11 (2018).

57 Aziz, R. K. et al. Mosaic prophages with horizontally acquired genes account for the emergence and diversification of the globally disseminated M1T1 clone of *Streptococcus pyogenes*. *J Bacteriol* 187, 3311-3318 (2005).

58 Lacey, J. A., Johanesen, P. A., Lyras, D. & Moore, R. J. In silico identification of novel toxin homologs and associated mobile genetic elements in *Clostridium perfringens*. *Pathogens* 8 (2019).

59 Nguyen, M. et al. Using machine learning to predict antimicrobial MICs and associated genomic features for nontyphoidal *Salmonella. J Clin Microbiol* 57 (2019).

60 Seemann, T. Abricate.

61 Jia, B. et al. CARD 2017: expansion and model-centric curation of the comprehensive antibiotic resistance database. *Nucleic Acids Res* 45, D566-D573 (2017).

62 Zankari, E. et al. Identification of acquired antimicrobial resistance genes. *J Antimicrob Chemother* 67, 2640-2644 (2012).

63 Feldgarden, M. et al. Validating the AMRFinder Tool and Resistance Gene Database by Using Antimicrobial Resistance Genotype-Phenotype Correlations in a Collection of Isolates. *Antimicrob Agents Chemother* 63 (2019).

64 Gupta, S. K. et al. ARG-ANNOT, a new bioinformatic tool to discover antibiotic resistance genes in bacterial genomes. *Antimicrob Agents Chemother* 58, 212-220 (2014).

65 Chen, L., Zheng, D., Liu, B., Yang, J. & Jin, Q. VFDB 2016: hierarchical and refined dataset for big data analysis—10 years on. *Nucleic Acids Res* 44, D694-697 (2016).

66 Carattoli, A. et al. In silico detection and typing of plasmids using PlasmidFinder and plasmid multilocus sequence typing. *Antimicrob Agents Chemother* 58, 3895-3903 (2014).

67 Edwards, R. A., McNair, K., Faust, K., Raes, J. & Dutilh, B. E. Computational approaches to predict bacteriophage-host relationships. *FEMS Microbiol Rev* 40, 258-272 (2016).

68 McNair, K. et al. Phage Genome Annotation Using the RAST Pipeline in *Bacteriophages: Methods and Protocols, Volume* 3. Vol. 1681 (eds Martha R. J. Clokie, Andrew M. Kropinski, & Rob Lavigne) 231-238 (Springer New York, 2018).

69 Philipson, C. W. et al. Characterizing Phage Genomes for Therapeutic Applications. *Viruses* 10 (2018).

70 Kutter, E. Phage host range and efficiency of plating in *Bacteriophages.* 141-149 (Springer, 2009).

71 Erickson, H. P. Size and shape of protein molecules at the nanometer level determined by sedimentation, gel filtration, and electron microscopy. *Biol Proced Online* 11, 32-51 (2009).

72 Brakke, M. K. Density gradient centrifugation: a new separation technique. *J Am Chem Soc* 73, 1847-1848 (1951).

73 Ritzen, U., Rotticci-Mulder, J., Stromberg, P. & Schmidt, S. R. Endotoxin reduction in monoclonal antibody preparations using arginine. *J Chromatogr B Analyt Technol Biomed Life Sci* 856, 343-347 (2007).

74 Petsch, D. & Anspach, F. B. Endotoxin removal from protein solutions. *J Biotechnol* 76, 97-119 (2000).

75 Melnikov, P. & Zanoni, L. Z. Clinical effects of cesium intake. *Biological trace element research* 135, 1-9 (2010).

76 Centeno, J. A. et al. Blood and tissue concentration of cesium after exposure to cesium chloride: a report of two cases. *Biological trace element research* 94, 97-104 (2003).

77 Mancuso, F., Shi, J. & Malik, D. J. High Throughput Manufacturing of Bacteriophages Using Continuous Stirred Tank Bioreactors Connected in Series to Ensure Optimum Host Bacteria Physiology for Phage Production. *Viruses* 10, 537 (2018).

78 Moir, D. T., Ming, D., Opperman, T., Schweizer, H. P. & Bowlin, T. L. A high-throughput, homogeneous, bioluminescent assay for *Pseudomonas aeruginosa* gyrase inhibitors and other DNA-damaging agents. *J Biomol Screen* 12, 855-864 (2007).

79 Summer, E. J. Preparation of a phage DNA fragment library for whole genome shotgun sequencing. *Methods Mol Biol* 502, 27-46 (2009).

80 Koren, S. et al. Canu: scalable and accurate long-read assembly via adaptive k-mer weighting and repeat separation. *Genome Res* 27, 722-736 (2017).

81 McNair, K., Bailey, B. A. & Edwards, R. A. PHACTS, a computational approach to classifying the lifestyle of phages. *Bioinformatics* 28, 614-618 (2012).

82 Henry, M., Lavigne, R. & Debarbieux, L. Predicting in vivo efficacy of therapeutic bacteriophages used to treat pulmonary infections. *Antimicrob Agents Chemother* 57, 5961-5968 (2013).

REFERENCES—EXAMPLE 2

1 Schooley, R. T. et al. Development and use of personalized bacteriophage-based therapeutic cocktails to treat a patient with a disseminated resistant *Acinetobacter baumannii* infection. *Antimicrob Agents Chemother* 61, e00954-00917, doi:10.1128/AAC.00954-17 (2017).

2 Dedrick, R. M. et al. Engineered bacteriophages for treatment of a patient with a disseminated drug-resistant *Mycobacterium abscessus. Nat Med* 25, 730-733, doi: 10.1038/s41591-019-0437-z (2019).

3 Onsea, J. et al. Bacteriophage application for difficult-to-treat musculoskeletal infections: development of a standardized multidisciplinary treatment protocol. *Viruses* 11, doi:10.3390/v11100891 (2019).

4 Nir-Paz, R. et al. Successful treatment of antibiotic resistant poly-microbial bone infection with bacteriophages and antibiotics combination. *Clin Infect Dis*, doi:10.1093/cid/ciz222 (2019).

5 Van Norman, G. A. Expanding patient access to investigational drugs: single patient investigational new drug and the "right to try". *JACC Basic Transl Sci* 3, 280-293, doi:10.1016/j.jacbts.2017.11.007 (2018).

6 Svircev, A., Roach, D. & Castle, A. Framing the future with bacteriophages in agriculture. *Viruses* 10, doi: 10.3390/v10050218 (2018).

7 Segall, A. M., et al. Stronger together? Perspectives on phage-antibiotic synergy in clinical applications of phage therapy. *Current opinion in microbiology* 51, 46-50, doi: 10.1016/j.mib.2019.03.005 (2019).

8 Moye, Z. D., et al. Bacteriophage applications for food production and processing. *Viruses* 10, 205 (2018).

9 Lehman, S. M. et al. Design and preclinical development of a phage product for the treatment of antibiotic-resistant *Staphylococcus aureus* infections. *Viruses* 11, 88, doi: 10.3390/v11010088 (2019).

10 Pirnay, J.-P. et al. Quality and safety requirements for sustainable phage therapy products. *Pharmaceutical Research* 32, 2173-2179, doi:10.1007/s11095-014-1617-7 (2015).

11 Mutti, M. & Corsini, L. Robust approaches for the production of active ingredient and drug product for human phage therapy. *Frontiers in Microbiology* 10, doi:10.3389/fmicb.2019.02289 (2019).

12 Kutateladze, M. & Adamia, R. Phage therapy experience at the Eliava Institute. *Médecine et Maladies Infectieuses* 38, 426-430, doi:10.1016/j.medma1.2008.06.023 (2008).

13 Letkiewicz, S. et al. The perspectives of the application of phage therapy in chronic bacterial prostatitis. *FEMS Immunology & Medical Microbiology* 60, 99-112, doi: 10.1111/j.1574-695X.2010.00723.x (2010).

14 Jault, P. et al. Efficacy and tolerability of a cocktail of bacteriophages to treat burn wounds infected by

*Pseudomonas aeruginosa* (PhagoBurn): a randomised, controlled, double-blind phase ½ trial. *The Lancet Infectious Diseases* 19, 35-45, doi:10.1016/S1473-3099(18)30482-1 (2019).

15 CDC. (ed CDC U.S. Department of Health and Human Services) (Antibiotic Resistance Coordination and Strategy Unit within the Division of Healthcare Quality Promotion, Atlanta, GA, 2019).

16 O'Neill, J. Tackling drug-resistant infections globally: final report and recommendations. (Department of Health, United Kingdom, 2016).

17 d'Hérelle, F. L'étude d'une maladie: le choléra, maladie à paradoxes. (Rouge, 1946).

18 Adams, M. Enumeration of bacteriophage particles. *The Bacteriophages,* 27-34 (1959).

19 Roach, D. R. & Debarbieux, L. Phage therapy: awakening a sleeping giant. *Emerging Topics in Life Sciences* 1, 93-103, doi:10.1042/ETLS20170002 (2017).

20 Dalpke, A., Frank, J., Peter, M. & Heeg, K. Activation of toll-like receptor 9 by DNA from different bacterial species. *Infection and immunity* 74, 940-946, doi:10.1128/IAI.74.2.940-946.2006 (2006).

21 Sweere, J. M. et al. Bacteriophage trigger antiviral immunity and prevent clearance of bacterial infection. *Science* 363, doi:10.1126/science.aat9691 (2019).

22 Opal, S. M. Endotoxins and other sepsis triggers. *Contributions to nephrology* 167, 14-24, doi:10.1159/000315915 (2010).

23 Capparelli, R., Parlato, M., Borriello, G., Salvatore, P. & Iannelli, D. Experimental phage therapy against *Staphylococcus aureus* in mice. *Antimicrobial Agents and Chemotherapy* 51, 2765, doi:10.1128/AAC.01513-06 (2007).

24 Forti, F. et al. Design of a broad-range bacteriophage cocktail that reduces *Pseudomonas aeruginosa* biofilms and treats acute infections in two animal models. *Antimicrob Agents Chemother* 62, doi:10.1128/AAC.02573-17 (2018).

25 Roach, D. R. et al. Synergy between the host immune system and bacteriophage Is essential for successful phage therapy against an acute respiratory pathogen. *Cell host & microbe* 22, 38-47 e34, doi:10.1016/j.chom.2017.06.018 (2017).

26 Chibani-Chennoufi, S. et al. In vitro and in vivo bacteriolytic activities of *Escherichia coli* phages: implications for phage therapy. *Antimicrobial Agents and Chemotherapy* 48, 2558, doi:10.1128/AAC.48.7.2558-2569.2004 (2004).

27 Yamamoto, K. R., et al. Rapid bacteriophage sedimentation in the presence of polyethylene glycol and its application to large-scale virus purification. *Virology* 40, 734-744, doi:10.1016/0042-6822(70)90218-7 (1970).

28 Bachrach, U. & Friedmann, A. Practical procedures for the purification of bacterial viruses. *Appl Microbiol* 22, 706-715 (1971).

29 Ackermann, H. W. et al. Guidelines for bacteriophage characterization. *Advances in virus research* 23, 1-24 (1978).

30 Boratynski, J. et al. Preparation of endotoxin-free bacteriophages. *Cell Mol Biol Lett* 9, 253-259 (2004).

31 Gill, J. & Hyman, P. Phage choice, isolation, and preparation for phage therapy. *Current Pharmaceutical Biotechnology* 11, 2-14, doi:10.2174/138920110790725311 (2010).

32 Bourdin, G. et al. Amplification and purification of T4-like *Escherichia coli* phages for phage therapy: from laboratory to pilot scale. *Appl Environ Microbiol* 80, 1469-1476, doi:10.1128/aem.03357-13 (2014).

33 Bonilla, N. et al. Phage on tap-a quick and efficient protocol for the preparation of bacteriophage laboratory stocks. *PeerJ* 4, e2261, doi:10.7717/peerj.2261 (2016).

34 Van Belleghem, J. D., et al. A comparative study of different strategies for removal of endotoxins from bacteriophage preparations. *Journal of microbiological methods* 132, 153-159, doi:10.1016/j.mimet.2016.11.020 (2017).

35 Van Belleghem, J. D., et al. Interactions between bacteriophage, bacteria, and the mammalian immune system. *Viruses* 11, doi:10.3390/v11010010 (2018).

36 Gogokhia, L. et al. Expansion of bacteriophages is linked to aggravated intestinal inflammation and colitis. *Cell host & microbe* 25, 285-299 e288, doi:10.1016/j.chom.2019.01.008 (2019).

37 An, T. W., et al. The immune-enhancing effect of the *Cronobacter sakazakii* ES2 phage results in the activation of nuclear factor-kappaB and dendritic cell maturation via the activation of IL-12p40 in the mouse bone marrow. *Immunol Lett* 157, 1-8, doi:10.1016/j.imlet.2013.10.007 (2014).

38 Van Belleghem, J. D., et al. Pro- and anti-inflammatory responses of peripheral blood mononuclear cells induced by *Staphylococcus aureus* and *Pseudomonas aeruginosa* phages. *Sci Rep* 7, 8004, doi:10.1038/s41598-017-08336-9 (2017).

39 Chan, B. K. et al. Phage treatment of an aortic graft infected with *Pseudomonas aeruginosa. Evolution, Medicine, and Public Health* 2018, 60-66, doi:10.1093/emph/eoy005 (2018).

40 Pirnay, J. P. et al. The magistral phage. *Viruses* 10, doi:10.3390/v10020064 (2018).

41 FDA. (ed U.S. Department of Health and Human Services Food and Drug Administration) (Office of Communications, Division of Drug Information, Silver Spring and Rockville, MD, 2012).

42 Spaulding, A. R. et al. Staphylococcal and streptococcal superantigen exotoxins. *Clin Microbiol Rev* 26, 422-447, doi:10.1128/CMR.00104-12 (2013).

43 Carlson, K. *Working with bacteriophages: common techniques and methodological approaches.* Vol. 1 (CRC press Boca Raton, FL, 2005).

44 Davidson, I. W., Sumner, D. D. & Parker, J. C. Chloroform: a review of its metabolism, teratogenic, mutagenic, and carcinogenic potential. *Drug and chemical toxicology* 5, 1-87, doi:10.3109/01480548209017822 (1982).

45 Szermer-Olearnik, B. & Boratyński, J. Removal of endotoxins from bacteriophage preparations by extraction with organic solvents. *PLOS ONE* 10, e0122672, doi:10.1371/journal.pone.0122672 (2015).

46 Melnikov, P. & Zanoni, L. Z. Clinical effects of cesium intake. *Biological trace element research* 135, 1-9, doi:10.1007/s12011-009-8486-7 (2010).

47 Centeno, J. A. et al. Blood and tissue concentration of cesium after exposure to cesium chloride: a report of two cases. *Biological trace element research* 94, 97-104, doi:10.1385/BTER:94:2:97 (2003).

48 Mancuso, F., Shi, J. & Malik, D. J. High throughput manufacturing of bacteriophages using continuous stirred tank bioreactors connected in series to ensure optimum host bacteria physiology for phage production. *Viruses* 10, 537, doi:10.3390/v10100537 (2018).

49 Edelman, D. C. & Barletta, J. Real-time PCR provides improved detection and titer determination of bacteriophage. *BioTechniques* 35, 368-375, doi:10.2144/03352n02 (2003).

50 Anderson, B. et al. Enumeration of bacteriophage particles: comparative analysis of the traditional plaque assay and real-time QPCR- and nanosight-based assays. *Bacteriophage* 1, 86-93, doi:10.4161/bact.1.2.15456 (2011).

51 Freeman, V. J. Studies on the virulence of bacteriophage-infected strains of *Corynebacterium diphtheriae. J Bacteriol* 61, 675-688 (1951).

52 Waldor, M. K. & Mekalanos, J. J. Lysogenic conversion by a filamentous phage encoding cholera toxin. *Science* 272, 1910-1914, doi:10.1126/science.272.5270.1910 (1996).

53 Hatano, M., Nakamura, K. & Kurokawa, M. Isolation of a new temperature phage causing the lysogenic conversion in *Corynebacterium diphtheriae. Jpn J Microbiol* 3, 301-311, doi:10.1111/j.1348-0421.1959.tb00127.x (1959).

54 Weeks, C. R. & Ferretti, J. J. The gene for type-A Streptococcal exotoxin (erythrogenic toxin) is located in bacteriophage-T12. *Infection and Immunity* 46, 531-536, doi:Doi 10.1128/Iai.46.2.531-536.1984 (1984).

55 Schmidt, H. Shiga-toxin-converting bacteriophages. *Res Microbiol* 152, 687-695, doi:10.1016/s0923-2508(01)01249-9 (2001).

56 Plunkett, G., Rose, D. J., Durfee, T. J. & Blattner, F. R. Sequence of shiga toxin 2 phage 933W from *Escherichia coli* 0157:H7: shiga toxin as a phage late-gene product. *J. Bacteriol.* 181, 1767-1778 (1999).

57 Cobian Guemes, A. G. et al. Cystic fibrosis rapid response: translating multi-omics data into clinically relevant information. *MBio* 10, doi:10.1128/mBio.00431-19 (2019).

58 Eklund, M. W., et al. Bacteriophage and the toxigenicity of *Clostridium botulinum* type C. *Science* 172, 480-482, doi:10.1126/science.172.3982.480 (1971).

59 Brussow, H., et al. Phages and the evolution of bacterial pathogens: from genomic rearrangements to lysogenic conversion. *Microbiol Mot Blot Rev* 68, 560-602, table of contents, doi:10.1128/MMBR.68.3.560-602.2004 (2004).

60 Wagner, P. L. & Waldor, M. K. Bacteriophage control of bacterial virulence. *Infect Immun* 70, 3985-3993, doi:10.1128/iai.70.8.3985-3993.2002 (2002).

61 Brown-Jaque, M. et al. Antibiotic resistance genes in phage particles isolated from human faeces and induced from clinical bacterial isolates. *Int J Antimicrob Agents* 51, 434-442, doi:10.1016/j.ijantimicag.2017.11.014 (2018).

62 Purdy, A., Rohwer, F., Edwards, R., Azam, F. & Bartlett, D. H. A glimpse into the expanded genome content of *Vibrio cholerae* through identification of genes present in environmental strains. *J Bacteriol* 187, 2992-3001, doi:10.1128/JB.187.9.2992-3001.2005 (2005).

63 Enault, F. et al. Phages rarely encode antibiotic resistance genes: a cautionary tale for virome analyses. *ISME J* 11, 237-247, doi:10.1038/ismej.2016.90 (2017).

64 Billard-Pomares, T. et al. Characterization of a P1-like bacteriophage carrying an SHV-2 extended-spectrum beta-lactamase from an *Escherichia coli* strain. *Antimicrob Agents Chemother* 58, 6550-6557, doi:10.1128/AAC.03183-14 (2014).

65 Zhou, W., Liu, L., Feng, Y. & Zong, Z. A P7 phage-like plasmid carrying mcr-1 in an ST15 *Klebsiella pneumoniae* clinical isolate. *Front Microbiol* 9, 11, doi:10.3389/fmicb.2018.00011 (2018).

66 Aziz, R. K. et al. Mosaic prophages with horizontally acquired genes account for the emergence and diversification of the globally disseminated M1T1 clone of *Strep-*

*tococcus pyogenes. J Bacteriol* 187, 3311-3318, doi:10.1128/JB.187.10.3311-3318.2005 (2005).

67 Lacey, J. A., Johanesen, P. A., Lyras, D. & Moore, R. J. In silico identification of novel toxin homologs and associated mobile genetic elements in *Clostridium perfringens.* Pathogens 8, doi:10.3390/pathogens8010016 (2019).

68 Nguyen, M. et al. Using machine learning to predict antimicrobial MICs and associated genomic features for nontyphoidal *Salmonella. J Clin Microbiol* 57, doi:10.1128/JCM.01260-18 (2019).

69 Jia, B. et al. CARD 2017: expansion and model-centric curation of the comprehensive antibiotic resistance database. *Nucleic Acids Res* 45, D566-D573, doi:10.1093/nar/gkw1004 (2017).

70 Zankari, E. et al. Identification of acquired antimicrobial resistance genes. *J Antimicrob Chemother* 67, 2640-2644, doi:10.1093/jac/dks261 (2012).

71 Feldgarden, M. et al. Validating the AMRFinder Tool and Resistance Gene Database by using antimicrobial resistance genotype-phenotype correlations in a collection of isolates. *Antimicrob Agents Chemother* 63, doi:10.1128/AAC.00483-19

72 Gupta, S. K. et al. ARG-ANNOT, a new bioinformatic tool to discover antibiotic resistance genes in bacterial genomes. *Antimicrob Agents Chemother* 58, 212-220, doi:10.1128/AAC.01310-13 (2014).

73 Chen, L., Zheng, D., Liu, B., Yang, J. & Jin, Q. VFDB 2016: hierarchical and refined dataset for big data analysis—10 years on. *Nucleic Acids Res* 44, D694-697, doi:10.1093/nar/gkv1239 (2016).

74 Carattoli, A. et al. In silico detection and typing of plasmids using PlasmidFinder and plasmid multilocus sequence typing. *Antimicrob Agents Chemother* 58, 3895-3903, doi:10.1128/AAC.02412-14 (2014).

75 Beaulaurier, J. et al. Assembly-free single-molecule sequencing recovers complete virus genomes from natural microbial communities. *Genome Res* 30, 437-446, doi:10.1101/gr.251686.119 (2020).

76 Wattam, A. R. et al. Improvements to PATRIC, the all-bacterial bioinformatics database and analysis resource center. *Nucleic Acids Res* 45, D535-d542, doi:10.1093/nar/gkw1017 (2017).

77 McNair, K., Bailey, B. A. & Edwards, R. A. PHACTS, a computational approach to classifying the lifestyle of phages. *Bioinformatics* 28, 614-618, doi:10.1093/bioinformatics/bts014 (2012).

78 Edwards, R. A., McNair, K., Faust, K., Raes, J. & Dutilh, B. E. Computational approaches to predict bacteriophage-host relationships. *FEMS Microbiol Rev* 40, 258-272, doi:10.1093/femsre/fuv048 (2016).

79 McNair, K. et al. in *Bacteriophages: Methods and Protocols,* Volume 3 Vol. 1681 (eds Martha R. J. Clokie, Andrew M. Kropinski, & Rob Lavigne) 231-238 (Springer New York, 2018).

80 Philipson, C. W. et al. Characterizing phage genomes for therapeutic applications. *Viruses* 10, doi:10.3390/v10040188 (2018).

81 Kutter, E. in *Bacteriophages* 141-149 (Springer, 2009).

82 Erickson, H. P. Size and shape of protein molecules at the nanometer level determined by sedimentation, gel filtration, and electron microscopy. *Biological Procedures Online* 11, 32, doi:10.1007/s12575-009-9008-x (2009).

83 Brakke, M. K. Density gradient centrifugation—a new separation technique. *Journal of the American Chemical Society* 73, 1847-1848, doi:DOI 10.1021/ja01148a508 (1951).

84 Petsch, D. & Anspach, F. B. Endotoxin removal from protein solutions. *J Biotechnol* 76, 97-119, doi:10.1016/s0168-1656(99)00185-6 (2000).

85 Barr, J. J. et al. Bacteriophage adhering to mucus provide a non-host-derived immunity. *Proceedings of the National Academy of Sciences* 110, 10771, doi:10.1073/pnas.1305923110 (2013).

86 Bocian, K. et al. The effects of T4 and A3/R bacteriophages on differentiation of human myeloid dendritic cells. *Frontiers in Microbiology* 7, doi:10.3389/fmicb.2016.01267 (2016).

87 Riss, T. L. et al. in *Assay Guidance Manual* (eds G. S. Sittampalam et al.) (Eli Lilly & Company and the National Center for Advancing Translational Sciences, 2004).

88 Moir, D. T., Ming, D., Opperman, T., Schweizer, H. P. & Bowlin, T. L. A high-throughput, homogeneous, bioluminescent assay for *Pseudomonas aeruginosa* gyrase inhibitors and other DNA-damaging agents. *Journal of Biomolecular Screening* 12, 855-864, doi:10.1177/1087057107304729 (2007).

89 Van Twest, R. & Kropinski, A. M. Bacteriophage enrichment from water and soil. *Methods Mol Biol* 501, 15-21, doi:10.1007/978-1-60327-164-6_2 (2009).

90 Summer, E. J. Preparation of a phage DNA fragment library for whole genome shotgun sequencing. *Methods Mol Biol* 502, 27-46, doi:10.1007/978-1-60327-565-1_4 (2009).

91 Koren, S. et al. Canu: scalable and accurate long-read assembly via adaptive k-mer weighting and repeat separation. *Genome Res* 27, 722-736, doi:10.1101/gr.215087.116 (2017).

92 Henry, M., Lavigne, R. & Debarbieux, L. Predicting in vivo efficacy of therapeutic bacteriophages used to treat pulmonary infections. *Antimicrobial agents and chemotherapy* 57, 5961-5968, doi:10.1128/AAC.01596-13 (2013).

93 Boulanger, P. in *Bacteriophages: Methods and Protocols, Volume 2 Molecular and Applied Aspects* (eds Martha R. J. Clokie & Andrew M. Kropinski) 227-238 (Humana Press, 2009).

94 Trend, S. et al. Use of a primary epithelial cell screening tool to investigate phage therapy in cystic fibrosis. *Front Pharmacol* 9, 1330, doi:10.3389/fphar.2018.01330 (2018).

95 Roach, D. R., et al. Host exopolysaccharide quantity and composition impacts bacteriophage pathogenesis of *Erwinia amylovora*. *Applied and Environmental Microbiology*, AEM.00067-00013, doi:10.1128/AEM.00067-13 (2013).

A number of embodiments of the invention have been described. Nevertheless, it can be understood that various modifications may be made without departing from the spirit and scope of the invention. Accordingly, other embodiments are within the scope of the following claims.

What is claimed is:

1. A method for purifying a bacteriophage from a sample comprising unpurified bacteriophages comprising or contaminated with a bacterial product or contaminant and generating a bacterial product- or contaminant-free preparation of the bacteriophage, comprising:

(a) providing a sample comprising an unpurified bacteriophage, wherein the sample comprises a bacteriophage lysate or culture, and to provide a sample, the lysate or culture is cooled to between 4° C. to 37° C., at the point where bacteriophage-insensitive or bacteriophage-resistant bacteria appear in the lysate or the culture; and (b)

(i)

(1) amplifying bacteriophage in the unpurified bacteriophage sample by cultivating in a culture or an enrichment medium for between 18 to 24 hours, between 20 to 22 hours, or between 15 to 30 hours, and then (2) removing bacterial contaminants by a process comprising high-speed centrifugation at 8,000×g, or at least 8,000×g, to pellet bacterial contaminants; or (ii)

(1) removing bacterial contaminants by a process comprising high-speed centrifugation at 8,000×g, or at least 8,000×g to pellet bacterial contaminants, and then (2) amplifying bacteriophage in the unpurified bacteriophage sample by cultivating in a culture or an enrichment medium for between 18 to 24 hours, between 20 to 22 hours, or between 15 to 30 hours; and (c) filtering the sample with:

(i) a dead-end microfiltration process comprising inline stepwise 0.8, 0.45, 0.40, and 0.22 μm membrane filtration, or (ii) a pressure-driven cross-flow ultrafiltration (CFF) comprising a molecular weight cut-off (MWCO) at 100 kDa, wherein a membrane pore size of 100 kDa provides the ability to filter out an equivalent of a spherical particle with a 3 nm diameter, thereby having the ability to retain most bacteriophages, wherein any material smaller than a cross-flow membrane pore passes through the membrane, while bacteriophage particles that do not pass through the membrane remain in the retentate stream, and the CFF with a 100 kDa membrane pore size removes both free endotoxins 10 kDa in size, and exotoxins smaller than 30 kDa, and a membrane pore size of 100 kDa retains an equivalent to a spherical particle with a 3 nm diameter, thereby retaining bacteriophages, thereby generating a bacterial product- or contaminant-free preparation of bacteriophage.

2. The method of claim 1, wherein preparation of the bacteriophage results in a sufficiently lowered endotoxin level such that when administering a bacteriophage dose to a patient the exposure of the patient to endotoxin is below 5.5 EU·kg−1·h−1, or below 5.0 EU·kg·h−1.

3. The method of claim 1, wherein the bacterial product- or contaminant free preparation of bacteriophage comprises at least 300 treatment doses of bacteriophage, wherein each treatment dose comprises $10^9$ PFU, $10^{10}$ PFU, $10^{11}$ PFU, or $10^{12}$ PFU, or more per dose.

4. The method of claim 1, wherein in step (a) the sample is generated by adding bacteriophage to a bacterial culture in a mid-log stage of bacterial growth.

5. The method of claim 1, further comprising formulating a pharmaceutical preparation or formulation by incorporating or mixing the bacterial product- or contaminant-free preparation of bacteriophage generated by claim 2 into the pharmaceutical preparation or formulation.

6. The method of claim 5, wherein the pharmaceutical preparation or formulation is formulated for enteral or parenteral administration.

7. The method of claim 5, wherein the pharmaceutical preparation or formulation is formulated for administration intravenously, by injection, subcutaneously, transdermally, intramuscularly, orally, parenterally, by inhalation spray, nasally, topically, intrathecally, intracerebrally, epidurally, intracranially, vaginally or rectally.

8. The method of claim 5, wherein the pharmaceutical preparation or formulation is formulated as a lyophilate, a tablet, a pill, a powder, a dragee, a capsule, a liquid, a lozenge, a gel, a syrup, a slurry or a suspension.

9. The method of claim 5, wherein the pharmaceutical preparation or formulation further comprises a pharmaceutically acceptable excipient.

10. The method of claim 5, wherein the bacterial product- or contaminant-free preparation of bacteriophage is dissolved or diluted in sterile saline, water, polyethylene glycol, propylene glycol, ethanol, a plant-derived oil, tragacanth gum, a buffer or any combination thereof.

11. The method of claim 10, wherein the plant-derived oil comprises safflower oil, corn oil, peanut oil, cottonseed oil, sesame oil or any combination thereof.

12. The method of claim 1, wherein the bacterial or contaminant comprises a bacterial endotoxin.

13. The method of claim 1, further comprising performing density gradient ultracentrifugation on the generated purified bacterial product- or contaminant-free preparation of bacteriophage, wherein the cesium chloride density gradient ultracentrifugation comprises use of cesium chloride at d=1.6, 1.5, and 1.3, and ultracentrifugation at 28,000×g, to retain bacteriophage in a single density gradient band, followed by extraction or removal of the single density gradient cesium chloride band that comprises bacteriophage from the cesium chloride density gradient.

14. The method of claim 13, further comprising dialyzing the extracted or removed single density gradient cesium chloride band that comprises bacteriophage in a sterile buffered saline, or a sterile phosphate buffered saline.

15. The method of claim 14, further comprising subjecting the dialyzed bacteriophage to lipopolysaccharide-affinity chromatography to remove bacterial products or contaminants, or endotoxins from the dialyzed bacteriophage.

16. The method of claim 13, further comprising subjecting the single density gradient cesium chloride band that comprises bacteriophage to lipopolysaccharide-affinity chromatography to remove endotoxin and to generate a bacterial contaminant-free, or endotoxin-free, eluate.

17. The method of claim 16, further comprising subjecting the eluate to a process comprising dialysis in a sterile buffered saline, or a sterile phosphate buffered saline.

18. A method for purifying a bacteriophage from a sample comprising unpurified bacteriophages comprising or contaminated with a bacterial product or contaminant and generating a bacterial product- or contaminant-free preparation of the bacteriophage, comprising:

(a) providing a sample comprising an unpurified bacteriophage, wherein the sample comprises a bacteriophage lysate or culture, and to provide a sample, the lysate or culture is cooled to between 4° C. to 37° C., at the point where bacteriophage-insensitive or bacteriophage-resistant bacteria appear in the lysate or the culture; and (b) filtering the sample with a dead-end microfiltration or a pressure-driven CFF comprising a MWCO at 100 kDa, wherein any material smaller than a cross-flow membrane pore passes through the membrane, while bacteriophage particles that do not pass through the membrane remain in the retentate stream, and the CFF with a 100 kDa membrane pore size removes both free endotoxins, which are approximately 10 kDa in size, and exotoxins smaller than 30 kDa, and a membrane pore size of 100 kDa can retain an equivalent to a spherical particle with a 3 nm diameter, thereby retaining bacteriophage particles, thereby generating a bacterial product- or contaminant-free preparation of bacteriophage.

19. The method of claim 18, wherein step (b) comprises filtering the sample with a dead-end microfiltration and a pressure-driven CFF comprising a MWCO at 100 kDa.

20. The method of claim 18, wherein step (b) comprises ultrafiltering the sample with a dead-end microfiltration and a pressure-driven CFF comprising a MWCO at 100 kDa.

21. The method of claim 18, wherein the bacterial or contaminant comprises a bacterial endotoxin.

* * * * *